US008008270B2

(12) United States Patent
Vaillant et al.

(10) Patent No.: US 8,008,270 B2
(45) Date of Patent: Aug. 30, 2011

(54) ANTIVIRAL OLIGONUCLEOTIDES TARGETING VIRAL FAMILIES

(75) Inventors: Andrew Vaillant, Roxboro (CA); Jean-Marc Juteau, Blainville (CA)

(73) Assignee: Replicor Inc., Montreal (CA)

( * ) Notice: Subject to any disclaimer, the term of this patent is extended or adjusted under 35 U.S.C. 154(b) by 423 days.

(21) Appl. No.: 12/100,181

(22) Filed: Apr. 9, 2008

(65) Prior Publication Data

US 2009/0156527 A1 Jun. 18, 2009

Related U.S. Application Data

(60) Division of application No. 10/661,402, filed on Sep. 12, 2003, now abandoned, which is a continuation-in-part of application No. PCT/IB03/04573, filed on Sep. 11, 2003.

(60) Provisional application No. 60/430,934, filed on Dec. 5, 2002, provisional application No. 60/410,264, filed on Sep. 13, 2002.

(51) Int. Cl.
*A01N 43/04* (2006.01)
*C12Q 1/68* (2006.01)
*C12P 19/34* (2006.01)
*C07H 21/02* (2006.01)

(52) U.S. Cl. ............. 514/44; 435/6; 435/91.1; 435/455; 435/458; 435/536; 435/23.1

(58) Field of Classification Search ............. 435/6, 91.1, 435/455, 91.31, 458; 514/44, 1, 2; 536/23.1, 536/24.5
See application file for complete search history.

(56) References Cited

U.S. PATENT DOCUMENTS

| | | | |
|---|---|---|---|
| 3,687,808 A | 8/1972 | Merigan, Jr. et al. |
| 4,426,330 A | 1/1984 | Sears |
| 4,469,863 A | 9/1984 | Ts'o et al. |
| 4,534,899 A | 8/1985 | Sears |
| 4,615,697 A | 10/1986 | Robinson |
| 4,806,463 A | 2/1989 | Goodchild et al. |
| 5,013,556 A | 5/1991 | Woodle et al. |
| 5,023,243 A | 6/1991 | Tullis |
| 5,023,252 A | 6/1991 | Hseih |
| 5,130,302 A | 7/1992 | Spielvogel et al. |
| 5,177,198 A | 1/1993 | Spielvogel et al. |
| 5,213,804 A | 5/1993 | Martin et al. |
| 5,218,103 A | 6/1993 | Caruthers et al. |
| 5,223,618 A | 6/1993 | Cook et al. |
| 5,225,212 A | 7/1993 | Martin et al. |
| 5,248,670 A | 9/1993 | Draper et al. |
| 5,256,775 A | 10/1993 | Froehler |
| 5,264,221 A | 11/1993 | Tagawa et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,356,633 A | 10/1994 | Woodle et al. |
| 5,366,878 A | 11/1994 | Pederson et al. |
| 5,378,825 A | 1/1995 | Cook et al. |
| 5,386,023 A | 1/1995 | Sanghvi et al. |
| 5,452,496 A | 9/1995 | Long et al. |
| 5,476,925 A | 12/1995 | Letsinger et al. |
| 5,489,677 A | 2/1996 | Sanghvi et al. |
| 5,508,270 A | 4/1996 | Baxter et al. |
| 5,514,788 A | 5/1996 | Bennett et al. |
| 5,540,935 A | 7/1996 | Miyazaki et al. |
| 5,543,152 A | 8/1996 | Webb et al. |
| 5,556,948 A | 9/1996 | Tagawa et al. |
| 5,563,050 A | 10/1996 | Peyman et al. |
| 5,580,859 A | 12/1996 | Felgner et al. |
| 5,591,623 A | 1/1997 | Bennett et al. |
| 5,591,720 A | 1/1997 | Anderson et al. |
| 5,591,721 A | 1/1997 | Agrawal et al. |
| 5,602,244 A | 2/1997 | Caruthers et al. |
| 5,610,289 A | 3/1997 | Cook et al. |
| 5,625,050 A | 4/1997 | Beaton et al. |
| 5,652,355 A | 7/1997 | Metelev et al. |
| 5,665,710 A | 9/1997 | Rahman et al. |
| 5,670,634 A | 9/1997 | Marotta et al. |
| 5,684,148 A | 11/1997 | Caruthers et al. |
| 5,695,979 A | 12/1997 | Caruthers et al. |
| 5,705,188 A | 1/1998 | Junichi et al. |
| 5,750,666 A | 5/1998 | Caruthers et al. |
| 5,770,713 A | 6/1998 | Imbach et al. |

(Continued)

FOREIGN PATENT DOCUMENTS

EP 0 339 842 A2 11/1989

(Continued)

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Adjou et al., "A novel generation of heparan sulfate mimetics for the treatment of prion diseases", 2003, *J. Gen. Virol.* 84:2595-2603.
Agrawal, "Importance of nucleotide sequence and chemical modifications of antisense oligonucleotides", 1999, *Biochim. Biophys. Acta* 1489:53-68.

(Continued)

*Primary Examiner* — Jane Zara
(74) *Attorney, Agent, or Firm* — Norton Rose OR LLP

(57) ABSTRACT

Random sequence oligonucleotides that have antiviral activity are described, along with their use as antiviral agents. In many cases, the oligonucleotides are greater than 40 nucleotides in length. Also described are methods for the prophylaxis or treatment of a viral infection in a human or animal, and a method for the prophylaxis treatment of cancer caused by oncoviruses in a human or animal. The methods typically involve administering to a human or animal in need of such treatment, a pharmacologically acceptable, therapeutically effective amount of at least oligonucleotide that does not act by a sequence complementary mode of action.

43 Claims, 55 Drawing Sheets

U.S. PATENT DOCUMENTS

| | | | |
|---|---|---|---|
| 5,837,449 | A | 11/1998 | Monia et al. |
| 5,952,490 | A | 9/1999 | Hanecak et al. |
| 5,998,602 | A | 12/1999 | Torrence et al. |
| 6,013,240 | A | 1/2000 | Behr et al. |
| 6,013,639 | A | 1/2000 | Peyman et al. |
| 6,133,246 | A | 10/2000 | McKay et al. |
| 6,143,881 | A | 11/2000 | Metelev et al. |
| 6,177,246 | B1 | 1/2001 | Monia et al. |
| 6,184,369 | B1 | 2/2001 | Rando et al. |
| 6,316,190 | B1 | 11/2001 | Rein et al. |
| 6,346,614 | B1 | 2/2002 | Metelev et al. |
| 6,506,559 | B1 | 1/2003 | Fire et al. |
| 6,573,099 | B2 | 6/2003 | Graham |
| 6,608,035 | B1 | 8/2003 | Agrawal et al. |
| 7,358,068 | B2 * | 4/2008 | Vaillant et al. ............... 435/91.1 |
| 2003/0119019 | A1 | 6/2003 | Winnacker et al. |
| 2003/0162225 | A1 | 8/2003 | James et al. |
| 2003/0232435 | A1 | 12/2003 | Dobie |
| 2005/0009743 | A1 * | 1/2005 | Sundquist et al. .............. 514/12 |

FOREIGN PATENT DOCUMENTS

| | | |
|---|---|---|
| EP | 0 445 131 B1 | 9/1991 |
| EP | 0 496 813 B1 | 8/1992 |
| EP | 0 496 813 B1 | 12/1994 |
| WO | WO 90/04384 | 5/1990 |
| WO | WO 91/05545 | 5/1991 |
| WO | WO 92/03051 | 3/1992 |
| WO | WO 93/24510 | 12/1993 |
| WO | WO 94/02499 | 2/1994 |
| WO | WO 94/17093 | 8/1994 |
| WO | WO 94/20073 | 9/1994 |
| WO | WO 94/26764 | 11/1994 |
| WO | WO 96/10391 | 4/1996 |
| WO | WO 96/40062 | 12/1996 |
| WO | WO 97/04787 | 2/1997 |
| WO | WO 97/13499 | 4/1997 |
| WO | WO 97/30731 | 8/1997 |
| WO | WO 98/39352 | 9/1998 |
| WO | WO 99/14226 | 3/1999 |
| WO | WO 99/32619 | 7/1999 |
| WO | WO 01/75164 | 10/2001 |
| WO | WO 02/068582 | 9/2002 |
| WO | WO 03/002903 | 1/2003 |
| WO | WO 03/097661 | 11/2003 |
| WO | WO 2004/002419 | 1/2004 |

OTHER PUBLICATIONS

Agrawal and Kandimalla, "Antisense therapeutics: is it as simple as complementary base recognition?", 2000, *Mol. Med. Today* 6:72-81.

Akhtar et al., "The delivery of antisense therapeutics", 2000, *Advanced Drug Delivery Reviews* 44:3-21.

Allakhverdi et al., "Inhibition of Antigen-induced Eosinophilia and Airway Hyperresponsiveness by Antisense Oligonucleotides Directed against the Common β Chain of IL-3, IL-5, GM-CSF Receptors in a Rat Model of Allergic Asthma", 2002, *Am. J. Respir. Crit. Care Med.* 165:1015-1021.

Andreola et al., "DNA aptamers selected against the HIV-1 RNase H display in vitro antiviral activity", 2001, *Biochemistry*, 40:10087-10094.

Baker et al., "2-*O*-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells", 1997, *J. Biol. Chem.* 272 (18):11994-12000.

Ball et al., "Clinical Potential of Respirable Antisense Oligonucleotides (RASONs) in Asthma", 2003, *Am. J. Pharmacogenomics* 3 (2):97-106.

Banks et al., "Delivery across the Blood-Brain Barrier of Antisense Directed against Amyloid β: Reversal of Learning and Memory Deficits in Mice Overexpressing Amyloid Precursor Protein", 2001, *J. Pharmacol. Exp. Ther.* 297 (3):1113-1121.

Bardos et al., "Structure-Activity Relationships and Mode of Action of 5-Mercapto-Substituted Oligo- and Polynucleotides as Antitemplates Inhibiting Replication of Human Immunodeficiency Virus Type 1", 1992, *Antimicrob. Agents and Chemother*. 36 (1):108-114.

Barret et al., "Evaluation of Quinacrine Treatment for Prion Diseases", 2003, *J. of Virol*. 77 (15):8462-8469.

Bate et al., "Squalestatin Cures Prion-infected Neurons and Protects Against Prion Neurotoxicity", 2004, *J. of Biol. Chem.* 279 (15):14983-14990.

Boussif et al., "A versatile Vector for Gene and Oligonucleotide Transfer into Cells in Culture and in vivo: Polyethylenimine", 1995, *Proc. Natl. Acad. Sci. USA*. 92 (16):7297-7301.

Brigger et al., "Poly(ethylene glycol)-Coated Hexadecylcyanoacrylate Nanospheres Display a Combined Effect for Brain Tumor Targeting", 2002, *J. Pharmacol. Exp. Ther.* 303 (3):928-936.

Casper, "Discovery of a Novel Target for Potential Cancer Therapy", Joint Bayer Science Forum—ACS Nov. 24th Dinner Meeting. 2003, The Filterpaper, Andy Edelbrock Bayer Corporation, p. 3 (abstract).

Caughey et al., "Sulfated Polyanion Inhibition of Scrapie-Associated PrP Accumulation in Cultured Cells", 1993, *J. Virol*. 67 (2):643-650.

Chen et al., "Antisense Oligonucleotides Demonstrate a Dominant Role of c-Ki-RAS Proteins in Regulating the Proliferation of Diploid Human Fibroblasts", 1996, *J. Biol. Chem*. 271 (45):28259-28265.

Cheong et al., "Structure of influenza virus panhandle RNA studied by NMR spectroscopy and molecular modeling", 1999, *Nuc. Acids. Res*. 27 (5): 1392-1397.

Chiang et al., "Antisense Oligonucleotides Inhibit Intercellular Adhesion Molecule 1 Expression by Two Distinct Mechanisms", 1991, *J. Biol. Chem*. 266 (27):18162-18171.

Cioffi et al., "Selective Inhibition of A-Raf and C-Raf mRNA Expression by Antisense Oligodeoxynucleotides in Rat Vascular Smooth Muscle Cells: Role of A-Raf and C-Raf in Serum-Induced Proliferation", 1997, *Mol. Pharmacol*. 51:383-389.

Crooke et al., "In Vitro Toxicological Evaluation of ISIS 1082, a Phosphorothioate Oligonucleotide Inhibitor of Herpes Simplex Virus", 1992, *Antimicrob. Agents Chemother*. 36 (3):527-532.

Dass, "Vehicles for oligonucleotide delivery to tumours", 2002, *Journal of Pharmacy and Pharmacology* 54:3-27.

Dass, "Liposome-Mediated Delivery of Oligodeoxynuclotides in Vivo", 2002, *Drug Delivery*, 9:169-180.

Dheur et al., "Polyethylenimine but Not Cationic Lipid Improves Antisense Activity of 3'-Capped Phosphodiester Oligonucleotides", 1999, *Antisense & Nucleic Acid Drug Development*, 9:515-525.

Doh-Ura et al., "Treatment of Transmissible Spongiform Encephalopathy by Intraventricular Drug Infusion in Animal Models", 2004, *J. Virol*. 78 (10):4999-5006.

Elbashir et al., "RNA interference is mediated by 21- and 22-nucleotide RNAs", 2001, *Genes & Development* 15:188-200.

Elbashir et al., "Duplexes of 21-nucleotide RNAs mediate RNA interference in cultured mammalian cells", 2001, *Nature* 411:494-498.

Finotto et al., "Local administration of antisense phosphorothioate oligonucleotides to the c-kit ligand, stem cell factor, suppresses airway inflammation and IL-4 production in a murine model of asthma", 2001, *J. Allergy Clin. Immunol*. 107 (2) :279-286.

Fiset et al., "Modulation of allergic response in nasal mucosa by antisense oligodeoxynucleotides for IL-4", 2003, *J. Allergy Clin. Immunol*. 111 (3) :580-586.

Garrett et al., "In vivo use of oligonucleotides to inhibit choroidal neovascularisation in the eye", 2001, *J. Gene Med*. 3:373-383.

Gorlach et al., "Antisense repression in *Cryptococcus neoformans* as a laboratory tool and potential antifungal strategy", 2002, *Microbiology* 148:213-219.

Grigoriev et al., "Effects of the polyene antibiotic derivative MS-8209 on the astrocyte lysosomal system of scrapie-infected hamsters", 2002, *J. Mol. Neurosci*. 18:271-281.

Harboth et al., "Identification of essential genes in cultured mammalian cells using small interfering RNAs", 2001, *Journal of Cell Science* 114 (24) 4557-4565.

Horvath et al., "Potent inhibition of HIV-1 entry by $(s^4dU)_{35}$", 2005, *Virology* 334:214-223.

Hughes et al., "The cellular delivery of antisense oligonucleotides and ribozymes", 2001, *Drug Discovery Today*. 6 (6) :303-315.

Huwyler et al., "Brain drug delivery of small molecules using immunoliposomes", 1996, *Proc. Natl. Acad. Sci. USA* 93:14164-14169.

Inoue et al., "Synthesis and properties of novel nucleic acid probes", 1985, *Symposium Series—Nucleic Acids Research* No. 16:165-168.
Inoue et al., "Sequence-dependent hydrolysis of RNA using modified oligonucleotide splints and RNase H", 1987, *FEBS Letters* 215 (2):327-330.
Jaaskelainen et al., "A lipid carrier with a membrane active component and a small complex size are required for efficient cellular delivery of anti-sense phosphorothioate oligonucleotides", 2000, *European Journal of Pharmaceutical Sciences* 10:187-193.
Kanagaratnam et al., "Malaria merozoite surface protein antisense oligodeoxynucleotides lack antisense activity but function as polyanions to inhibit red cell invasion", 1998, *Int. J. Biochem. Cell Biol.* 30:979-985.
Kocisko et al., "New Inhibitors of Scrapie-Associated Prion Protein Formation in a Library of 2,000 Drugs and Natural Products", 2003, *J. Virol.* 77 (19):10288-10294.
Koster et al., "Emerging therapeutic agents for transmissible spongiform encephalopathies: a review", 2003, *J. Vet Pharmacol. Ther.* 26:315-26.
Kurreck, "Antisense technologies. Improvement through novel chemical modifications", 2003, *Eur. J. Biochem.* 270:1628-1644.
Kuwasaki et al., "Inhibition of human immunodeficiency virus 1 replication in vitro by a self-stabilized oligonucleotide with 2'-O-methyl-guanosine-uridine quadruplex motifs", 2003, *J. Antimicrob. Chemother.* 51:813-819.
Lau et al., "Abrogation of c-Raf expression induces apoptosis in tumor cells", 1998, *Oncogene* 16:1899-1902.
Leung and Shah, in: *Controlled Release of drugs: Polymers and aggregate systems*, Rosoff, M., Ed., 1989, VCH Publishers, New York, pp. 185-215.
Luo et al., "Inhibition of influenza viral polymerases by minimal viral RNA decoys", 1997, *J. Gen. Virol.* 78: 2329-2333.
de Mergny et al., "Kinetics and thermodynamics of i-DNA formation: phosphodiester versus modified oligodeoxynucleotides", 1998, *Nucleic Acids Res.* 26 (21): 4797-4803.
de Monbrison et al., "Introducing antisense oligonucleotides into *Pneumocystis carinii*", 2002, *J. Microbiol. Methods* 50:211-213.
Monia et al., "Evaluation of 2'-Modified Oligonucleotides Containing 2'-Deoxy Gaps as Antisense Inhibitors of Gene Expression", 1993, *J. Biol. Chem.* 268 (19):14514-14522.
Morassutti et al., "Effect of phosphorothioate modifications on the ability of GTn oligodeoxynucleotides to specifically recognize single-stranded DNA-binding proteins and to affect human cancer cellular growth" 1999, *Biochimie* 81:1115-1122.
Mou and Gray, "The high binding affinity of phosphorothioate-modified oligomers for Ff gene 5 protein is moderated by the addition of C-5 propyne or 2'-O-methyl modifications", 2002, *Nucleic Acids Res.* 30 (3):749-758.
Nakajima et al., "Results of Quinacrine Administration to Patients with Creutzfeldt-Jakob Disease", 2004, *Dement. Geriatr. Cogn. Disord.* 17:158-163.
Noguchi et al., "Remarkable induction of apoptosis in cancer cells by a novel cationic liposome complexed with a bcl-2 antisense oligonucleotide", 2003, *Journal of Controlled Release* 88:313-320.
Noonpakdee et al., "Inhibition of *Plasmodium falciparum* proliferation in vitro by antisense oligodeoxynucleotides against malarial topoisomerase II", 2003, *Biochem. and Biophys. Res. Commun.* 302:659-664.
O'Brien et al., "Antisense BCR-ABL Oligomers Cause Non-Specific Inhibition of Chronic Myeloid Leukemia Cell Lines", 1994, *Leukemia* 8 (12):2156-2162.
Omori et al., "Targeting of post-ischemic cerebral endothelium in rat by liposomes bearing polyethylene glycol-coupled transferrin", 2003, *Neurol. Res.* 25:275-279.
Orum et al., "Locked nucleic acids: A promising molecular family for gene-function analysis and antisense drug development", 2001, *Current Opinion in Molecular Therapeutics* 3 (3):239-243.
Pan et al., "Isolation of virus-neutralizing RNAs from a large pool of random sequences", 1995, *Proc. Natl. Acad. Sci. USA* 92:11509-11513.
Papucci et al., "Phosphodiester Oligonucleotides Inhibit Mitosis and Trigger Apoptosis by a Non-Antisense, p53-Mediated Mechanism", 2002, *Antisense & Nucleic Acid Drug Development* 12:21-31.

Perez et al., "Sequence-independent induction of Sp1 transcription factor activity by phosphorothioate oligodeoxynucleotides", 1994, *Proc. Natl. Acad. Sci. USA* 91:5957-5961.
Poli et al., "In vitro Evaluation of the Anti-prionic Activity of Newly Synthesized Congo Red Derivatives", 2003, *Arzneim.-Forsch./Drug Res.* 53 (12):875-888.
Priola et al., "Porphyrin and Phthalocyanine Antiscrapie Compounds", 2000, *Science* 287: 1503-1506.
Proske et al., "Prion-Protein-Specific Aptamer Reduces $PrP^{Sc}$ Formation", 2002, *Chemic. Biol.Chem.* 3:717-725.
Ramazeilles et al., "Antisense phosphorothioate oligonucleotides: Selective killing of the intracellular parasite *Leishmania amazonensis*", 1994, *Proc. Natl. Acad. Sci. USA* 91:7859-7863.
Rhie et al., "Characterization of 2'-fluoro-RNA aptamers that bind preferentially to disease-associated conformations of prion protein and inhibit conversion", 2003, *J. Biol. Chem.*, 278 (41):39697-39705.
Rieger, in: *Pharmaceutical Dosage Forms*, Lieberman, Rieger and Banker (Eds), 1988, Marcel Dekker, Inc., New York, NY, vol. 1, pp. 285-366.
Roh et al., "Down-Regulation of HER2/*neu* Expression Induces Apoptosis in Human Cancer Cells That Overexpress HER2/*neu*", 2000, *Cancer Research* 60:560-565.
Rosoff, in: *Pharmaceutical Dosage Forms*, Lieberman, Rieger and Banker (Eds), 1988, Marcel Dekker, Inc., New York, NY, vol. 1, pp. 245-282.
Schmidt et al., "Drug targeting by long-circulating liposomal glucocorticosteroids increases therapeutic efficacy in a model of multiple sclerosis", 2003, *Brain* 126 :1895-1904.
Shyng et al., "Sulfated Glycans Stimulate Endocytosis of the Cellular Isoform of the Prion Protein, $PrP^{C}$, in Cultured Cells", 1995, *J. Biol. Chem.* 270 (50):30221-30229.
Sierakowska et al., "Repair of thalassemic human β-globin mRNA in mammalian cells by antisense oligonucleotides", 1996, *Proc. Natl. Acad. Sci. USA* 93:12840-12844.
Smetsers et al., "An antisense Bcr-Abl phosphodiester-tailed methylphosphonate oligonucleotide reduces the growth of chronic myeloid leukaemia patient cells bay a non-antisense mechanism", 1997, *British Journal of Haematology* 96:377-381.
Supattapone et al., "Branched Polyamines Cure Prion-Infected Neuroblastoma Cells", 2001, *J. Virol.* 75 (7):3453-3461.
Tchatalbachev et al., "The packaging signal of influenza viral RNA molecules", 2001, *RNA* 7: 979-989.
Uhlmann and Peyman, "Antisense Oligonudeotides: A New Therapeutic Principle", 1990, *Chemical Reviews* 90 (4):544-584.
Van Deventer et al., "A randomised, controlled, double blind, escalating dose study of alicaforsen enema in active ulcerative colitis", 2004, *Gut.* 53:1646-1651.
Vinogradov et al., "Nanogels for Oligonucleotide Delivery to the Brain", 2004, *Bioconjug. Chem.* 15:50-60.
Wang et al., "Sequence-independent Inhibition of in Vitro Vascular Smooth Muscle Cell Proliferation, Migration, and in Vivo Neointimal Formation by Phosphorothioate Oligodeoxynucleotides", 1996, *J. Clin. Invest.* 98 (2):443-450.
White et al., "Inhibition of the Multiple Antibiotic Resistance (*mar*) Operon in *Escherichia coli* by Antisense DNA Analogs", 1997, *Antimicrobial Agents and Chemotherapy* 41 (12):2699-2704.
White et al., "Development of novel methods for delivering therapeutic oligonucleotides to the central nervous system", 2003, *Society for Neuroscience*, Program #325.5, Abstract.
White et al., "Antisense oligonucleotide treatments for psoriasis", 2004, *Expert. Opin. Biol. Ther.* 4(1):75-81.
Xu et al., "Inhibition of DNA Replication and Induction of S Phase Cell Cycle Arrest by G-rich Oligonucleotides", 2001, *The Journal of Biological Chemistry* 276 (46):43221-43230.
Yang et al., "Construction and selection of bead-bound combinatorial oligonucleoside phosphorothioate and phosphorodithioate aptamer libraries designed for rapid PCR-based sequencing", 2002, *Nucl. Acids Res.* 30 (23):1-8.
Yu et al., "Hybrid Oligonucleotides: Synthesis, Biophysical Properties, Stability Studies, and Biological Activity", 1996, *Bioorganic. Med. Chem.* 4 (10):1685-1692.
Yu et al., "Prediction of Clinical Responses in a Simulated Phase III Trial of Crohn's Patients Administered the Antisense Phosphorothioate Oligonucleotide ISIS 2302: Comparison of Proposed Dosing Regimens", 2003, *Antisense Nucleic Acid Drug Dev.* 13:57-66.

Zellweger et al., "Antitumor Activity of Antisense Clusterin Oligonucleotides Is Improved in Vitro and in Vivo by Incorporation of 2'-O-(2-Methoxy)Ethyl Chemistry", 2001, *J. Pharmacol. and Experimental Therapeutics* 298 (3):934-940.

Zhang et al., "A Simple Glycol Nucleic Acid", 2005, *J. Am. Chem. Soc.* 127:4174-4175.

Zhang et al., "The Study on Brain Targeting of the Amphotericin B Liposomes", 2003, *J. Drug. Target.* 11 (2):117-122.

Zhang et al., "Global Non-Viral Gene Transfer to the Primate Brain Following Intravenous Administration", 2003, *Mol. Ther.* 7 (1):11-18.

*The Concise Encyclopedia of Polymer Science and Engineering*, Jacqueline I. Kroschwitz, 1998, ISBN: 0-471-31856-6, 1341 pages, pp. 858-859.

Agrawal and Kandimalla, << Antisense and/or Immunostimulatory Oligonucleotide Therapeutics, >> *Current Cancer Drug Targets* 1:197-209 (2001).

Allen and Chonn, "Large Unilamellar Liposomes with Low Uptake into the Reticuloendothelial System," *FEBS Letters* 223(1):42-46 (1987).

Archambault, et al., "Phosphorothioate oligonucleotides inhibit the replication of lentviruses and type D retroviruses, but not that of type C retroviruses," *Arch Virol* 139:97-109 (1994).

Matsumura et al., Gastroenterology, vol. 137, pp. 673-681 (2009).

Bernstein et al., Antimicrobial Agents & Chemotherapy, vol. 52, No. 8, pp. 2727-2733 (2008).

Kocisko et al., Antimicrobial Agents & Chemotherapy, vol. 50, No. 3, pp. 1034-1044 (2006).

Lee et al., Virology, vol. 372, pp. 107-117 (2008).

Guzman et al., Antiviral Therapy, vol. 12, pp. 1147-1156 (2007).

Vaillant et al., Antimicrobial Agents & Chemotherapy, vol. 50, No. 4, pp. 1393-1401 (2006).

Cardin et al., Virology J., vol. 6, pp. 214-228 (2009).

Adjou et al., "A novel generation of heparan sulfate mimetics for the treatment of prion diseases", 2003, J. Gen. Virol. 84:2595-2603.

Agrawal, "Importance of nucleotide sequence and chemical modifications of antisense oligonucleotides", 1999, Biochim. Biophys. Acta 1489:53-68.

Agrawal and Kandimalla, "Antisense therapeutics: is it as simple as complementary base recognition?", 2000, Mol. Med. Today 6:72-81.

Agrawal and Kandimalla, "Antisense and/or immunostimulatory oligonucleotide therapeutics", 2001, Current Cancer Drug Targets 1:197-209.

Akhtar et al., "The delivery of antisense therapeutics", 2000, Advanced Drug Delivery Reviews 44:3 21.

Allakhverdi et al., "Inhibition of Antigen-induced Eosinophilia . . . ", 2002, Am. J. Respir. Crit. Care Med. 165:1015-1021.

Allen and Chonn, "Large unilamellar liposomes with Low uptake into the reticuloendothelial system", 1987, FEB 05191 223(1):42-46.

Andreola et al., "DNA aptamers selected against the HIV-1 RNase H display in vitro antiviral activity", 2001, Biochemistry, 40:10087-10094.

Archambault et al., "Phosphorothioate oligonucleotides inhibit the replication of lentiviruses . . . ", 1994, Arch. Virol. 139:97-109.

Baker et al., "2-O-(2-Methoxy)ethyl-modified Anti-intercellular Adhesion Molecule 1 (ICAM-1) Oligonucleotides . . . ". 1997, J. Biol. Chem. 272 (18):11994-12000.

Ball et al., "Clinical Potential of Respirable Antisense Oligonucleotides (RASONs) in Asthma", 2003, Am. J. Pharmacogenomics 3 (2):97-106.

Banks et al., "Delivery across the Blood-Brain Barrier of Antisense Directed against Amyloid β: . . . ", 2001, J. Pharmacol. Exp. Ther. 297 (3):1113-1121.

Bardos et al., "Structure-Activity Relationships and Mode of Action of . . . ", 1992, Antimicrob. Agents and Chemother. 36 (1):108-114.

Barret et al., "Evaluation of Quinacrine Treatment for Prion Diseases", 2003, J. of Virol. 77 (15):8462-8469.

Bate et al., "Squalestatin Cures Prion-infected Neurons and Protects Against Prion Neurotoxicity", 2004, J. of Biol. Chem. 279 (15):14983-14990.

Berkow et al., "Nonsteroidal anti-inflammatory drugs (NSAIDs)", 1997, The Merck Manual of Diagnosis and Therapy, 15th ed., 2499-2506.

Blume and Cevc, "Liposomes for the sustained drug release in vivo", 1990, Biochimica et Biophysica Acta 1029:91-97.

Boussif et al., "A versatile Vector for Gene and Oligonucleotide Transfer . . . ", 1995, Proc. Natl. Acad. Sci. USA. 92 (16):7297-7301.

Branch, "A good antisense molecule is hard to find" 1998, Trends in Biochemical Sciences 23: 45-50.

Brigger et al., "Poly(ethylene glycol)-Coated Hexadecylcyanoacrylate Nanospheres Display . . . ", 2002, J. Pharmacol. Exp. Ther. 303 (3):928-936.

Brunton, "Section VI—Drugs Affecting Gastrointestinal Function", 1996, The Pharmacological Basis of Therapeutics 9(38):934-935.

Buur et al., "Penetration of 5-fluorouracil and prodrugs across the intestine of the albino rabbit: . . . ", 1990, Journ. of Controlled Release 14:43-51.

Campbell and Rein, "In Vitro Assembly Properties of Human Immunodeficiency Virus Type I . . . ", 1999, Journ. of Virol. 73 (3) :2270-2279.

Casper, "Discovery of a Novel Target for Potential Cancer Therapy", ACS Meeting. 2003, The Filterpaper, A. Edelbrock Bayer Corp, p. 3 (abstract).

Caughey et al., "Sulfated Polyanion Inhibition of Scrapie-Associated PrP Accumulation in Cultured Cells", 1993, J. Virol. 67 (2):643-650.

Cevc et al., "Ultraflexible vesicles, Transfersomes, have an extremely low pore penetration resistance . . . ", 1998, Biochimica et Biophysica Acta 1368:201-215.

Chen et al., "Antisense Oligonucleotides Demonstrate a Dominant Role of c-Ki-RAS Proteins in Regulating the Proliferation . . . ", 1996, J. Biol. Chem. 271 (45):28259-28265.

Cheng et al., "Interactions Between Single-Stranded DNA Binding Protein and Oligonucleotide Analogs with Different . . . ", 1997, Journ. Mol. Recognition 10:101-107.

Cheong et al., "Structure of influenza virus panhandle RNA studied by NMR spectroscopy and molecular modeling", 1999, Nuc. Acids. Res. 27 (5): 1392-1397.

Chiang et al., "Antisense Oligonucleotides Inhibit Intercellular Adhesion Molecule 1 Expression by Two Distinct Mechanisms", 1991, J. Biol. Chem. 266 (27):18162-18171.

Chirila et al., "The use of synthetic polymers for the delivery of therapeutic antisense oligodeoxynucleotides". 2002, Biomaterials 23: 321-342.

Cioffi et al., "Selective Inhibition of A-Raf and C-Raf mRNA Expression by Antisense Oligodeoxynucleotides . . . ", 1997, Mol. Pharmacol. 51:383-389.

Constantinides et al., "Formulation and Intestinal Absorption Enhancement Evaluation of Water-in-Oil . . . ", 1994, Pharmaceutical Res. 11(10):1385-1390.

Crooke, "Progress in Antisense Technology: The End of the Beginning", 1999, Meth. in Enzym. 313:3-45.

Crooke, "Progress in antisense technology", 2004, Annual Review Medicine 55: 61-95.

Crooke et al., "In Vitro Toxicological Evaluation of ISIS 1082, a Phosphorothioate Oligonucleotide Inhibitor of . . . ", 1992, Antimicrob. Agents Chemother. 36 (3):527-532.

Crooke et al., "Pharmacokinetic Properties of Several Novel Oligonucleotide Analogs in mice", 1996, Journ. Pharm. and Experim. Therap. 277(2):923-937.

Dass, "Vehicles for oligonucleotide delivery to tumours", 2002, Journal of Pharmacy and Pharmacology 54:3-27.

Dass, "Liposome-Mediated Delivery of Oligodeoxynuclotides in Vivo", 2002, Drug Delivery, 9:169-180.

Ddheur et al., "Polyethylenimine but Not Cationic Lipid Improves Antisense Activity . . . ", 1999, Antisense & Nucleic Acid Drug Development, 9:515-525.

Doh-Ura et al., "Treatment of Transmissible Spongiform Encephalopathy by Intraventricular Drug Infusion in Animal Models", 2004, J. Virol. 78 (10):4999-5006.

Du Plessis et al., "Topical delivery of liposomally encapsulated gamma-interferon", 1992, Antivir. Res. 18:259-265.

Elbashir et al., "RNA interference is mediated by 21- and 22-nucleotide RNAs", 2001, Genes & Development 15:188-200.

Elbashir et al., "Duplexes of 21-nucleotide RNAs mediate RNA interference in cultured mammalian cells", 2001, Nature 411:494-498.

El-Hariri et al., "The Mitigating Effects of Phosphatidylcholines on Bile Salt- and Lysophosphatidylcholine-induced Membrane Damage", 1992, J. Pharm. Pharmacol. 44:651-654.

Englisch and Gauss, "Chemically Modified Oligonucleotides as Probes and Inhibitors", 1991, Angewandte Chemie 30(6):613-722.

Feng et al., "Reversible Binding of Recombinant Human Immunodeficiency Virus Type I Gag Protein to Nucleic Acids . . .", 2002, Journ. of Virol. 76(22):11757-11762.

Fennewald et al., "Inhibition of herpes simplex virus in culture by oligonucleotides composed entirely of deoxyguanosine and thymidine", 1995, Anti viral Res. 26:37-54.

Finotto et al., "Local administration of antisense phosphorothioate oligonucleotides to the c-kit ligand, . . . ", 2001, J. Allergy Clin. Immunol. 107 (2) :279-286.

Fiset et al., "Modulation of allergic response in nasal mucosa by antisense oligodeoxynucleotides for IL-4", 2003, J. Allergy Clin. Immunol. 111 (3) :580-586.

Gabizon et al., "Liposome formulations with prolonged circulation time in blood and enhanced uptake by tumors", 1988, Proc. Natl. Acad. Sci. USA 85:6949-6953.

Garrett et al., "In vivo use of oligonucleotides to inhibit choroidal neovascularisation in the eye", 2001, J. Gene Med. 3:373-383.

Gao et al., "Effect of Phosphorothioate Homo-oligodeoxynucleotides on Herpes Simplex Virus Type 2-induced DNA Polymerase", 1989, Journ. of Biol. Chem. 264(19): 11521-11526.

Gao et al., "Inhibition of Herpes Simplex Virus type 2 Growth by Phosphorothioate Oligodeoxynucleotides", 1990, Antimicrobial Agents and Chemotherapy 34(5):808-812.

Gorlach et al., "Antisense repression in *Cryptococcus neoformans* as a laboratory tool and potential antifungal strategy", 2002, Microbiology 148:213-219.

Grigoriev et al., "Effects of the polyene antibiotic derivative MS-8209 on the astrocyte lysosomal system of scrapie-infected hamsters", 2002, J. Mol. Neurosci. 18:271-281.

Harborth et al., "Identification of essential genes in cultured mammalian cells using small interfering RNAs", 2001, Journal of Cell Science 114 (24) 4557-4565.

Higuchi et al., "Particle Phenomena and Course Dispersions", 1985, Remington's Pharmaceutical Sciences Chapter 21 :301-329.

Ho et al., "Non-sequence-specific inhibition of transferrin receptor expression in HL-60 leukemia cells . . .", 1991, Antisense Res. Dev. 1: 329-342.

Ho et al., "Preparation of Microemulsions Using Plyglycerol Fatty Acid Esters as Surfactant for the Delivery of Protein Drugs", 1996, Journ. of Pharm. Sci. 85(2):138-143.

Horvath et al., "Potent inhibition of HIV-1 entry by (s4dU)35", 2005, Virology 334:214-223.

Hu et al., "Topical delivery of cyclosporine A from non-ionic liposomal systems: an in vivo/in vitro correlation . . . ", 1994, STP Pharma Sciences 4(6):466-469.

Hughes et al., "The cellular delivery of antisense oligonucleotides and ribozymes", 2001, Drug Discovery Today. 6 (6) :303-315.

Huwyler et al., "Brain drug delivery of small molecules using immunoliposomes", 1996, Proc. Natl. Acad. Sci. USA 93:14164-14169.

Illum and Davis, "The organ uptake of intravenously administered colloidal particles can be altered using a non-ionic surfactant (Poloxamer 338)", 1984, FEBS 1212 167(1):79-82.

Inagawa et al., "Inhibition of human immunodeficiency virus type 1 replication by P-stereodefined oligo (nucleoside phosphorothioate)s . . . ", 2002, FEBS 26461 528:48-52.

Inoue et al., "Synthesis and properties of novel nucleic acid probes", 1985, Symposium Series—Nucleic Acids Research No. 16:165-168.

Inoue et al. , "Sequence-dependent hydrolysis of RNA using modified oligonucleotide splints and RNase H", 1987, FEBS Letters 215 (2) :327-330.

Jaaskelainen et al., "A lipid carrier with a membrane active component and a small complex size are required . . . ", 2000, European Journal of Pharmaceutical Sciences 10:187-193.

Jairath et al., "Inhibition of respiratory syncytial virus replication by antisense oligodeoxyribonucleotides", 1997, Antiviral Res. 33:201-213.

Jarrett, "Affinity chromatography with nucleic acid polymers", 1993, J. Chromotography 6I8:315-339.

Kabanov et al., "A new class of antivirals: antisense oligonucleotides combined with a hydrophobic substituent . . . ", 1990, FEBS 07982 259 (2) :327-330.

Kanagaratnam et al., "Malaria merozoite surface protein antisense oligodeoxynucleotides . . . ", 1998, Int. J. Biochem. Cell Biol. 30:979-985.

Kandimalla et al., "Effects of phosphorothioate oligodeoxyribonucleotide and oligoribonucleotides on human complement . . . ", 1998, Bioorg. & Med. Chem. Lett. 8:2103-2108.

Kean et al., "Inhibition of Herpes Simplex Virus Replication by Antisense Oligo-2'-O-methylribonucleoside Methylphosphonates", 1995, Biochemistry 34(45):14617-14620.

Klibanov et al., "Amphipathic polyethyleneglycols effectively prolong the circulation time of liposomes", 1990, FEBS 08706 268(1):235-237.

Klimuk et al., "Enhanced Anti-Inflammatory Activity of a Liposomal Intercellular Adhesion Molecule-1 Antisense . . . ", 2000, Journ. of Pharm. & Exper. Ther. 292 (2) :480-488.

Kocisko et al., "New Inhibitors of Scrapie-Associated Prion Protein Formation in a Library of 2,000 Drugs and Natural Products", 2003, J. Virol. 77 (19) :10288-10294.

Kool, "Replacing the Nucleobases in DNA with Designer Molecules", 2002, Acc. Chem. Res. 35:936-943.

Koster et al., "Emerging therapeutic agents for transmissible spongiform encephalopathies: a review", 2003, J. Vet Pharmacol. Ther. 26:315-26.

Kurreck, "Antisense technologies. Improvement through novel chemical modifications", 2003, Eur. J. Biochem. 270:1628-1644.

Kuwasaki et al., "Inhibition of human immunodeficiency virus 1 replication in vitro by a self-stabilized oligonucleotide . . . ", 2003, J. Antimicrob. Chemother. 51:813-819.

Lau et al., "Abrogation of c-Raf expression induces apoptosis in tumor cells", 1998, Oncogene 16:1899-1902.

Lavigne et al., "Is Antisense an Appropriate Nomenclature or Design for Oligodeoxynucleotides Aimed at the Inhibition of HIV-1 . . . ", 2002, AAPS PharmSci. 4 (2) article 9 :1-11.

Lebedeva and Stein, "Antisense Oligonucleotides: Promise and Reality", 2001, Annu. Rev. Pharmacol. Toxicol. 41:403-419.

Lee et al., "Mucosal Penetration Enhancers for Facilitation of Peptide and Protein Drug Absorption", 1991, Crit. Rev. in Ther. Drug Carrier Syst. 8(2):91-192.

Lerner et al., "A six-month trial of valacyclovir in the Epstein-Barr virus subset of chronic fatigue syndrome: . . . ", 2002, Drugs of Today 38(8): 549-561.

Letsinger et al., "Cholesteryl-conjugated oligonucleotides: Synthesis, properties, and activity as inhibitors of . . . ", 1989, Proc. Nat!. Acad. Sd. USA 86:6553-6556.

Leung and Shah, in: Controlled Release of drugs: Polymers and aggregate systems, Rosoff, M., Ed., 1989, VCH Publishers, New York, pp. 185-215.

Luo et al., "Inhibition of influenza viral polymerases by minimal viral RNA decoys", 1997, J. Gen. Virol. 78: 2329-2333.

Manoharan et al., "Chemical Modifications to Improve Uptake and Bioavailability of Antisense Oligonucleotides", 1992, Ann. N.Y. Acad. of Sci. 660:306-309.

Manoharan et al., "Introduction of a lipophilic thioether tether in the minor groove of nucleic acids . . . ", 1993, Bioorg. & Med. Chem. Letters 3 (12) :2765-2770.

Manoharan et al., "Cholic acid-oligonucleotide conjugates for antisense applications", 1994, Bioorg. & Med. Chem. Lett. 4 (8) :1053-1060.

Manoharan et al., "Oligonucleotide conjugates: Alteration of the pharmacokinetic properties of antisense agents", 1995, Nucleosides & Nucleotides 14(3-5):969-973.

Manoharan et al., "Lipidic Nucleic Acids," 1995, Tetrahedron Letters 36 (21) :3651-3654.

Marhsall et al., "Inhibition of human immunodeficiency virus activity by phosphorodithioate oligodeoxycytidine", 1992, Proc. Nat!. Acad. Sci. USA 89:6265-6269.

Marshall and Caruthers, "Phosphorodithioate DNA as a Potential Therapeutic Drug", 1993, Science 259 (5101) :1564-1570.

Matsukura et al., "Antisense phosphorothioates as antivirals against human immunodeficiency virus (HIV) and hepatitis B virus (HBV)", 1995, Toxicology Letters, 82/83: 435-438.

Matsukura et al., "Phosphorothioate Analogs of Oligodeoxynucleotides: Inhibitors of Replication . . . ", 1987, Proc. Natl. Acad. of Sciences of USA 84 (21) :7706-7710.

de Mergny et al., "Kinetics and thermodynamics of i-DNA formation: phosphodiester versus modified oligodeoxynucleotides", 1998, Nucleic Acids Res. 26 (21): 4797-4803.

Mishra et al., "Improved leishmanicidal effect of phosphorotioate antisense oligonucleotides by LDL-mediated delivery", 1995, Biochimica et Biophysica Acta 1264:229-237.

Miyano-Kurosaki et al., "Inhibition of HTLV-I Induction and Virus-Induced Syncytia Formation by Oligodeoxynucleotides", 1996, Virus Genes 12 (3) :205-217.

Miyao et al., "Stability and Pharmacokinetic Characteristics of Oligonucleotides Modified at Terminal Linkages in Mice", 1995, Antisense Res. & Dev. 5:115-121.

de Monbrison et al., "Introducing antisense oligonucleotides into Pneumocystis carinii", 2002, J. Microbiol. Methods 50:211-213.

Monia et al., "Evaluation of 2'-Modified Oligonucleotides Containing 2'-Deoxy Gaps as Antisense . . . ", 1993, J. Biol. Chem. 268 (19) :14514-14522.

Monteith et al., "Preclinical Evaluation of the Effects of a Novel Antisense Compound Targeting C-raf Kinase in Mice and Monkeys", 1998, Toxicolog. Sciences 46:365-375.

Morassutti et al., "Effect of phosphorothioate modifications on the ability of GTn oligodeoxynucleotides to specifically recognize . . . " 1999, Biochimie 81:1115-1122.

Morris et al., "High Affinity Ligands from in vitro selection: Complex targets," 1998, Proc. Natl. Acad. Sci. USA 95:2902-2907.

Mou and Gray, "The high binding affinity of phosphorothioate-modified oligomers for Ff gene 5 protein is moderated by . . . ", 2002, Nucleic Acids Res. 30 (3) :749-758.

Muranishi, "Absorption Enhancers", 1990, Crit. Rev, in Ther. Drug Carr. Syst. 7 (1) :1-33.

Nakajima et al., "Results of Quinacrine Administration to Patients with Creutzfeldt-Jakob Disease", 2004, Dement. Geriatr. Cogn. Disord. 17:158-163.

Nandi et al., "DNA-induced Partial Unfolding of Prion Protein Leads to its Polymerisation to Amyloid", 2002, J. Mol. Biol. 322:153-161.

Neurath et al., Anti-HIV-1 activity of anionic polymers: a comparative study of candidate microbicides, 2002, BMC Infectious Diseases 2:1-11.

Noguchi et al., "Remarkable induction of apoptosis in cancer cells by a novel cationic liposome . . . ", 2003, Journal of Controlled Release 88:313-320.

Noonpakdee et al., "Inhibition of *Plasmodium falciparum* proliferation in vitro . . . ", 2003, Biochem. and Biophys. Res. Commun. 302:659-664.

Oberhauser and Wagner, "Effective incorporation of 2'-O-methyl-oligoribonucleotides into liposomes . . . ", 1992, Nucleic Acids Res. 20(3):533-538.

O'Brien et al., "Antisense BCR-ABL Oligomers Cause Non-Specific Inhibition of Chronic Myeloid Leukemia Cell Lines", 1994, Leukemia 8 (12) :2156-2162.

Ojwang et al., "T30177, an oligonucleotide stabilized by an intramolecular guanosine octet . . . ", 1995, Antimicrob. Agents. Chemother. 39: 2426-2435.

Olivieri et al., "Hepatitis C virus and arthritis", 2003, Rheumatic Diseases Clinics of North America 29 (1) :1-18.

Omori et al., "Targeting of post-ischemic cerebral endothelium in rat by liposomes bearing polyethylene glycol-coupled transferrin", 2003, Neurol. Res. 25:275-279.

Opalinska and Gewirtz, "Nucleic-acid therapeutics: basic principled and recent applications.", 2002, Nature Rev. Drug Discov. 1: 503-514.

Orum et al., "Locked nucleic acids: a promising molecular family for gene-function analysis . . . ", 2001, Current Opinion in Molecular Therapeutics 3 (3):239-243.

Pan et al., "Isolation of virus-neutralizing RNAs from a large pool of random sequences", 1995, Proc. Natl. Acad. Sci. USA 92:11509-11513.

Papahadjopoulos et al., "Targeting of Liposomes to Tumor Cells in Vivo", 1987, Ann. N.Y. Acad. Sci. pp. 64-74.

Papucci et al., "Phosphodiester Oligonucleotides Inhibit Mitosis and Trigger Apoptosis . . . ", 2002, Antisense & Nucleic Acid Drug Development 12:21-31.

Peracchi, "Prospects for antiviral riobzymes and deoxyribozymes.", 2004, A. Rev. Med. Virol. 14: 47-64.

Perez et al., "Sequence-independent induction of Sp1 transcription factor activity by phosphorothioate oligodeoxynucleotides", 1994, Proc. Natl. Acad. Sci. USA 91:5957-5961.

Peyman et al., "Inhibition of Viral Growth by Antisense Oligonucleotides Directed against . . . ", 1995, Biol. Chem. Hoppe-Seyler 376:195-198.

Poli et al., "In vitro Evaluation of the Anti-prionic Activity of Newly Synthesized Congo Red Derivatives", 2003, Arzneim.-Forsch./Drug Res. 53 (12):875-888.

Priola et al., "Porphyrin and Phthalocyanine Antiscrapie Compounds", 2000, Science 287: 1503-1506.

Proske et al., "Prion-Protein-Specific Aptamer Reduces PrPSc Formation", 2002, Chemic. Biol.Chem. 3:717-725.

Ramazeilles et al., "Antisense phosphorothioate oligonucleotides: Selective killing of the intracellular parasite . . . ", 1994, Proc. Natl. Acad. Sci. USA 91:7859-7863.

Rhie et al., "Characterization of 2'-fluoro-RNA aptamers that bind preferentially to disease-associated conformations . . . ", 2003, J. Biol. Chem., 278 (41):39697-39705.

Rieger, in: Pharmaceutical Dosage Forms, Lieberman, Rieger and Banker (Eds), 1988, Marcel Dekker, Inc., New York, NY, vol. 1, pp. 285-366.

Ritschel, "Standards of Clinical Investigations in the USA", 1993, Meth. Find Exp. Clin. Pharmacol. 15(4):207-215.

Roh et al., "Down-Regulation of HER2/neu Expression Induces Apoptosis in Human Cancer Cells That Overexpress HER2/neu", 2000, Cancer Research 60:560-565.

Rosoff, in: Pharmaceutical Dosage Forms, Lieberman, Rieger and Banker (Eds), 1988, Marcel Dekker, Inc., New York, NY, vol. 1, pp. 245-282.

Saison-Behmoaras et al., "Short modified antisense oligonucleotides directed against Ha-ras . . . ", 1991, The EMBO Journal 10 (5) :1111-1118.

Sanghvi, "Heterocyclic base modifications in nucleic acids . . . ", 1993, CRC Press, Inc., Antisense Research and Applications Ch. 15:273-288.

Schmidt et al., "Drug targeting by long-circulating liposomal glucocorticosteroids increases therapeutic efficacy in a model of . . . ", 2003, Brain 126 :1895-1904.

Schott, "Colloidal Dispersions",1985, Remington's Pharmaceutical Sciences Ch. 20:271-300.

Shea et al., "Synthesis, hybridization properties and antiviral activity of lipid-oligodeoxynucleotide conjugates", 1990, Nucleic Acids Res. 18 (13) :3777-3783.

Shyng et al., "Sulfated Glycans Stimulate Endocytosis of the Cellular Isoform of the Prion Protein, PrPC, in Cultured Cells", 1995, J. Biol. Chem. 270 (50) :30221-30229.

Sierakowska et al., "Repair of thalassemic human beta-globin mRNA in mammalian cells by antisense oligonucleotides", 1996, Proc. Natl. Acad. Sci. USA 93:12840-12844.

Smetsers et al., "An antisense Bcr-Abl phosphodiester-tailed methylphosphonate oligonucleotide reduces the growth . . . ", 1997, British Journal of Haematology 96:377-381.

Stahl et al., "High Incidence of Parvovirus B19 DNA in Synovial Tissue of Patients with Undifferentiated Mono- and Oligoarthritis", 2000, Clin. Rheumatol. 19:281-286.

Stein, "The experimental use of antisense oligonucleotides: a guide for the perplexed", 2001, J. Clin. Invest. 108(5):641-644.

Stein and Cheng, "Antisense Oligonucleotides as Therapeutic Agents—Is the Bullet Really Magical?", 1993, Science 261(5124):1004-1012.
Stein et al., "Phosphorothioate Oligodeoxynucleotides Are Potent Sequence Nonspecific Inhibitors of, . . . ", 1989, AIDS Res. & Human Retro viruses 5 (6):639-646.
Sunamoto et al., "Liposome Membranes. V. Interaction of Zinc(II) Ion with Egg Phosphatidylcholine Liposomes", 1980, Bull. Chem. Soc. Japan 53 (10):2778-2781.
Supattapone et al., "Branched Polyamines Cure Prion-Infected Neuroblastoma Cells", 2001, J. Virol. 75 (7):3453-3461.
Svinarchuk et al., "Inhibition of HIV proliferation in MT-4 cells by antisense oligonucleotide conjugated to lipophilic groups", 1993, Biochimie 75:49-54.
Swinyard, 1990, Remington's Pharmaceutical Sciences 18th Ed., Ch. 39:782-783.
Takahashi and Yamada, "Viral Etiology for Parkinson's Disease—A Possible Role of Influenza A Virus Infection", 1999, Jpn J. Infect. Dis. 52:89-98.
Takahashi et al., "The Use of Perfluorochemical Emulsion as a Vascular Perfusate in Drug Absorption", 1988, J. Pharm. Pharmacol 40:252-257.
Takakura et al., "Uptake Characteristics of Oligonucleotides in the Isolated Rat Liver Perfusion System", 1996, Antisense & Nucleic Acid Drug Develpmt. 6:177-183.
Takeshita et al., "Oligodeoxynucleotides Containing Synthetic Abasic Sites", 1987, Journ. of Biol. Chem. 262 (21):10171-10179.
Talbot et al., "Virus-Induced Autoimmune Reactions in the CNS", 2001, Curr Top Microbiol Immunol 253:247-271.
Tchatalbachev et al., "The packaging signal of influenza viral RNA molecules", 2001, RNA 7: 979-989.
Tonkinson et al., "Cellular Pharmacology and Protein Binding of Phosphoromonothioate . . . ", 1994, Antisense Res. & Develpmt. 4:269-278.
Trus et al., "The herpes simplex virus procapsid: structure, conformational changes upon maturation . . . ", 1996, J. Mol. Biol. 263: 447-462.
Uhlmann and Peyman, "Antisense Oligonucleotides: A New Therapeutic Principle", 1990, Chemical Reviews 90 (4):544-584.
Van Deventer et al., "A randomised, controlled, double blind, escalating dose study of alicaforsen enema in active ulcerative colitis", 2004, Gut. 53:1646-1651.
Vinogradov et al., "Nanogels for Oligonucleotide Delivery to the Brain", 2004, Bioconjug. Chem. 15:50-60.
Vives et al., "Lipophilic pro-oligonucleotides are rapidly and efficiently internalized in HeLa cells", 1999, Nucleic Acids Res. 27 (20):4071-4076.
Walter et al., "Viral induction of a chronic asthma phenotype and genetic segregation from the acute response", 2002, Journ. of Clin. Invest. 110 (2):165-175.
Wang and Huang, "Plasmid DNA Adsorbed to pH-sensitive liposomes efficiently transforms the target cells", 1987, Bioch. & Biophys. Res. Comm. 147(3):980-985.
Wang et al., "Sequence-independent Inhibition of in Vitro Vascular Smooth Muscle Cell Proliferation . . . ", 1996, J. Clin. Invest. 98 (2):443-450.
Weiner et al., "Liposomes: A Novel Topical Delivery System for Pharmaceutical and Cosmetic Applications", 1994, Journ. of Drug Targeting 2:405-410.
White et al., "Inhibition of the Multiple Antibiotic Resistance (mar) Operon in *Escherichia coli* . . . ", 1997, Antimicrobial Agents and Chemotherapy 41 (12):2699-2704.
White et al., "Development of novel methods for delivering therapeutic . . . ", 2003, Society for Neuroscience, Program #325.5, Abstract.
White et al., "Antisense oligonucleotide treatments for psoriasis", 2004, Expert. Opin. Biol. Ther. 4(1):75-81.
Wu et al., "Increased Microvascular Permeability Contributes to Preferential Accumulation of Stealth Liposomes in Tumor Tissue", 1993, Cancer Research 53:3765-3770.
Xu et al., "Inhibition of DNA Replication and Induction of S Phase Cell Cycle Arrest . . . ", 2001, The Journal of Biological Chemistry 276 (46):43221-43230.
Yamamoto et al., "A Mechanistic Study on Enhancement of Rectal Permeability to Insulin in the Albino Rabbit", 1992, Journ. of Pharm. and Exp. Ther. 263 (1):25-31.
Yamashita et al., "Effects of diclofenac sodium and disodium ethylenediaminetetraacetate on electrical parameters . . . ", 1987, J. Pharm. Pharmacol. 39:621-626.
Yamashita et al., "Effect of Adjuvants on Charge-Selective Permeability and Electrical Resistance to Rat Jejunal Membrane", 1990, Journ. of Pharm. Sciences 79 (7):579-583.
Yang et al., "Construction and selection of bead-bound combinatorial oligonucleoside phosphorothioate . . . ", 2002, Nucl. Acids Res. 30 (23):1-8.
Yu et al., "Hybrid Oligonucleotides: Synthesis, Biophysical Properties, Stability Studies, and Biological Activity", 1996, Bioorganic. Med. Chem. 4 (10):1685-1692.
Yu et al., "Stereo-Enriched Phosphorothioate Oligodeoxynucleotides: Synthesis, Biophysical and Biological Properties", 2000, Biorg. & Medicinal Chem. 8:275-284.
Yu et al., "Prediction of Clinical Responses in a Simulated Phase III Trial of Crohn's Patients . . . ", 2003, Antisense Nucleic Acid Drug Dev. 13:57-66.
Zamecnik et al., "Inhibition of replication and expression of human T-cell lymphotropic virus type III . . . ", 1986, Proc. Natl. Acad. Sci. USA 83:4143-4146.
Zellweger et al., "Antitumor Activity of Antisense Clusterin Oligonucleotides Is Improved in Vitro . . . ", 2001, J. Pharmacol. and Experimental Therapeutics 298 (3):934-940.
Zhang et al., "A Simple Glycol Nucleic Acid", 2005, J. Am. Chem. Soc. 127:4174-4175.
Zhang et al., "The Study on Brain Targeting of the Amphotericin B Liposomes", 2003, J. Drug. Target. 11 (2):117-122.
Zhang et al., "Global Non-Viral Gene Transfer to the Primate Brain Following Intravenous Administration", 2003, Mol. Ther. 7 (1):11-18.
Zhou and Huang, "Targeted delivery of DNA by liposomes and polymers", 1992, Journ. of Controlled Release 19: 269-274.
The Concise Encyclopedia of Polymer Science and Engineering, Kroschwitz, J. I., ed. John Wiley & Sons, 1990, pp. 858-859.
The Merck Manual of Diagnosis and Therapy, 1987, 15:1206-1228.

* cited by examiner

| Drug | IC50 (uM) |
|---|---|
| REP 2003 | 4.01 |
| REP 2004 | 0.065 |
| REP 2006 | 0.014 |
| REP 2007 | 0.015 |
| Amprenavir | 0.016 |
| Indinavir | 0.006 |
| Lopinavir | 0.004 |
| Saquinavir | 0.003 |

| Drug | IC50 (uM) | | Fold change in IC50 |
| --- | --- | --- | --- |
| | HIV-1 NL4-3 | HIV-1 MRDC4 | |
| REP 2003 | 4.01 | 3.69 | 0.92 |
| REP 2004 | 0.065 | 0.046 | 0.71 |
| REP 2006 | 0.014 | 0.014 | 1.00 |
| REP 2007 | 0.015 | 0.013 | 0.87 |
| Amprenavir | 0.017 | 0.065 | 3.82 |
| Indinavir | 0.006 | 0.08 | 13.33 |
| Lopinavir | 0.004 | 0.096 | 24.00 |
| Saquinavir | 0.003 | 0.006 | 2.00 |

SEQUENCE COMPOSITION VS ANTI-HSV EFFICACY

FIG. 37a

Effect of sequence composition on efficacy against HSV-1

ANTIVIRAL OLIGONUCLEOTIDES TARGETING VIRAL FAMILIES

RELATED APPLICATIONS

This application is a divisional application of U.S. Ser. No. 10/661,402 filed on Sep. 12, 2003, now abandoned which itself is a continuation-in-part of Juteau & Vaillant, PCT application serial number PCT/IB/03/04573 filed Sep. 11, 2003, entitled ANTIVIRAL OLIGONUCLEOTIDES, and claims the benefit of Vaillant & Juteau, U.S. Provisional Appl. 60/430,934, filed Dec. 5, 2002, and of Vaillant & Juteau, U.S. Provisional Appl. 60/410,264, filed Sep. 13, 2002, all of which are incorporated herein by reference in their entireties, including drawings.

FIELD OF THE INVENTION

The present invention relates to oligonucleotides having antiviral activities and their use as therapeutic agents in viral infections caused by human and animal viruses and in cancers caused by oncogene viruses and in other diseases whose etiology is viral-based.

BACKGROUND OF THE INVENTION

The following discussion is provided solely to assist the understanding of the reader, and does not constitute an admission that any of the information discussed or references cited constitute prior art to the present invention.

Many important infectious diseases afflicting mankind are caused by viruses. Many of these diseases, including rabies, smallpox, poliomyelitis, hepatitis, yellow fever, immune deficiencies and various encephalitic diseases, are frequently fatal. Others are significant in that they are highly contagious and create acute discomfort such as influenza, measles, mumps and chickenpox, as well as respiratory or gastrointestinal disorders. Others such as rubella and cytomegalovirus can cause congenital abnormalities. Finally there are viruses, known as oncoviruses, which can cause cancer in humans and animals.

Among viruses, the family of Herpesviridae is of great interest. The Herpesviridae are a ubiquitous class of icoshedral, double stranded DNA viruses. Of over 100 characterized members of Herpesviridae (HHV), only eight infect humans. The best known among these are Herpes simplex type 1 (HSV-1), Herpes simplex type 2 (HSV-2), Varicella zoster (chicken pox or shingles), cytomegalovirus (CMV) and Epstein-Barr virus (EBV). The prevalence of Herpes viruses in humans is high, affecting at least one third of the worldwide population; and in the United States, 70-80% of the population have some kind of Herpes infection. While the pathology of Herpes infections are usually not dangerous, as in the case of HSV-1 which usually only causes short lived lesions around the mouth and face, these viruses are also known to be the cause of more dangerous symptoms, which vary from genital ulcers and discharge to fetal infections which can lead to encephalitis (15% mortality) or disseminated infection (40% mortality).

Herpes viruses are highly disseminated in nature and highly pathogenic for man. For example, Epstein-Barr virus (EBV) is known to cause infectious mononucleosis in late childhood or adolescence or in young adults. The hallmarks of acute infectious mononucleosis are sore throat, fever, headache, lymphadenopathy, enlarged tonsils and atypical, dividing lymphocytes in the peripheral blood. Other manifestations frequently include mild hepatitis, splenomegaly and encephalitis. EBV is also associated with two forms of cancer: Burkitt's lymphoma (BL) and the nasopharyngeal carcinoma (NPC). In endemic areas of equatorial Africa, BL is the most common childhood malignancy, accounting for approximately 80% of cancers in children. While moderately observed in North American Caucasians, NPC is one of the most common cancers in Southern China with age incidence of 25 to 55 years. EBV, like the cytomegalovirus, is also associated with post-transplant lymphoproliferative disease, which is a potentially fatal complication of chronic immunosuppression following solid organ or bone marrow transplantation.

Other diseases are also associated with HSV, including skin and eye infections, for example, chorioretinitis or keratoconjunctivitis. Approximately 300,000 cases of HSV infections of the eye are diagnosed yearly in the United States.

AIDS (acquired immunodeficiency syndrome) is caused by the human immunodeficiency virus (HIV). By killing or damaging cells of the body's immune system, HIV progressively destroys the body's ability to fight infections and certain cancers. There are currently approximately 42 million people living with HIV/AIDS worldwide. A total of 3.1 million people died of HIV/AIDS related causes in 2002. The ultimate goal of anti-HIV drug therapy is to prevent the virus from reproducing and damaging the immune system. Although substantial progress has been made over the past fifteen years in the fight against HIV, a cure still eludes medical science. Today, physicians have more than a dozen antiretroviral agents in three different drug classes to manage the disease. Typically, drugs from two or three classes are prescribed in a variety of combinations known as HAART (Highly Active AntiRetroviral Treatment). HAART therapies typically comprise two nucleoside reverse transcriptase inhibitors drugs with a third drug, either a protease inhibitor or a non-nucleoside reverse transcriptase inhibitor. Clinical studies have shown that HAART is the most effective means of reducing viral loads and minimizing the likelihood of drug resistance.

While HAART has been shown to reduce the amount of HIV in the body, commonly known as viral load, tens of thousands of patients encounter significant problems with this therapy. Some side effects are serious and include abnormal fat metabolism, kidney stones, and heart disease. Other side effects such as nausea, vomiting, and insomnia are less serious, but still problematic for HIV patients that need chronic drug therapy for a lifetime.

Currently approved anti-HIV drugs work by entering an HIV infected CD4+ T cell and blocking the function of a viral enzyme, either the reverse transcriptase or a protease. HIV needs both of these enzymes in order to reproduce. However, HIV frequently mutates and become resistant, rendering reverse transcriptase or protease inhibitor drugs ineffective. Once resistance occurs, viral loads increase and dictate the need to switch the ineffective agent for another antiretroviral agent. Unfortunately, when a virus becomes resistant to one drug in a class, other drugs in that class may become less effective. This phenomenon known as cross-resistance, occurs because many anti-HIV drugs work in similar manners. The occurrence of drug cross-resistance is highly undesirable because it reduces the available number of treatment options for patients.

There is therefore a great need for the development of other antiviral agents effective against HIV that work through other mechanisms of action against which the virus has not developed resistance. This is becoming especially important in view of recent data showing that 1 out of 10 patients newly diagnosed with HIV in Europe, is infected with a strain of HIV already resistant to at least one of the approved drug on the market.

Respiratory syncytial virus (RSV) causes upper and lower respiratory tract infections. It is a negative-sense, enveloped RNA virus and is highly infectious. It commonly affects young children and is the most common cause of lower respiratory tract illness in infants. RSV infections are usually associated with moderate-to-severe cold-like symptoms. However, severe lower respiratory tract disease may occur at any age, especially in elderly or immunocompromised patients. Children with severe infections may require oxygen therapy and, in certain cases, mechanical ventilation. According to the American Medical Association, an increasing number of children are being hospitalized for bronchiolitis, often caused by RSV infection. RSV infections also account for approximately one-third of community-associated respiratory virus infections in patients in bone marrow transplant centers. In the elderly population, RSV infection has been recently recognized to be very similar in severity to influenza virus infection.

Influenza (INF), also known as the flu, is a contagious disease that is caused by the influenza virus. It attacks the respiratory tract in humans (nose, throat, and lungs). An average of about 36,000 people per year in the United States die from influenza, and 114,000 per year require hospitalization as a result of influenza.

In all infectious diseases, the efficacy of a given therapy often depends on the host immune response. This is particularly true for herpes viruses, where the ability of all herpes viruses to establish latent infections results in an extremely high incidence of reactivated infections in immunocompromised patients. In renal transplant recipients, 40% to 70% reactivate latent HSV infections, and 80% to 100% reactivate CMV infections. Such viral reactivations have also been observed with AIDS patients.

The hepatitis B virus (HBV) is a DNA virus that belongs to the Hepadnaviridae family of viruses. HBV causes hepatitis B in humans. It is estimated that 2 billion people have been infected (1 out of 3 people) in the world. About 350 million people remain chronically infected and an estimated 1 million people die each year from hepatitis B and its complications. HBV can cause lifelong infection, cirrhosis of the liver, liver cancer, liver failure, and death. The virus is transmitted through blood and bodily fluids. This can occur through direct blood-to-blood contact, unprotected sex, use of unsterile needles, and from an infected woman to her newborn during the delivery process. Most healthy adults (90%) who are infected will recover and develop protective antibodies against future hepatitis B infections. A small number (5-10%) will be unable to get rid of the virus and will develop chronic infections while 90% of infants and up to 50% of young children develop chronic infections when infected with the virus. Alpha-interferon is the most frequent type of treatment used, Significant side effects are related to this treatment including flu-like symptoms, depression, rashes, other reactions and abnormal blood counts. Another treatment option includes 3TC which also has many side effects associated with its use. In the last few years, there has been an increasing number of reports showing that patients treated with 3TC are developing resistant strains of HBV. This is especially problematic in the population of patients who are co-infected with HBV and HIV. There is clearly an urgent need to develop new antiviral therapies against this virus.

Hepatitis C virus (HCV) infection is the most common chronic bloodborne infection in the United States where the number of infected patients likely exceeds 4 million. This common viral infection is a leading cause of cirrhosis and liver cancer, and is now the leading reason for liver transplantation in the United States. Recovery from infection is uncommon, and about 85 percent of infected patients become chronic carriers of the virus and 10 to 20 percent develop cirrhosis. It is estimated that there are currently 170 million people worldwide who are chronic carriers. According to the Centers for Disease Control and Prevention, chronic hepatitis C causes between 8,000 and 10,000 deaths and leads to about 1,000 liver transplants in the United States alone each year. There is no vaccine available for hepatitis C. Prolonged therapy with interferon alpha, or the combination of interferon with Ribavirin, is effective in only about 40 percent of patients and causes significant side effects.

Today, the therapeutic outlook for viral infections in general is not favourable. In general, therapies for viruses have mediocre efficacies and are associated with strong side effects which either prevent the administration of an effective dosage or prevent long term treatment. Three clinical situations which exemplify these problems are herpesviridae, HIV and RSV infections.

In the case of herpesviridae, there are five major treatments currently approved for use in the clinic: idoxuridine, vidarabine, acyclovir, foscarnet and ganciclovir. While having limited efficacy, these treatments are also fraught with side effects. Allergic reactions have been reported in 35% of patients treated with idoxuridine, vidarabine can result in gastrointestinal disturbances in 15% of patients and acyclovir, foscarnet and ganciclovir, being nucleoside analogs, affect DNA replication in host cells. In the case of ganciclovir, neutropenia and thrombocytopenia are reported in 40% of AIDS patients treated with this drug.

While there are many different drugs currently available for the treatment of HIV infections, all of these are associated with side effects potent enough to require extensive supplemental medication to give patients a reasonable quality of life. The additional problem of drug resistant strains of HIV (a problem also found in herpesviridae infections) usually requires periodic changing of the treatment cocktail and in some cases, makes the infection extremely difficult to treat.

The treatment of RSV infections in young infants is another example of the urgent need for new drug development. In this case, the usual line of treatment is to deliver Ribavirin by inhalation using a small-particle aerosol in an isolation tent. Not only is Ribavirin only mildly effective, but its uses is associated with significant side effects. In addition, the potential release of the drug has caused great concern in hospital personnel because of the known teratogenicity of Ribavirin.

It is clear that for any new emerging antiviral drug being developed, it would be highly desirable to incorporate the three following features: 1—improved efficacy; 2—reduced risks of side effects and 3—a mechanism of action which is difficult for the virus to overcome by mutation.

Several attempts to inhibit particular viruses by various antisense approaches have been made.

Zamecnik et al. have used ONs specifically targeted to the reverse transcriptase primer site and to splice donor/acceptor sites (Zamecnik, et al (1986) *Proc. Natl. Acad. Sci. USA* 83:4143-) (Goodchild & Zamecnik (1989) U.S. Pat. No. 4,806,463).

Crooke and coworkers. (Crooke et al. (1992) *Antimicrob. Agents Chemother.* 36:527-532) described an antisense against HSV-1.

Draper et al., (1993) (U.S. Pat. No. 5,248,670) have reported antisense oligonucleotides having anti-HSV activity containing the Cat sequence and hybridizing to the HSV-1 genes UL13, UL39 and UL40.

Kean et al. (*Biochemistry* (1995) 34:14617-14620) have tested antisense methylphosphonate oligomers as anti-HSV agents.

Peyman et al. (*Biol Chem Hoppe Seyler* (1995) March; 376:195-198) have reported testing specific antisense oligonucleotides directed against the IE110 and the UL30 mRNA of HSV-1 for their antiviral properties.

Oligonucleotides or oligonucleotide analogs targeting CMV mRNAs coding for IE1, IE2 or DNA polymerase were reported by Anderson et al (1997) (U.S. Pat. No. 5,591,720)

Hanecak et al (1999) (U.S. Pat. No. 5,952,490) have described modified oligonucleotides having a conserved G quartet sequence and a sufficient number of flanking nucleotides to significantly inhibit the activity of a virus such as HSV-1.

Jairath et al (Antiviral Res. (1997) 33:201-213) have reported antisense oligonucleotides against RSV.

Torrence et al (1999) (U.S. Pat. No. 5,998,602) have reported compounds comprising an antisense component complementary to a single stranded portion of the RSV antigenomic strand (the mRNA strand), a linker and a oligonucleotide activator of RNase L.

Qi et al. (*Zhonghua Shi Yan He Lin Chuang Bing Du Xue Za Zhi* (2000) 14:253-256) have reported testing antisense PS-ODNs in Coxsackie virus B3.

International publication WO9203051 (Roizman and Maxwell) describes methylphosphonate antisense oligomers which are complementary to vital regions of HSV viral genome or mRNA transcripts thereof which exhibit antiviral activity.

Guanosine/thymidine or guanosine-rich phosphorothioate oligodeoxynucleotides (GT-PS-ODNs) have been reported to have antiviral activity. The article stated that "several different PS-containing CT-rich ODNs (B106-140, I100-12, and G106-57) all 26 or 27 nt in length, were just as effective at reducing HIV-2 titers as GT-rich ODNs consisting of 36 (B106-96, B106-97) or 45 nt (Table 4)." (Fennewald et al., Antiviral Res. (1995) 26:37-54).

In U.S. Pat. No. 6,184,369, anti-HIV, anti-HSV, and anti-CMV oligonucleotides containing a high percentage of guanosine bases are described. In preferred embodiments, the oligonucleotide has a three dimensional structure and this structure is stabilized by guanosine tetrads. In a further embodiment, the oligonucleotide compositions of the invention have two or more runs of two contiguous deoxyguanosines The patent claims a G-rich ODN that includes at least two G residues in at least two positions.

Cohen et al. (U.S. Pat. Nos. 5,264,423 and 5,276,019) described the inhibition of replication of HIV, and more particularly to PS-ODN analogs that can be used to prevent replication of foreign nucleic acids in the presence of normal living cells. Cohen et al describe antiviral activity of antisense PS-ODNs specific to a viral sequence. They also describe testing polyA, polyT and polyC PS-ODN sequences of 14, 18, 21 and 28-mers and indicate an antiviral effect of those PS-ODNs.

Matsukura et al. (Matsukura et al (1987) *Proc Natl Acad Sci USA* 84:7706-7710) later published the result described in Cohen et al, US patents above.

Gao et al (Gao et al (1989) *J Biol Chem* 264:11521-11526), describe the inhibition of replication of HSV-2, by PS-ODNs by testing of polyA, polyT and polyC PS-ODN sequences in sizes of 7, 15, 21 and 28 nucleotides.

Archambault, Stein and Cohen (Archambault et al (1994) *Arch Virol* 139:97109) report that a PS-ODN polyC of 28 nucleotides is not effective against HSV-1.

Stein et al (Stein et al. (1989) *AIDS Res Hum Retrovir* 5:639-646), published results concerning additional data on anti-HIV ODNs, generally of 21-28 nucleotides in length.

Marshal et al. (Marshall et al. (1992) *Proc. Natl Acad. Sci. USA* 89:6265-6269) describe anti-HIV-1 effect of phosphorothioate and phosphorothioate poly-C oligos of 4-28 nucleotides in length.

Stein & Cheng (Stein et al. (1993) *Science* 261:1004-1012), in a review article, mention the antiviral activity of non specific ODNs of 28 nucleotides, stating that "the anti-HIV properties of PS oligos are significantly influenced by non-sequence-specific effects, that is, the inhibitory effect is independent of the base sequence."

In a review article Lebedeva & Stein (Lebedeva et al (2001) *Annul Rev Pharmacol* 41:403-419) report a variety of non-specific protein binding activity of PS-ODNs, including viral proteins. They state that "these molecules are highly biologically active, and it is often relatively easy to mistake artifact for antisense".

Rein et al. (U.S. Pat. No. 6,316,190) reported a GT rich ON decoy linked to a fusion partner and binding to the HIV nucleocapsid, which can be used as an antiviral compound. Similarly, Campbell et al. (Campbell et al (1999) *J. Virol* 73:2270-2279) reported PO-ODN with a TGTGT motif binding specifically to the nucleocapsid of HIV but with no references to an antiviral activity.

Feng at al. (Feng et al. (2002) *J. Virol.* 76:11757-11762) described A(n) and TG(n) PO-ODNs binding to the recombinant HIV nucleocapsid but with no data nor references to an anti-HIV activity.

Antisense ODNs developed as anticancer agents, antiviral agents, or to treat others diseases are typically approximately 20 nucleotides in length. In a review article (Stein, C A, (2001) *J. Clin. Invest* 108:641-644), it is affirmed that "the length of an antisense oligonucleotide must be optimized: If the antisense oligonucleotide is either too long or too short, an element of specificity is lost. At the present time, the optimal length for an antisense oligonucleotide seems to be roughly 16-20 nucleotides". Similarly, in another review article (Crooke, S T (2000)*Methods Enzymol.* 313:3-45) it is stated that "Compared to RNA and RNA duplex formation, a phosphorothioate oligodeoxynucleotide has a $T_m$ approximately −2.2° lower per unit. This means that to be effective in vitro, phosphorothioate oligodeoxynucleotides must typically be 17- to −20-mer in length . . . ".

Caruthers and co-workers (Marshall et al. (1992) Proc. Natl. Acad. Sci. USA 89:6265-6269) reported anti-HIV activity of phosphorodithioate ODNs (PS2 ODNs) for a 12mer polycytidine-PS2-ODN and for a 14mer PS2-ODN. No other sizes were tested for anti-HIV activity. They also reported the inhibition of HIV reverse transcriptase (RT) for 12, 14, 20 and 28mer polycytidine-PS2-ODNs. Later, (Marshal et al (1993) Science 259:1564-1570) reported results showing sequence specific inhibition of the HIV RT. The same group published data for PS2-ODNs in several patents. In U.S. Pat. Nos. 5,218,103 and 5,684,148, PS2-ODN structure and synthesis is described. In U.S. Pat. Nos. 5,452,496, 5,278,302, and 5,695,979 inhibition of HIV PT is described for PS2-ODNs not longer than 15 bases. In U.S. Pat. Nos. 5,750,666 and 5,602,244, antisense activity of PS2-ODNs is described.

SUMMARY OF THE INVENTION

The present invention involves the discovery that oligonucleotides (ONs), e.g., oligodeoxynucleotides (ODNs), can have a broadly applicable, non-sequence complementary antiviral activity. Thus, it is not necessary for the oligonucleotide to be complementary to any viral sequence or to have a particular distribution of nucleotides in order to have antiviral activity. Such an oligonucleotide can even be prepared as a randomer, such that there will be at most a few copies of any particular sequence in a preparation, e.g., in a 15 micromol randomer preparation 32 or more nucleotides in length.

In addition, the inventors discovered that different length oligonucleotides have varying antiviral effect, and further that the length of antiviral oligonucleotide that produces maximal antiviral effect is in the range of 40-120 nucleotides. In view of the present discoveries concerning antiviral properties of oligonucleotides, this invention provides oligonucleotide antiviral agents that can have activity against numerous different viruses, and can even be selected as broad-spectrum antiviral agents. Such antiviral agents are particularly advantageous in view of the limited antiviral therapeutic options currently available.

Therefore, the ONs, e.g., ODNs, of the present invention are useful in therapy for treating or preventing viral infections or for treating or preventing tumors or cancers induced by viruses, such as oncoviruses (e.g., retroviruses, papillomaviruses, and herpesviruses), and in treating or preventing other diseases whose etiology is viral-based. Such treatments are applicable to many types of patients and treatments, including, for example, the prophylaxis or treatment of viral infections in immunosuppressed human and animal patients.

In a first aspect, the invention provides an antiviral oligonucleotide formulation that includes at least one antiviral oligonucleotide, e.g., at least 6 nucleotides in length, adapted for use as an antiviral agent, where the antiviral activity of the oligonucleotide occurs principally by a non-sequence complementary mode of action. Such a formulation can include a mix of different oligonucleotides, e.g., at least 2, 3, 5, 10, 50, 100, or even more.

As used herein in connection with oligonucleotides or other materials, the term "antiviral" refers to an effect of the presence of the oligonucleotides or other material in inhibiting production of viral particles, i.e., reducing the number of infectious viral particles formed, in a system otherwise suitable for formation of infectious viral particles for at least one virus. In certain embodiments of the present invention, the antiviral oligonucleotides will have antiviral activity against multiple different virus.

The term "antiviral oligonucleotide formulation" refers to a preparation that includes at least one antiviral oligonucleotide that is adapted for use as an antiviral agent. The formulation includes the oligonucleotide or oligonucleotides, and can contain other materials that do not interfere with use as an antiviral agent in vivo. Such other materials can include without restriction diluents, excipients, carrier materials, and/or other antiviral materials.

As used herein, the term "pharmaceutical composition" refers to an antiviral oligonucleotide formulation that includes a physiologically or pharmaceutically acceptable carrier or excipient. Such compositions can also include other components that do not make the composition unsuitable for administration to a desired subject, e.g., a human.

In the context of the present invention, unless specifically limited the term "oligonucleotide (ON)" means oligodeoxynucleotide (ODN) or oligodeoxyribonucleotide or oligoribonucleotide. Thus, "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. Examples of modifications that can be used are described herein. Oligonucleotides that include backbone and/or other modifications can also be referred to as oligonucleosides.

As used in connection with an antiviral formulation, pharmaceutical composition, or other material, the phrase "adapted for use as an antiviral agent" indicates that the material exhibits an antiviral effect and does not include any component or material that makes it unsuitable for use in inhibiting viral production in an in vivo system, e.g., for administering to a subject such as a human subject.

As used herein in connection with antiviral action of a material, the phrase "non-sequence complementary mode of action" indicates that the mechanism by which the material exhibits an antiviral effect is not due to hybridization of complementary nucleic acid sequences, e.g., an antisense effect. Conversely, a "sequence complementary mode of action" means that the antiviral effect of a material involves hybridization of complementary nucleic acid sequences. Thus, indicating that the antiviral activity of a material is "not primarily due to a sequence complementary mode of action" means that the activity of the oligonucleotide satisfies at least one of the 4 tests provided herein (see Example, 10) for determining whether the antiviral activity is "not primarily due to a sequence complementary mode of action". In particular embodiments, the oligonucleotide satisfies test 1, test 2, test 3, or test 4; the oligonucleotide satisfies a combination of two of the tests, i.e., tests 1 & 2; tests 1 & 3; tests 1 & 4, tests 2 & 3, tests 2 & 4, or tests 3 & 4; the oligonucleotide satisfies a combination of 3 of the tests, i.e., tests 1, 2, and 3, tests 1, 2, and 4, tests 1, 3, and 4, or tests 2, 3, and 4; the oligonucleotide satisfies all of tests 1, 2, 3, and 4.

As used herein in connection with administration of an antiviral material, the term "subject" refers to a living higher organism, including, for example, animals such as mammals, e.g., humans, non-human primates, bovines, porcines, ovines, equines, dogs, and cats; birds; and plants, e.g., fruit trees.

A related aspect concerns an antiviral oligonucleotide randomer formulation, where the antiviral activity of the randomer occurs principally by a non-sequence complementary mode of action. Such a randomer formulation can, for example, include a mixture of randomers of different lengths, e.g., at least 2, 3, 5, 10, or more different lengths.

As used herein in connection with oligonucleotide sequences, the term "random" characterizes a sequence or an ON that is not complementary to a viral mRNA, and which is selected to not form hairpins and not to have palindromic sequences contained therein. When the term "random" is used in the context of antiviral activity of an oligonucleotide toward a particular virus, it implies the absence of complementarity to a viral mRNA of that particular virus. The absence of complementarity may be broader, e.g., for a plurality of viruses, for viruses from a particular viral family, or for infectious human viruses.

In the present application, the term "randomer" is intended to mean a single stranded DNA having a wobble (N) at every position, such as NNNNNNNNNN. Each base is synthesized as a wobble such that this ON actually exists as a population of different randomly generated sequences of the same size.

In another aspect, the invention provides an oligonucleotide having antiviral activity against a target virus, where the oligonucleotide is at least 29 nucleotides in length (or in particular embodiments, at least 30, 32, 34, 36, 38, 40, 46, 50, 60, 70, 80, 90, 100, 110, or 120 nucleotides in length) and the sequence of the oligonucleotide is not complementary to any portion of the genome sequence of the target virus.

In another aspect, the invention provides an oligonucleotide formulation, containing at least one oligonucleotide having antiviral activity against a target virus, where the oligonucleotide is at least 6 nucleotides in length (in particular embodiments, at least 29, 30, 32, 34, 36, 38, 40, 46, 50, 60, 70, 80, 90, 100, 110, or 120 nucleotides in length) and the sequence of oligonucleotide is less than 70% complementary to any portion of the genomic nucleic acid sequence of the target virus and does not consist essentially of polyA, polyC, polyG, polyT, Gquartet, or a TG-rich sequence. In particular embodiments, the oligonucleotide has less than 65%, 60%, 55%, 50%, 80% 90%, 95%, or 100% complementarity to any portion of the genomic nucleic acid sequence of the target virus.

As used in connection with the present oligos, the term "TG-rich" indicates that the sequence of the antiviral oligonucleotide consists of at least 70 percent T and G nucleotides, or if so specified, at least 80, 90, or 95% T and G, or even 100%.

Related aspects concern isolated, purified or enriched antiviral oligonucleotides as described herein, e.g., as described for antiviral oligonucleotide formulations, as well as other oligonucleotide preparations, e.g., preparations suitable for in vitro use.

Antiviral oligonucleotides useful in the present invention can be of various lengths, e.g., at least 6, 10, 14, 15, 20, 25, 28, 29, 30, 35, 38, 40, 46, 50, 60, 70, 80, 90, 100, 110, 120, 140, 160, or more nucleotides in length. Likewise, the oligonucleotide can be in a range, e.g., a range defined by taking any two of the preceding listed values as inclusive end points of the range, for example 10-20, 2040, 30-50, 40-60, 40-80, 60-120, and 80-120 nucleotides. In particular embodiments, a minimum length or length range is combined with any other of the oligonucleotide specifications listed herein for the present antiviral oligonucleotides.

The antiviral oligonucleotide can include various modifications, e.g., stabilizing modifications, and thus can include at least one modification in the phosphodiester linkage and/or on the sugar, and/or on the base. For example, the oligonucleotide can include one or more phosphorothioate linkages, phosphorodithioate linkages, and/or methylphosphonate linkages; modifications at the 2'-position of the sugar, such as 2'-O-methyl modifications, 2'-amino modifications, 2'-halo modifications such as 2'-fluoro; acyclic nucleotide analogs, and can also include at least one phosphodiester linkage. Other modifications are also known in the art and can be used. In oligos that contain only 2'-O-methyl modifications, the oligo should not have 2'-O-methyl modifications throughout, as current results suggest that such oligos do not have suitable activity. In particular embodiments, the oligonucleotide has modified linkages throughout, e.g., phosphorothioate; has a 3'- and/or 5'-cap; includes a terminal 3'-5' linkage; the oligonucleotide is or includes a concatemer consisting of two or more oligonucleotide sequences joined by a linker(s).

In particular embodiments, the oligonucleotide binds to one or more viral proteins; the sequence of the oligonucleotide (or a portion thereof, e.g., at least ½) is derived from a viral genome; the activity of an oligonucleotide with a sequence derived from a viral genome is not superior to a randomer oligonucleotide or a random oligonucleotide of the same length; the oligonucleotide includes a portion complementary to a viral sequence and a portion not complementary to a viral sequence; the sequence of the oligonucleotide is derived from a viral packaging sequence or other viral sequence involved in an aptameric interaction; unless otherwise indicated, the sequence of the oligonucleotide includes A(x), C(x), G(x), T(x), AC(x), AG(x), AT(x), CG(x), CT(x), or GT(x), where x is 2, 3, 4, 5, 6, . . . 60 . . . 120 (SEQ ID NOS 27-36, respectively) (in particular embodiments the oligonucleotide is at least 29, 30, 32, 34, 36, 38, 40, 46, 50, 60, 70, 80, 90, 100, 110, or 120 nucleotides in length or the length of the specified repeat sequence is at least a length just specified); the oligonucleotide is single stranded (RNA or DNA); the oligonucleotide is double stranded (RNA or DNA); the oligonucleotide includes at least one Gquartet or CpG portion; the oligonucleotide includes a portion complementary to a viral mRNA and is at least 29, 37, or 38 nucleotides in length (or other length as specified above); the oligonucleotide includes at least one non-Watson-Crick oligonucleotide and/or at least one nucleotide that participates in non-Watson-Crick binding with another nucleotide; the oligonucleotide is a random oligonucleotide, the oligonucleotide is a randomer or includes a randomer portion, e.g., a randomer portion that has a length as specified above for oligonucleotide length; the oligonucleotide is linked or conjugated at one or more nucleotide residues to a molecule that modifies the characteristics of the oligonucleotide, e.g. to provide higher stability (such as stability in serum or stability in a particular solution), lower serum interaction, higher cellular uptake, higher viral protein interaction, improved ability to be formulated for delivery, a detectable signal, improved pharmacokinetic properties, specific tissue distribution, and/or lower toxicity.

Oligonucleotides can also be used in combinations, e.g., as a mixture. Such combinations or mixtures can include, for example, at least 2, 4, 10, 100, 1000, 10000, 100,000, 1,000,000, or more different oligonucleotides. Such combinations or mixtures can, for example, be different sequences and/or different lengths and/or different modifications and/or different linked or conjugated molecules. In particular embodiments of such combinations or mixtures, a plurality of oligonucleotides have a minimum length or are in a length range as specified above for oligonucleotides. In particular embodiments of such combinations or mixtures, at least one, a plurality, or each of the oligonucleotides can have any of the other properties specified herein for individual antiviral oligonucleoties (which can also be in any consistent combination).

The phrase "derived from a viral genome" indicates that a particular sequence has a nucleotide base sequence that has at least 70% identity to a viral genomic nucleotide sequence or its complement (e.g., is the same as or complementary to such viral genomic sequence), or is a corresponding RNA sequence. In particular embodiments of the present invention, the term indicates that the sequence is at least 70% identical to a viral genomic sequence of the particular virus against which the oligonucleotide is directed, or to its complementary sequence. In particular embodiments, the identity is at least 80, 90, 95, 98, 99, or 100%.

The invention also provides an antiviral pharmaceutical composition that includes a therapeutically effective amount of a pharmacologically acceptable, antiviral oligonucleotide at least 6 nucleotides in length (or other length as listed herein), where the antiviral activity of the oligonucleotide occurs principally by a non-sequence complementary mode of action, and a pharmaceutically acceptable carrier. In particular embodiments, the oligonucleotide or a combination or mixture of oligonucleotides is as specified above for individual oligonucleotides or combinations or mixtures of oligonucleotides. In particular embodiments, the pharmaceutical compositions are approved for administration to a human, or a non-human animal such as a non-human primate.

In particular embodiments, the pharmaceutical composition is adapted for the treatment, control, or prevention of a disease with a viral etiology; adapted for treatment, control, or prevention of a prion disease; is adapted for delivery by intraocular administration, oral ingestion, enteric administration, inhalation, cutaneous, subcutaneous, intramuscular, intraperitoneal, intrathecal, intratracheal, or intravenous injection, or topical administration. In particular embodiments, the composition includes a delivery system, e.g., targeted to specific cells or tissues; a liposomal formulation, another antiviral drug, e.g., a non-nucleotide antiviral polymer, an antisense molecule, an siRNA, or a small molecule drug.

In particular embodiments, the antiviral oligonucleotide, oligonucleotide preparation, oligonucleotide formulation, or antiviral pharmaceutical composition has an IC50 for a target virus (e.g., any of particular viruses or viruses in a groups of viruses as indicated herein) of 0.50, 0.20, 0.10, 0.09. 0.08, 0.07, 0.75, 0.06, 0.05, 0.045, 0.04, 0.035, 0.03, 0.025, 0.02, 0.015, or 0.01 µM or less.

In particular embodiments of formulations, pharmaceutical compositions, and methods for prophylaxis or treatment, the composition or formulation is adapted for treatment, control, or prevention of a disease with viral etiology; is adapted for the treatment, control or prevention of a prion disease; is adapted for delivery by a mode selected from the group consisting of intraocular, oral ingestion, enterally, inhalation, or cutaneous, subcutaneous, intramuscular, or intravenous injection delivery; further comprises a delivery system, which can include or be associated with a molecule increasing affinity with specific cells; further comprises at least one other antiviral drug in combination; and/or further comprises an antiviral polymer in combination.

As used herein in connection with antiviral oligonucleotides and formulations, and the like, in reference to a particular virus or group of viruses the term "targeted" indicates that the oligonucleotide is selected to inhibit that virus or group of viruses. As used in connection with a particular tissue or cell type, the term indicates that the oligonucleotide, formulation, or delivery system is selected such that the oligonucleotide is preferentially present and/or preferentially exhibits an antiviral effect in or proximal to the particular tissue or cell type.

As used herein, the term "delivery system" refers to a component or components that, when combined with an oligonucleotide as described herein, increases the amount of the oligonucleotide that contacts the intended location in vivo, and/or extends the duration of its presence at the target, e.g., by at least 20, 50, or 100%, or even more as compared to the amount and/or duration in the absence of the delivery system, and/or prevents or reduces interactions that cause side effects.

As used herein in connection with antiviral agents and other drugs or test compounds, the term "small molecule" means that the molecular weight of the molecule is 1500 daltons or less. In some cases, the molecular weight is 1000, 800, 600, 500, or 400 daltons or less.

In another aspect, the invention provides a kit that includes at least one antiviral oligonucleotide or oligonucleotide formulation in a labeled package, where the antiviral activity of the oligonucleotide occurs principally by a non-sequence complementary mode of action and the label on the package indicates that the antiviral oligonucleotide can be used against at least one virus.

In particular embodiments the kit includes a pharmaceutical composition that includes at least one antiviral oligonucleotide as described herein; the antiviral oligonucleotide is adapted for in vivo use in an animal and/or the label indicates that the oligonucleotide or composition is acceptable and/or approved for use in an animal; the animal is a mammal, such as human, or a non-human mammal such as bovine, porcine, a ruminant, ovine, or equine; the animal is a non-human animal; the kit is approved by a regulatory agency such as the U.S. Food and Drug Administration or equivalent agency for use in an animal, e.g., a human.

In another aspect, the invention provides a method for selecting an antiviral oligonucleotide, e.g., a non-sequence complementary antiviral oligonucleotide, for use as an antiviral agent. The method involves synthesizing a plurality of different random oligonucleotides, testing the oligonucleotides for activity in inhibiting the ability of a virus to produce infectious virions, and selecting an oligonucleotide having a pharmaceutically acceptable level of activity for use as an antiviral agent.

In particular embodiments, the different random oligonucleotides comprises randomers of different lengths; the random oligonucleotides can have different sequences or can have sequence in common, such as the sequence of the shortest oligos of the plurality; and/or the different random oligonucleotides comprise a plurality of oligonucleotides comprising a randomer segment at least nucleotides in length or the different random oligonucleotides include a plurality of randomers of different lengths. Other oligonucleotides, e.g., as described herein for antiviral oligonucleotides, can be tested in a particular system.

In yet another aspect, the invention provides a method for the prophylaxis or treatment of a viral infection in a subject by administering to a subject in need of such treatment a therapeutically effective amount of at least one pharmacologically acceptable oligonucleotide as described herein, e.g., a non-sequence complementary oligonucleotide at least 6 nucleotides in length, or an antiviral pharmaceutical composition or formulation containing such oligonucleotide. In particular embodiments, the virus can be any of those listed herein as suitable for inhibition using the present invention; the infection is related to a disease or condition indicated herein as related to a viral infection; the subject is a type of subject as indicated herein, e.g., human, non-human animal, non-human mammal, plant, and the like; the treatment is for a viral disease or disease with a viral etiology, e.g., a disease as indicated in the Background herein.

In particular embodiments, an antiviral oligonucleotide (or oligonucleotide formulation or pharmaceutical composition) as described herein is administered; administration is a method as described herein; a delivery system or method as described herein is used; the viral infection is of a DNA virus or an RNA virus; the virus is a parvoviridae, papovaviridae, adenoviridae, herpesviridae, poxviridae, hepadnaviridae, or papillomaviridae; the virus is a arenaviridae, bunyaviridae, calciviridae, coronaviridae, filoviridae, flaviridae, orthomyxoviridae, paramyxoviridae, picornaviridae, reoviridae, rhabdoviridae, retroviridae, or togaviridae; the herpesviridae virus is EBV, HSV-1, HSV-2, CMV, VZV, HHV-6, HHV-7, or HHV-8; the virus is HIV-1 or HIV-2; the virus is RSV; the virus is an influenza virus, e.g., influenza A; the virus is HBV; the virus is smallpox virus or vaccinia virus; the virus is a coronavirus; the virus is SARS virus; the virus is West Nile Virus; the virus is a hantavirus; the virus is a parainfluenza virus; the virus is coxsackievirus; the virus is rhinovirus; the virus is yellow fever virus; the virus is dengue virus; the virus is hepatitis C virus; the virus is Ebola virus; the virus is Marburg virus.

Similarly, in a related aspect, the invention provides a method for the prophylactic treatment of cancer caused by oncoviruses in a human or animal by administering to a human or animal in need of such treatment, a pharmacologically acceptable, therapeutically effective amount of at least one random oligonucleotide of at least 6 nucleotides in length (or another length as described herein), or a formulation or pharmaceutical composition containing such oligonucleotide.

In particular embodiments, the oligonucleotide(s) is as described herein for the present invention, e.g., having a length as described herein; a method of administration as described herein is used; a delivery system as described herein is used.

The term "therapeutically effective amount" refers to an amount that is sufficient to effect a therapeutically or prophylactically significant reduction in production of infectious virus particles when administered to a typical subject of the intended type. In aspects involving administration of an antiviral oligonucleotide to a subject, typically the oligonucleotide, formulation, or composition should be administered in a therapeutically effective amount.

In another aspect, the discovery that non-sequence complementary interactions produce effective antiviral activity provides a method of screening to identify a compound that alters binding of an oligonucleotide to a viral component, such as one or more viral proteins (e.g., extracted or purified from a viral culture of infected host organisms, or produced by recombinant methods). For example, the method can involve determining whether a test compound reduces the binding of oligonucleotide to one or more viral components.

As used herein, the term "screening" refers to assaying a plurality of compounds to determine if they possess a desired property. The plurality of compounds can, for example, be at least 10, 100, 1000, 10,000 or more test compounds.

In particular embodiments, any of a variety of assay formats and detection methods can be used to identify such alteration in binding, e.g., by contacting the oligonucleotide with the viral component(s) in the presence and absence of a compound(s) to be screened (e.g., in separate reactions) and determining whether a difference occurs in binding of the oligo the viral component(s) in the presence of the compound compared to the absence of the compound. The presence of such a difference is indicative that the compound alters the binding of the random oligonucleotide to the viral component. Alternatively, a competitive displacement can be used, such that oligonucleotide is bound to the viral component and displacement by added test compound is determined, or conversely test compound is bound and displacement by added oligonucleotide is determined.

In particular embodiments, the oligonucleotide is as described herein for antiviral oligonucleotides; the oligonucleotide is at least 6, 8, 10, 15, 20, 25, 29, 30, 32, 34, 36, 38, 40, 46, 50, 60, 70, 80, 90, 100, 110, or 120 nucleotides in length or at least another length specified herein for the antiviral oligonucleotides, or is in a range defined by taking any two of the preceding values as inclusive endpoints of the range; the test compound(s) is a small molecule; the test compound has a molecular weight of less than 400, 500, 600, 800, 1000, 1500, 2000, 2500, or 3000 daltons, or is in a range defined by taking any two of the preceding values as inclusive endpoints of the range; the viral extract or component is from a virus as listed herein; at least 100, 1000, 10,000, 20,000, 50,000, or 100,000 compounds are screened; the oligonucleotide has an IC50 of equal to or less than 0.500, 0.200, 0.100, 0.075, 0.05, 0.045, 0.04, 0.035, 0.03, 0.025, 0.02, 0.015, or 0.01 μM.

As used herein, the term "viral component" refers to a product encoded by a virus or produced by infected host cells as a consequence of the viral infection. Such components can include proteins as well as other biomolecules. Such viral components, can, for example, be obtained from viral cultures, infected host organisms, e.g., animals and plants, or can be produced from viral sequences in recombinant systems (prokaryotes and eukaryotes), as well synthetic proteins having amino acid sequences corresponding to viral encoded proteins. The term "viral culture extract" refers to an extract from cells infected by a virus that will include virus-specific products. Similarly, a "viral protein" refers to a virus specific protein, usually encoded by a virus, but can also be encoded at least in part by host sequences as a consequence of the viral infection.

In a related aspect, the invention provides an antiviral compound identified by the preceding method, e.g., a novel antiviral compound.

In a further aspect, the invention provides a method for purifying oligonucleotides binding to at least one viral component from a pool of oligonucleotides by contacting the pool with at least one viral component, e.g., bound to a stationary phase medium, and collecting oligonucleotides that bind to the viral component(s). Generally, the collecting involves displacing the oligonucleotides from the viral component(s). The method can also involve sequencing and/or testing antiviral activity of collected oligonucleotides (i.e., oligonucleotides that bound to viral protein).

In particular embodiments, the bound oligonucleotides of the pool are displaced from the stationary phase medium by any appropriate method, e.g., using an ionic displacer, and displaced oligonucleotides are collected. Typically for the various methods of displacement, the displacement can be performed in increasing stringent manner (e.g., with an increasing concentration of displacing agent, such as a salt concentration, so that there is a stepped or continuous gradient), such that oligonucleotides are displaced generally in order of increased binding affinity. In many cases, a low stringency wash will be performed to remove weakly bound oligonucleotides, and one or more fractions will be collected containing displaced, tighter binding oligonucleotides. In some cases, it will be desired to select fractions that contain very tightly binding oligonucleotides (e.g., oligonucleotides in fractions resulting from displacement by the more stringent displacement conditions) for further use.

Similarly, the invention provides a method for enriching oligonucleotides from a pool of oligonucleotides binding to at least one viral component, by contacting the pool with one or more viral proteins, and amplifying oligonucleotides bound to the viral proteins to provide an enriched oligonucleotide pool. The contacting and amplifying can be performed in multiple rounds, e.g., at least 1, 2, 3, 4, 5, 10, or more additional times using the enriched oligonucleotide pool from the preceding round as the pool of oligonucleotides for the next round. The method can also involve sequencing and testing antiviral activity of oligonucleotides in the enriched oligonucleotide pool following one or more rounds of contacting and amplifying.

The method can involve displacing oligonucleotides from the viral component (e.g., viral protein bound to a solid phase medium) with any of a variety of techniques, such as those described above, e.g., using a displacement agent. As indicated above, it can be advantageous to select the tighter binding oligonucleotides for further use, e.g., in further rounds of binding and amplifying. The method can further involve selecting one or more enriched oligonucleotides, e.g., high affinity oligonucleotides, for further use. In particular embodiments, the selection can include eliminating oligonucleotides that have sequences complementary to host genomic sequences (e.g., human) for a particular virus of interest. Such elimination can involve comparing the oligonucleotide sequence(s) with sequences from the particular host in a sequence database(s), e.g., using a sequence alignment program (e.g., a BLAST search), and eliminating those oligonucleotides that have sequences identical or with a particular level of identity to a host sequence. Eliminating such host complementary sequences and/or selecting one or more oligonucleotides that are not complementary to host sequences can also be done for the other aspects of the present invention.

In the preceding methods for identifying, purifying, or enriching oligonucleotides, the oligonucleotides can be of types as described herein. The above methods are advantageous for identifying, purifying or enriching high affinity oligonucleotides, e.g., from an oligonucleotide randomer preparation.

In a related aspect, the invention concerns an antiviral oligonucleotide preparation that includes one or more oligonucleotides identified using a method of any of the preceding methods for identifying, obtaining, or purifying antiviral oligonucleotides from an initial oligonucleotide pool, where the oligonucleotides in the oligonucleotide preparation exhibit higher mean binding affinity with one or more viral proteins than the mean binding affinity of oligonucleotides in the initial oligonucleotide pool.

In particular embodiments, the mean binding affinity of the oligonucleotides is at least two-fold, 3-fold, 5-fold, 10-fold, 20-fold, 50-fold, or 100-fold greater than the mean binding affinity of oligonucleotides in the initial oligonucleotide pool, or even more; the median of binding affinity is at least two-fold, 3-fold, 5-fold, 10-fold, 20-fold, 50-fold, or 100-fold greater relative to the median of the binding affinity of the initial oligo pool, where median refers to the middle value.

In yet another aspect, the invention provides an antiviral polymer mix that includes at least one antiviral oligonucleotide and at least one non-nucleotide antiviral polymer. In particular embodiments, the oligonucleotide is as described herein for antiviral oligonucleotides and/or the antiviral polymer is as described herein or otherwise known in the art or subsequently identified.

In yet another aspect, the invention provides an oligonucleotide randomer, where the randomer is at least 6 nucleotides in length. In particular embodiments the randomer has a length as specified above for antiviral oligonucleotides; the randomer includes at least one phosphorothioate linkage, the randomer includes at least one phosphorodithioate linkage or other modification as listed herein; the randomer oligonucleotides include at least one non-randomer segment (such as a segment complementary to a selected virus nucleic acid sequence), which can have a length as specified above for oligonucleotides; the randomer is in a preparation or pool of preparations containing at least 5, 10, 15, 20, 50, 100, 200, 500, or 700 micromol, 1, 5, 7, 10, 20, 50, 100, 200, 500, or 700 mmol, or 1 mole of randomer, or a range defined by taking any two different values from the preceding as inclusive end points, or is synthesized at one of the listed scales or scale ranges.

Likewise, the invention provides a method for preparing antiviral randomers, by synthesizing at least one randomer, e.g., a randomer as described above.

As indicated above, for any aspect involving a viral infection or risk of viral infection or targeting to a particular virus, in particular embodiments the virus is as listed above.

The expression "human and animal viruses" is intended to include, without limitation, DNA and RNA viruses in general. DNA viruses include, for example, parvoviridae, papovaviridae, adenoviridae, herpesviridae, poxviridae, hepadnaviridae, and papillomaviridae. RNA viruses include, for example, arenaviridae, bunyaviridae, calciviridae, coronaviridae, filoviridae, flaviridae, orthomyxoviridae, paramyxoviridae, picornaviridae, reoviridae, rhabdoviridae, retroviridae, or togaviridae.

In connection with modifying characteristics of an oligonucleotide by linking or conjugating with another molecule or moiety, the modifications in the characteristics are evaluated relative to the same oligonucleotide without the linked or conjugated molecule or moiety.

Additional embodiments will be apparent from the Detailed Description and from the claims.

FIG. 11. Plaque reduction assay conducted in VERO cells using HSV-1 (strain KOS). A PS-ODN having 2-O methyl modifications to the 4 ribose sugars at each end of the oligo (REP 2024, [a]); a ODN having methylphosphonate modifications to the 4 ester linkages at each end of the oligo (REP 2026 [b]); and RNA PS-ODNs 20 bases (REP2059 [c]) and 30 bases (REP2060 [d]) in length were tested in increasing concentrations. $IC_{50}$ values calculated from linear regressions are reported in each graph.

Figure 12A:
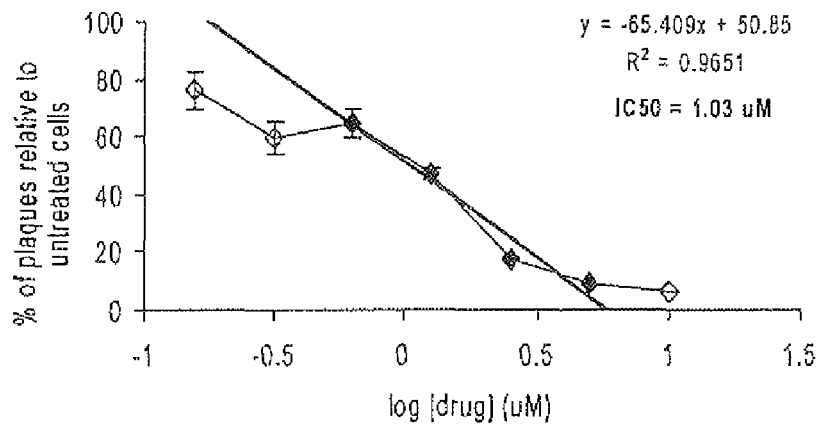
Figure 12B:
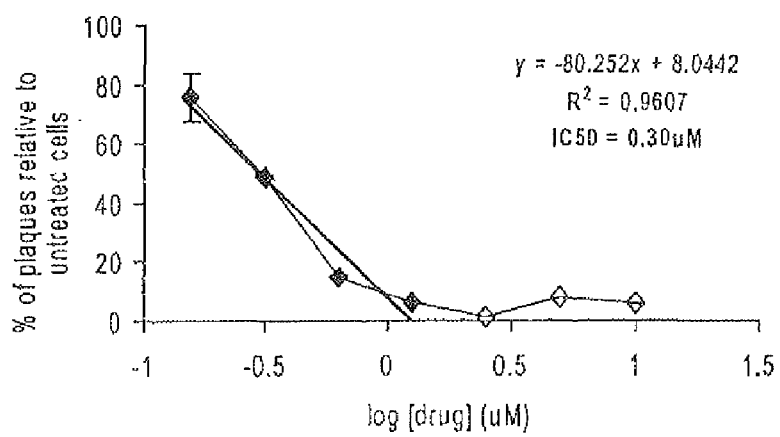
Figure 12C:
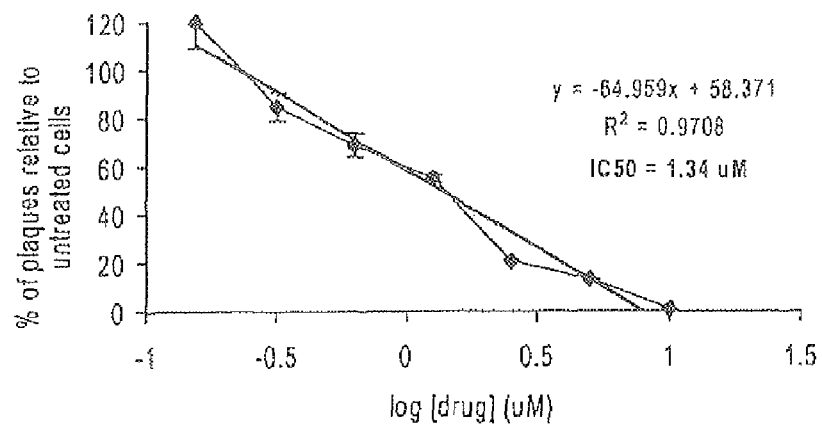

FIG. 12. Plaque reduction assay conducted in human fibroblast cells using HSV-2 (strain MS2). Infected cells are treated with increasing concentrations of REP 1001 (a), REP 2001 (b) or REP 3007 (c). $IC_{50}$ values calculated from linear regressions are reported in each graph.

Figure 13:
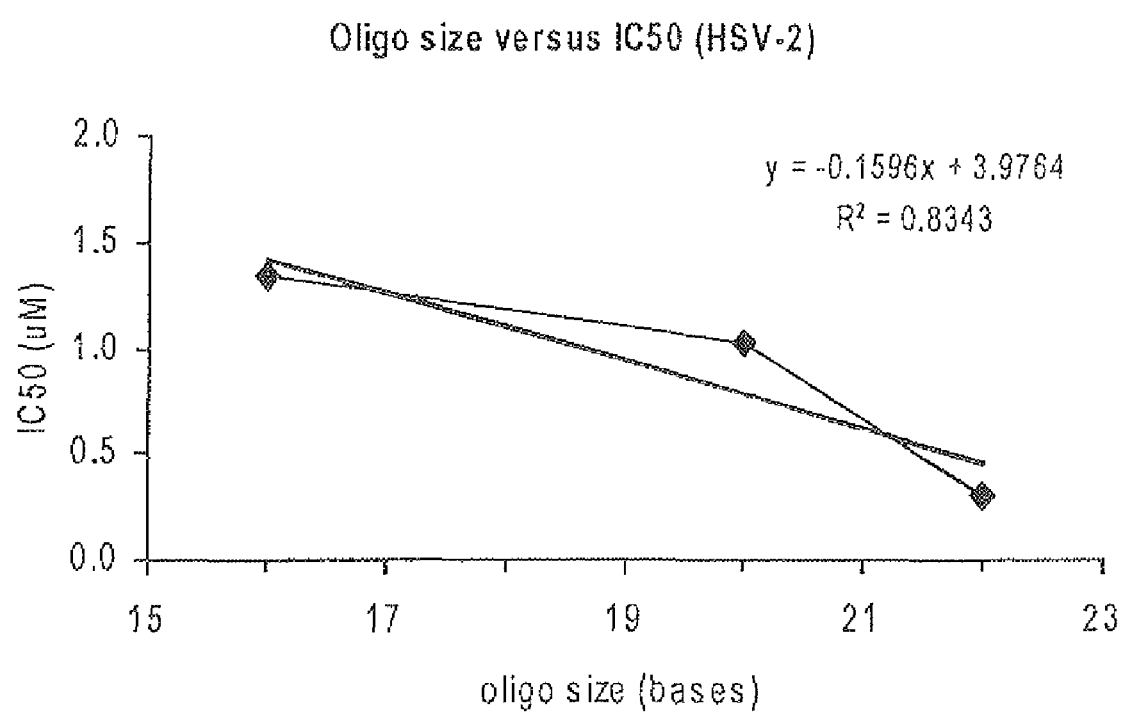
Figure 14A:
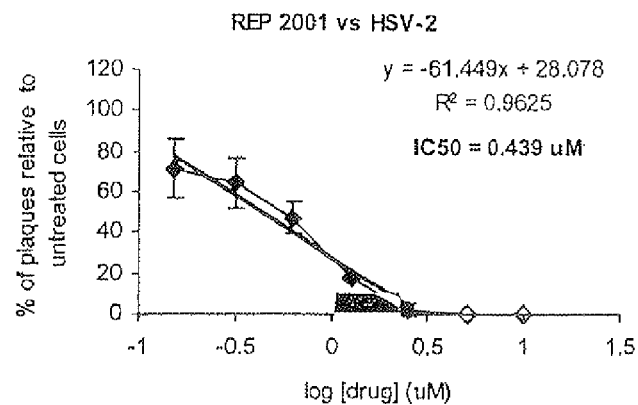
Figure 14B:
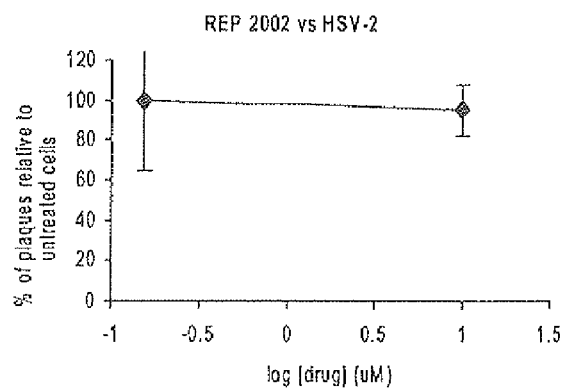
Figure 14C:
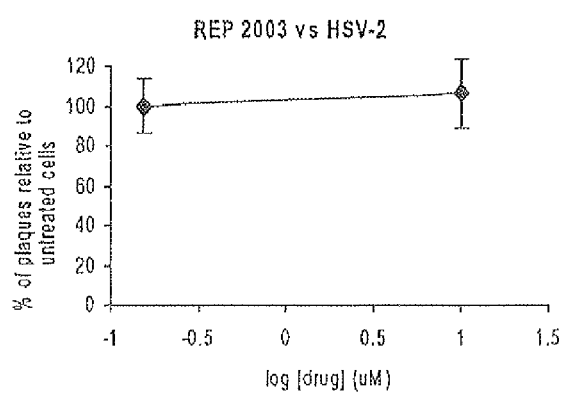
Figure 14D:
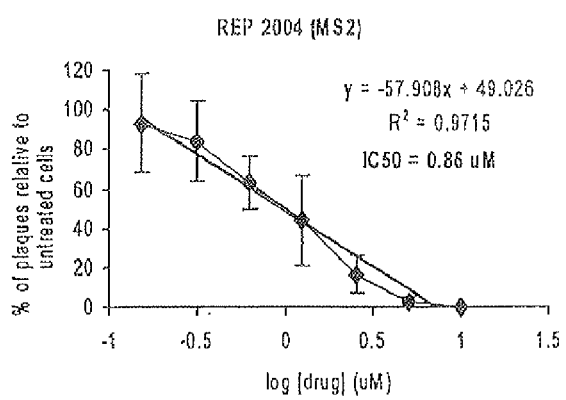
Figure 14E:
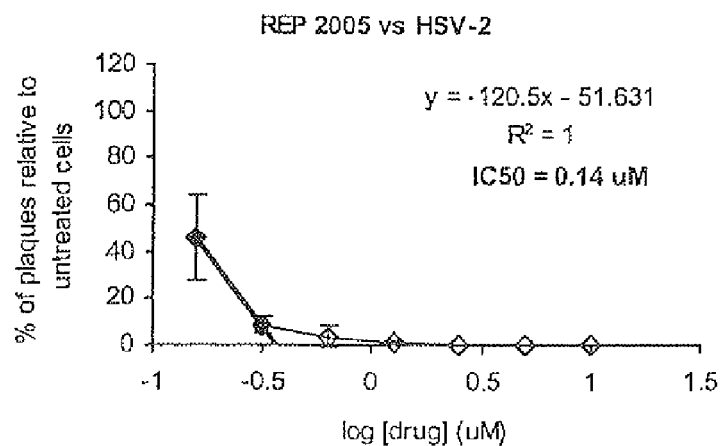
Figure 14F:
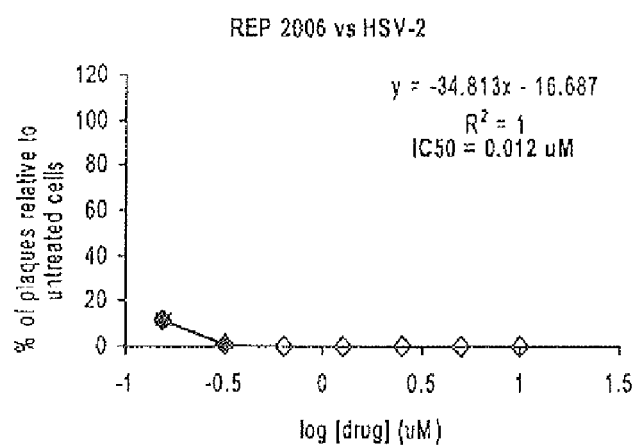
Figure 14G:
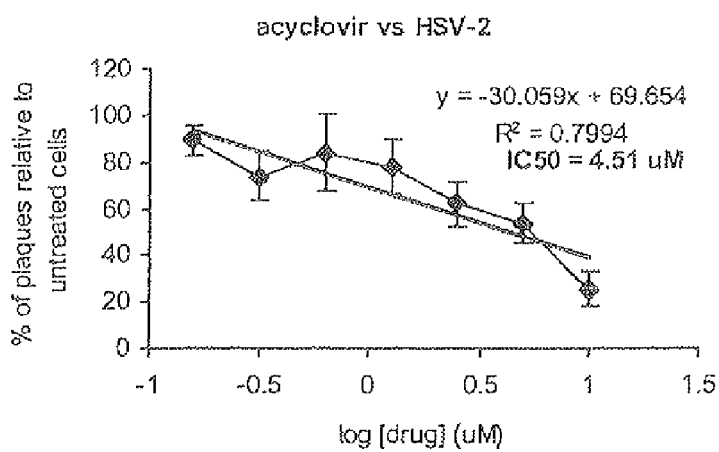

FIG. 13. Relationship between PS-ODN size and $IC_{50}$ against HSV-2. $IC_{50}$ values from FIG. 12 are plotted against the specific size of each PS-ODN tested in FIG. 12.

FIG. 14. Plaque reduction assay conducted in VERO cells using HSV-2 (strain MS2). Infected cells are treated with increasing concentrations of REP 2001 (a), REP 2002 (b) or REP 2003 (c), REP 2004 (d), REP 2005 (e), REP 2006 (f) and acyclovir (g). $IC_{50}$ values calculated from linear regressions are reported in each graph.

Figure 15:
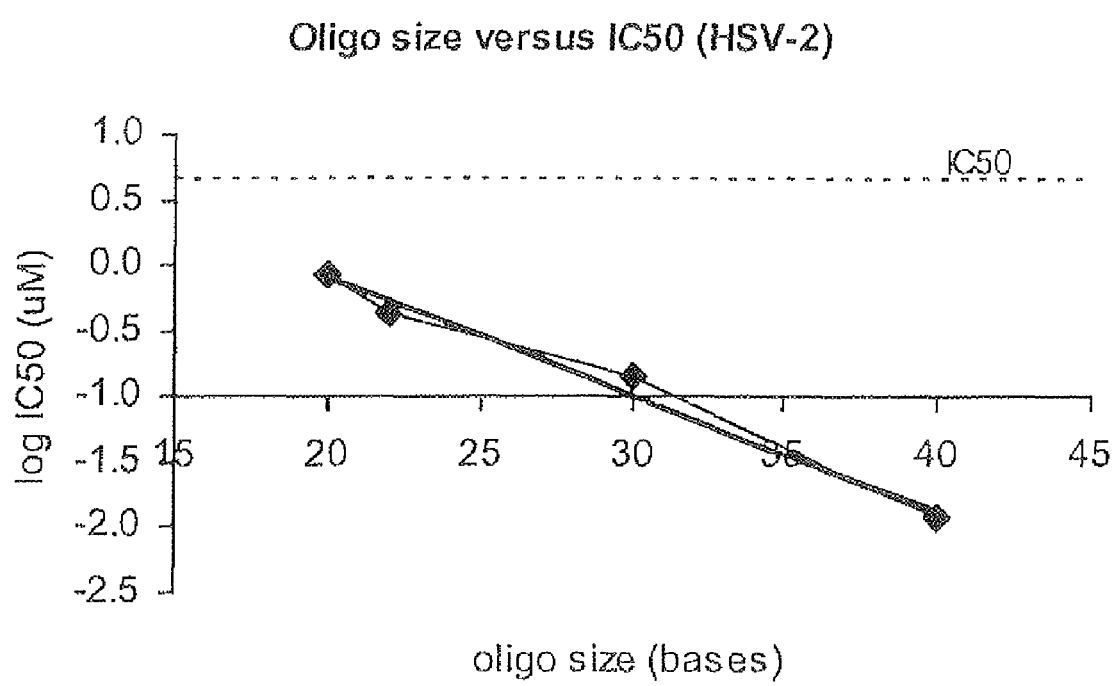

FIG. 15. Relationship between PS-ODN size and $IC_{50}$ against HSV-2. $IC_{50}$ values from FIG. 14 are plotted against the specific size of each PS-ODN tested in FIG. 14 which showed anti-HSV-2 activity. The $IC_{50}$ for acyclovir is provided for reference to a clinical correlate.

Figure 16A:
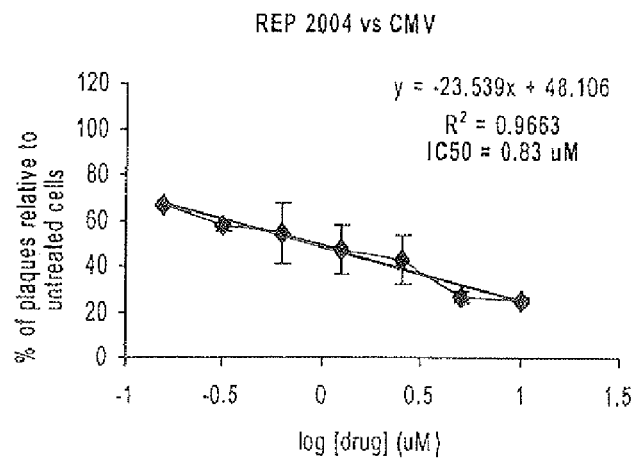
Figure 16B:
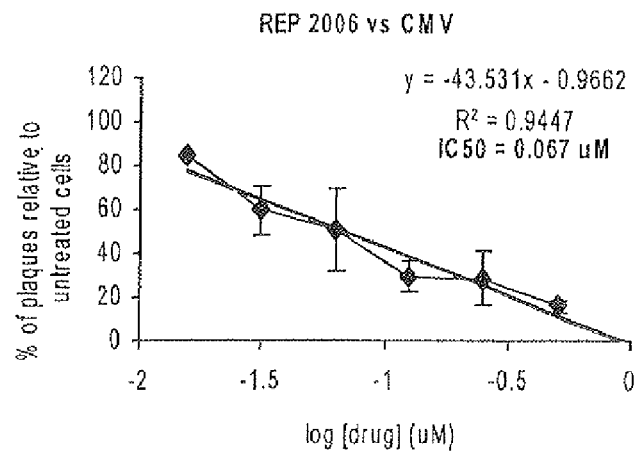
Figure 16C:
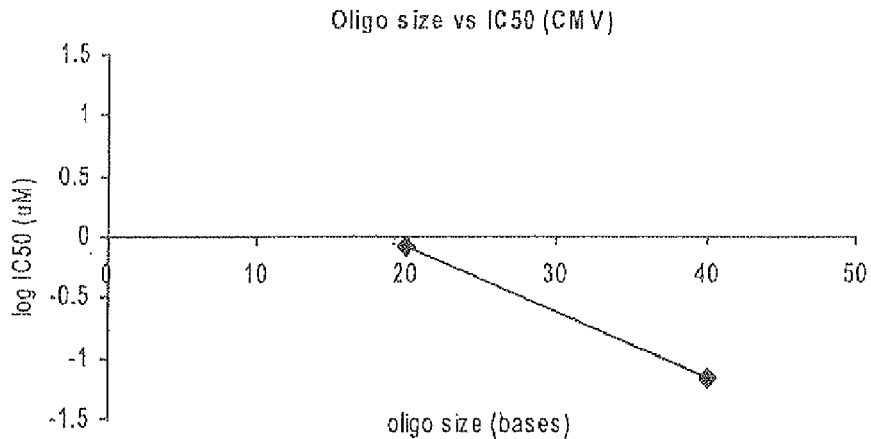
Figure 17A:
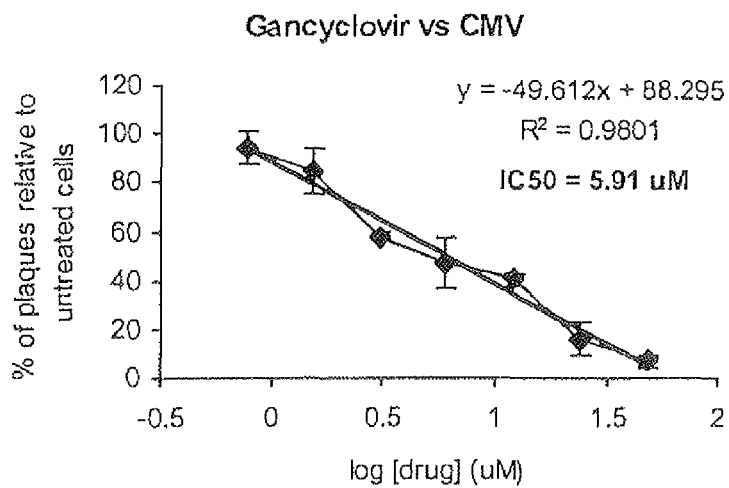
Figure 17B:
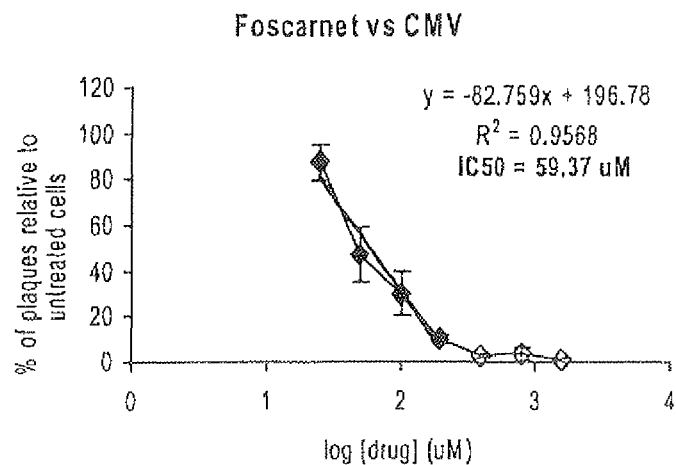
Figure 17C:
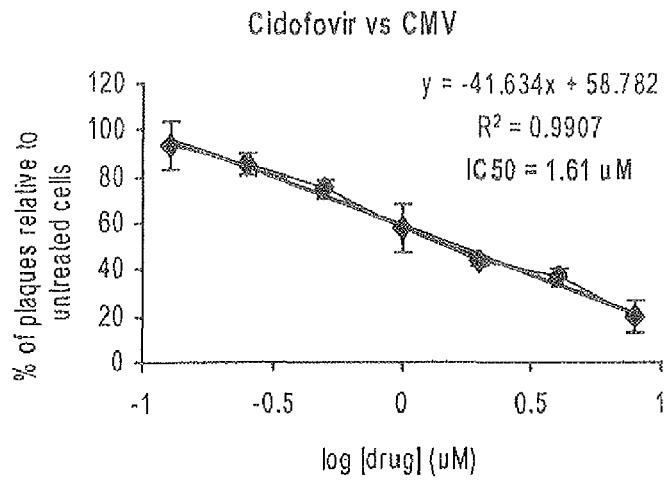
Figure 17D:
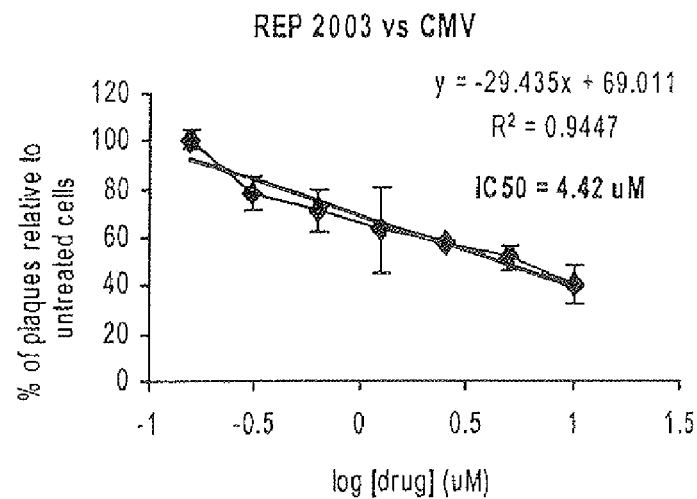
Figure 17E:
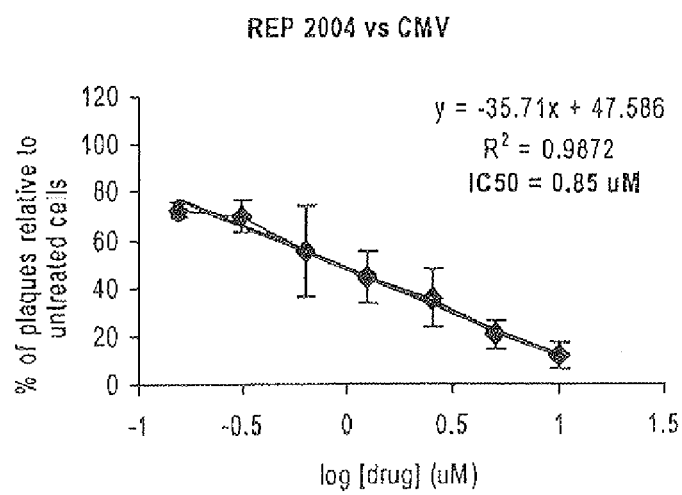
Figure 17F:
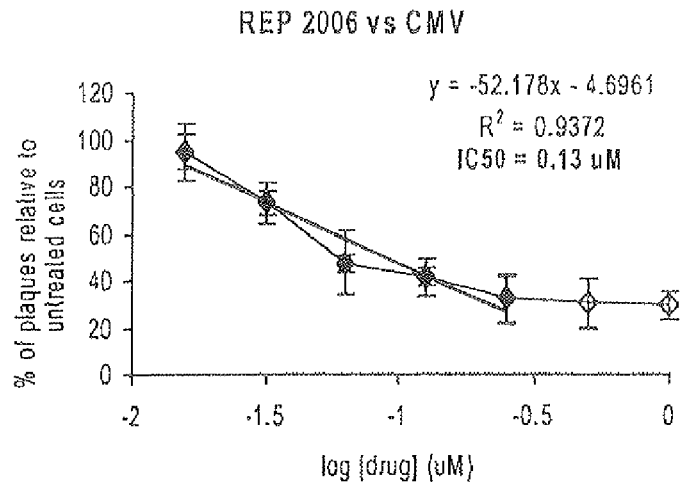
Figure 17G:
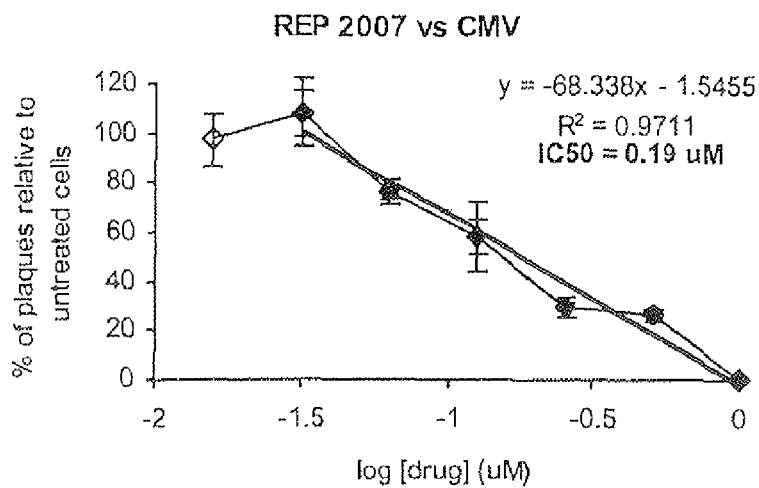
Figure 17H:
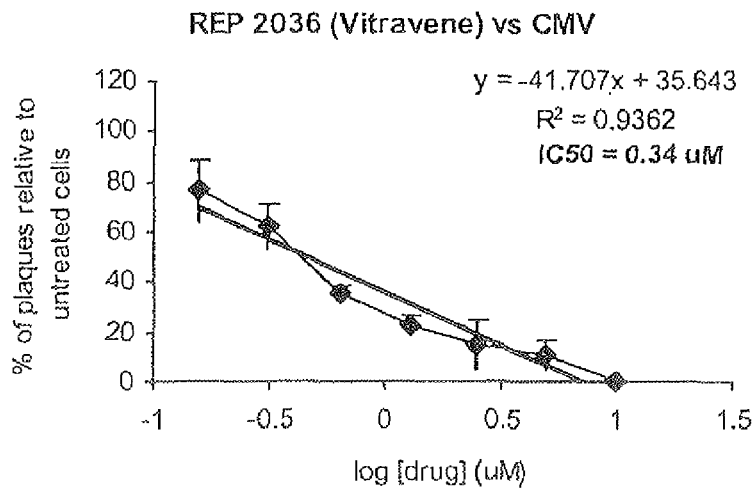
Figure 17I:
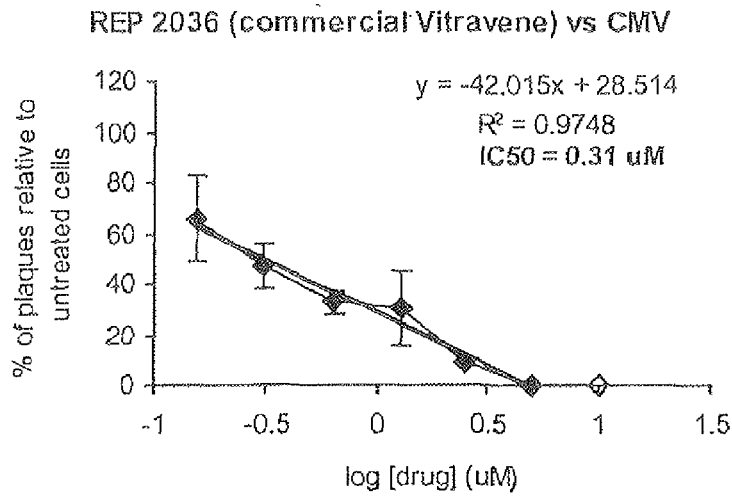

FIG. 16. Plaque reduction assay conducted in VERO cells using CMV (strain AD169). Infected cells are treated with increasing concentrations of REP 2004 (a) or REP 2006 (b). $IC_{50}$ values calculated from linear regressions are reported in each graph. The relationship between PS-ODN size and $IC_{50}$ against CMV is plotted in (c). $IC_{50}$ values from figure (a) and (b) are plotted against the specific size of each PS-ODN tested.

FIG. 17. Plaque reduction assay conducted in VERO cells using CMV (strain AD169). Three clinical CMV therapies were tested: Gancyclovir (a), Foscarnet (b) and Cidofovir (c). A broad range of PS-ODN randomer sizes were also tested in increasing concentrations; REP 2003 (d), REP 2004 (e), REP 2006 (f) and REP 2007 (g). Finally, REP 2036 (Vitravene) was tested as synthesized in house (h) and as commercially available (i). $IC_{50}$ values calculated from linear regressions are reported in each graph.

Figure 18:
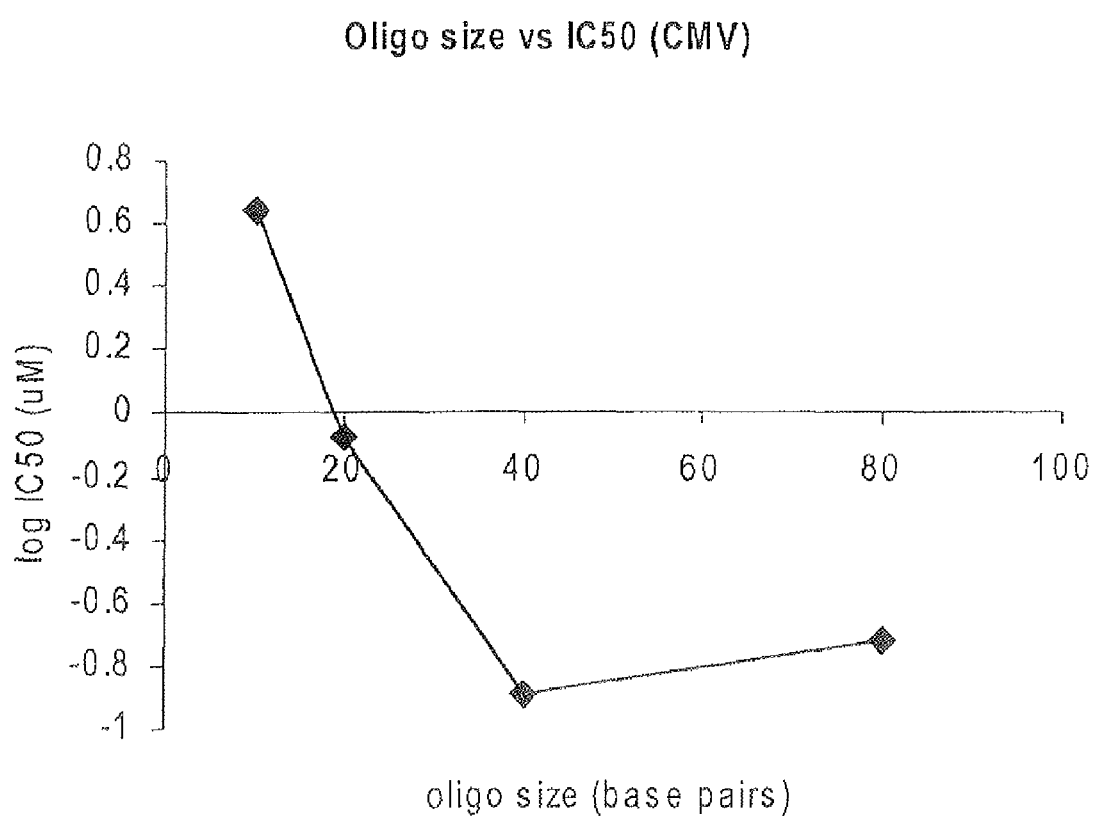
Figure 19A:
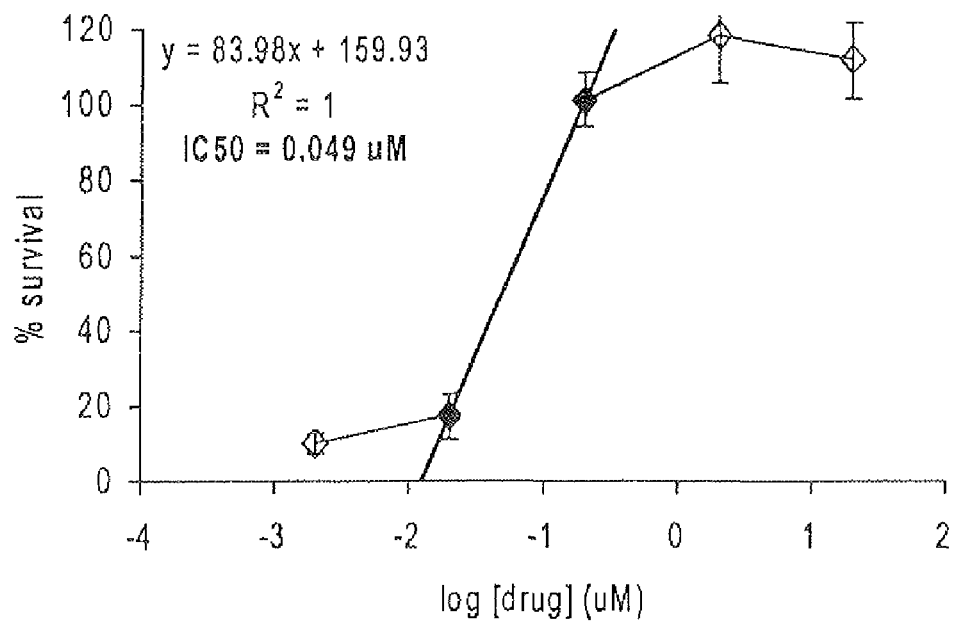
Figure 19B:
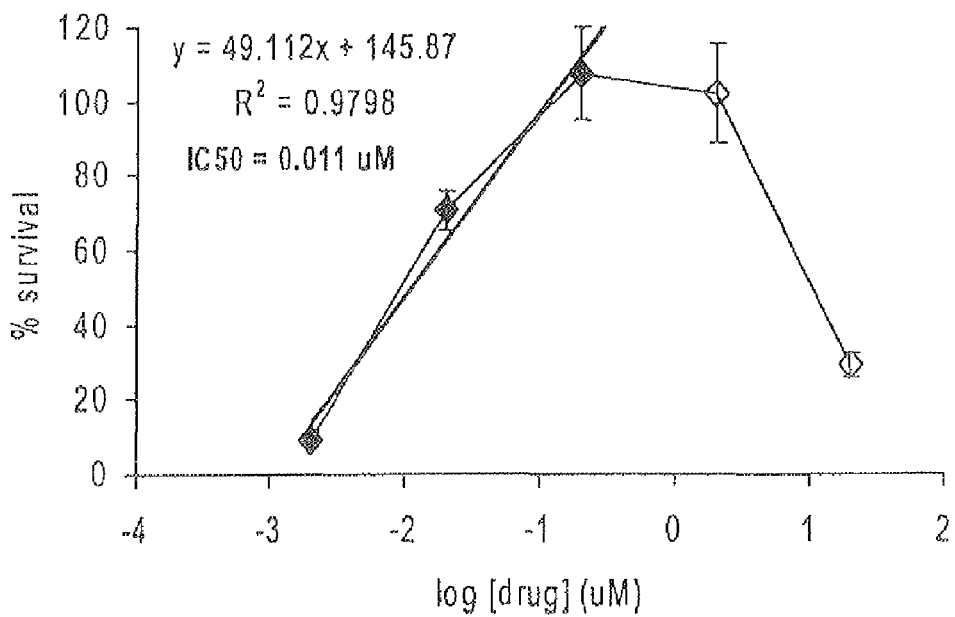
Figure 19C:
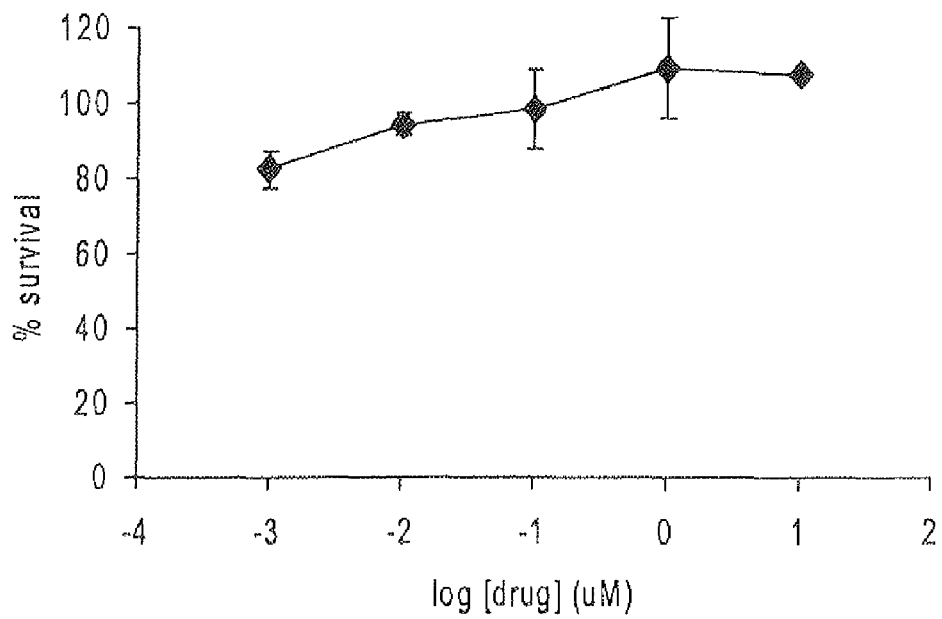
Figure 19D:
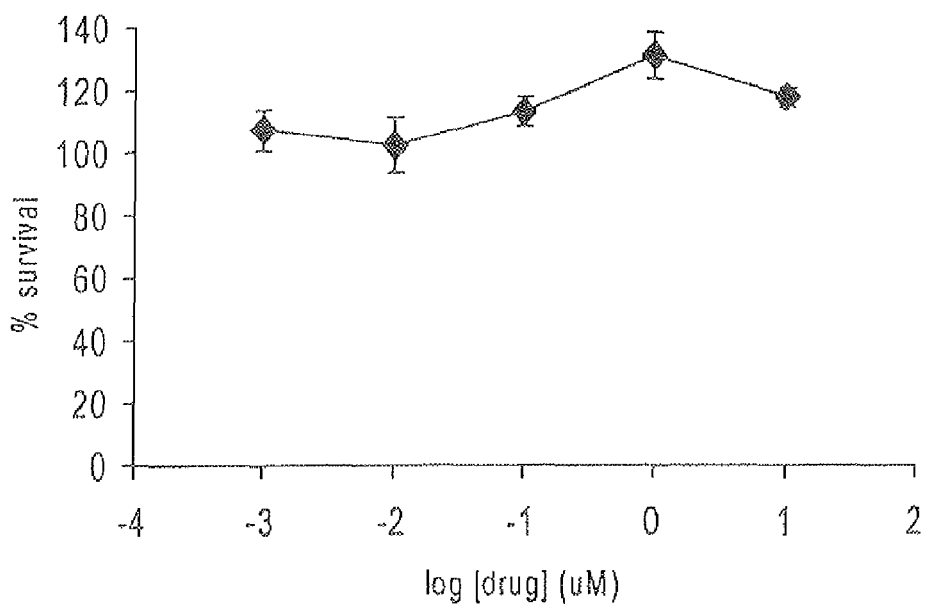

FIG. 18. Relationship between PS-ODN size and $IC_{50}$ against CMV. $IC_{50}$ values from FIG. 17 are plotted against the specific size of each PS-ODN tested in FIG. 17 which showed anti-CMV activity.

FIG. 19. CPE assay conducted in MT4 cells using HIV-1 (strain NL4-3). Infected cells are treated with increasing concentrations of REP 2004 (a) or REP 2006 (b). $IC_{50}$ values calculated from linear regressions are reported in each graph. Cytotoxicity profiles in uninfected MT4 cells are presented for REP 2004 (c) and REP 2006 (d).

Figure 1A:
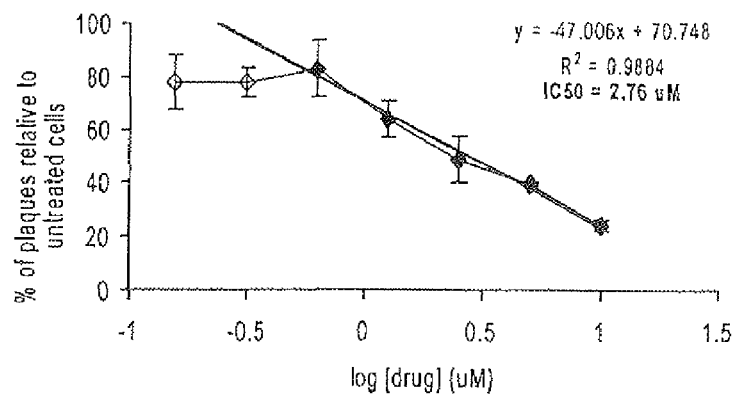
FIG. 1. Plaque reduction assay conducted in VERO cells using HSV-1 (strain KOS). Infected cells are treated with increasing concentrations of REP 1001 (a), REP 2001 (b) or REP 3007 (c). $IC_{50}$ values calculated from linear regressions are reported in each graph.
Figure 1B:
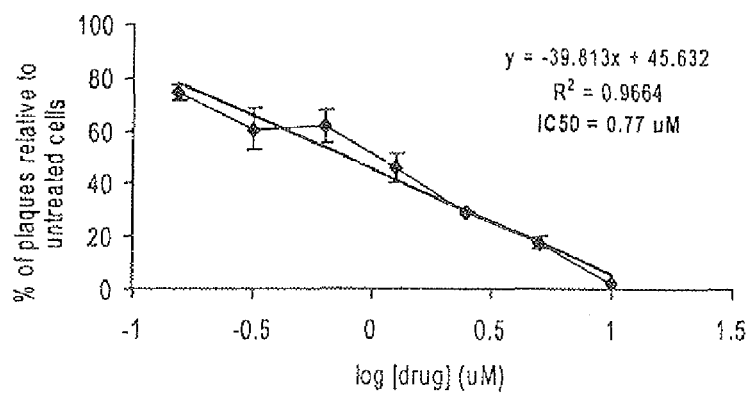
Figure 1C:
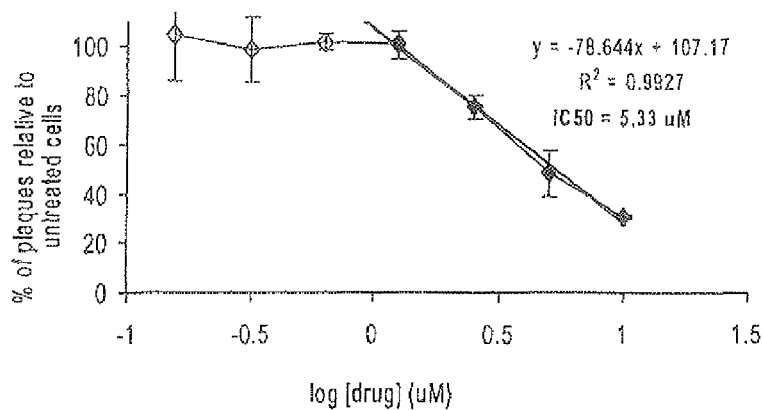
Figure 20:
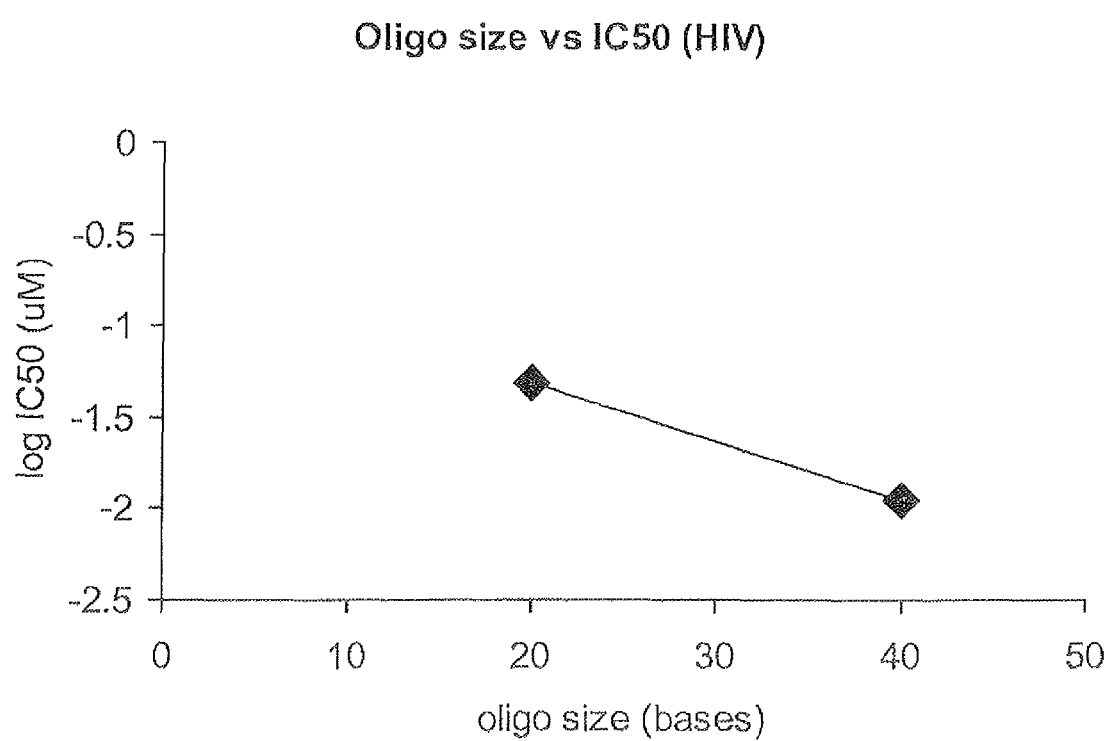
Figure 21A:
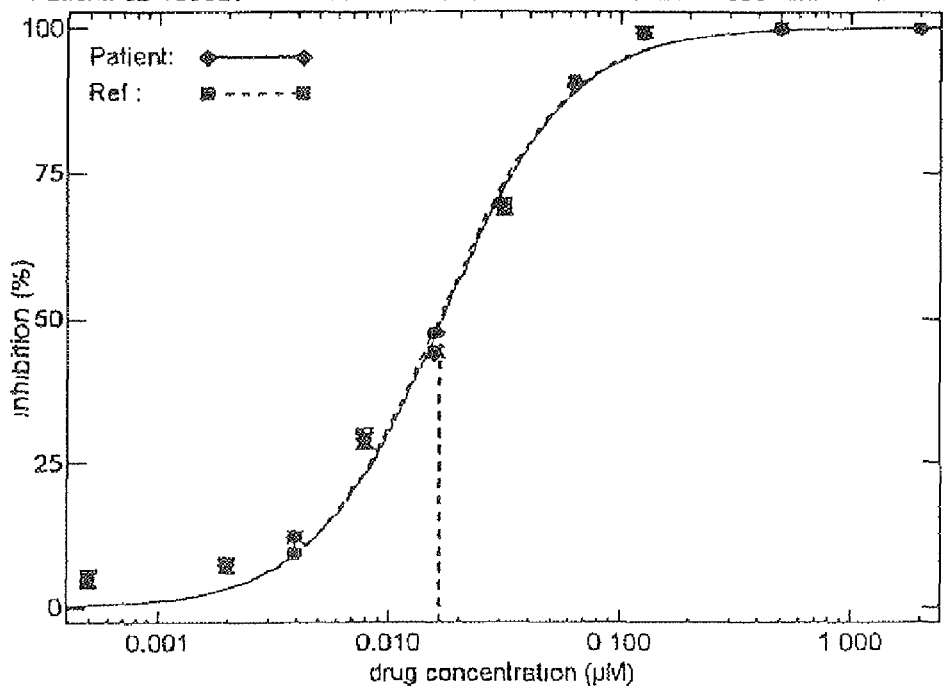
Figure 21B:
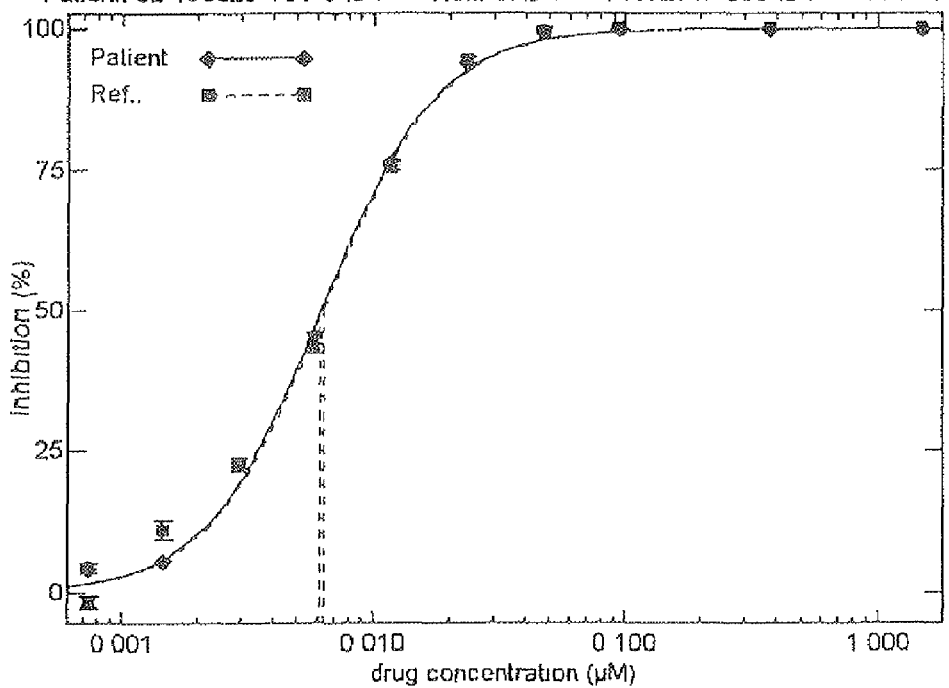
Figure 21C:
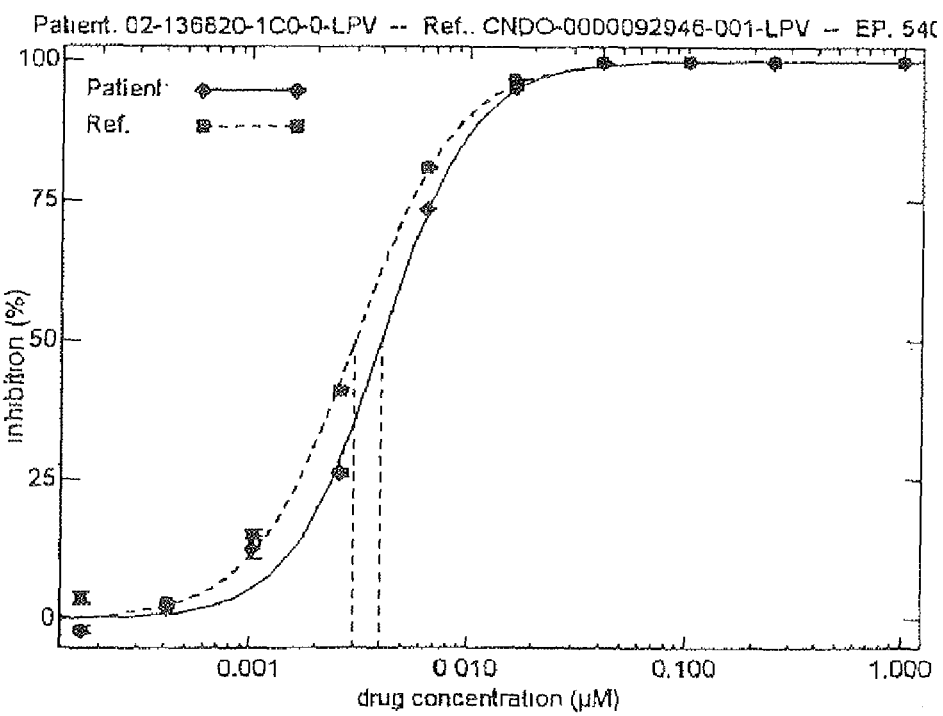
Figure 21D:
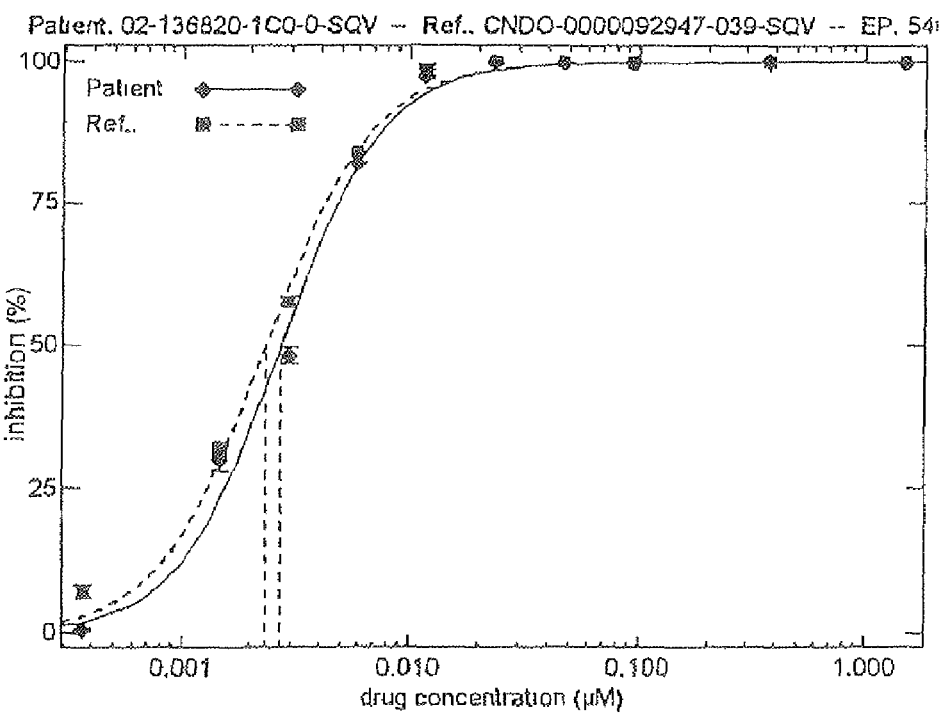
Figure 21E:
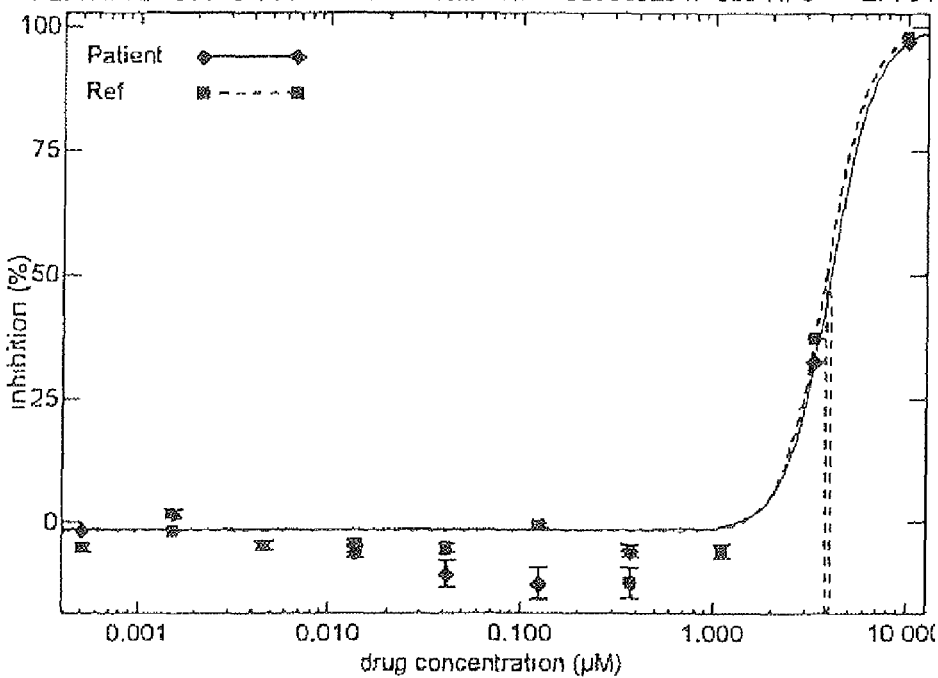
Figure 21F:
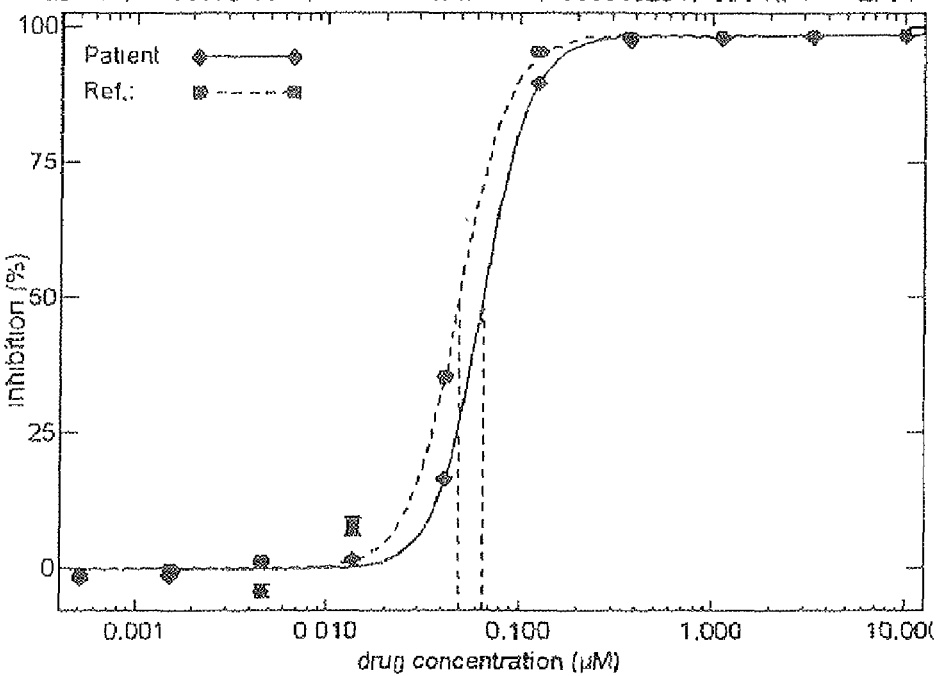
Figure 21G:
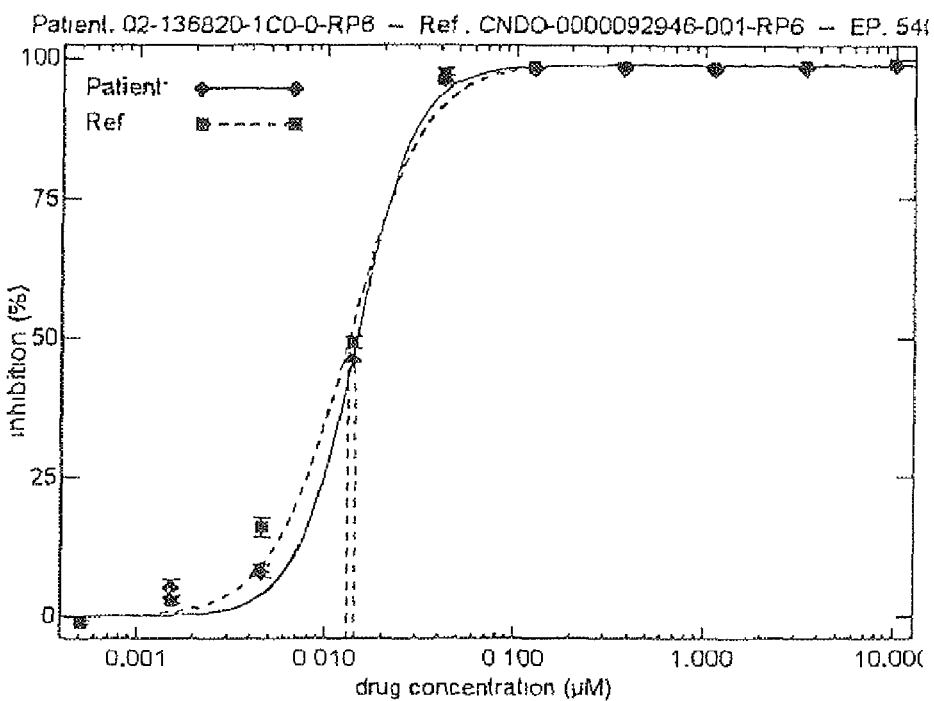
Figure 21H:
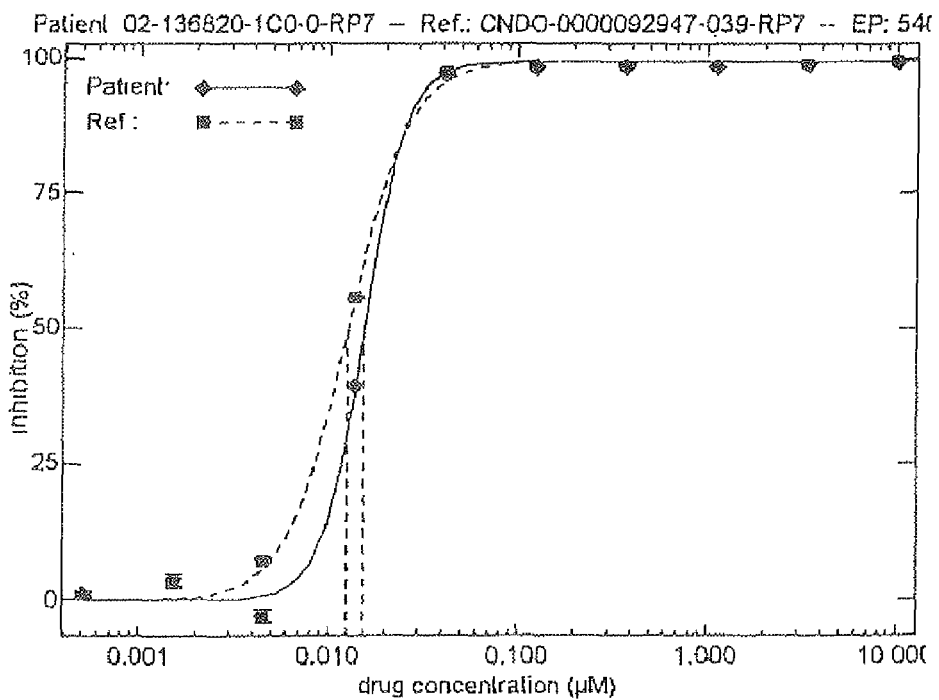

FIG. 20. Relationship between PS-ODN size and $IC_{50}$ against HIV-1. $IC_{50}$ values from FIG. 1 are plotted against the specific size of each PS-ODN tested in FIG. 1.

FIG. 21. Replication assay conducted in 293A cells using recombinant wild type HIV-1 NL4-3 (strain CNDO). Infected cells are treated with increasing concentrations of Amprenavir (a), Indinavir (b), Lopinavir (c), Saquinavir (d), REP 2003 (e), REP 2004 (f), REP 2006 (g) and REP 2007 (h). Both curves (black and dotted lines) represent dose response curves against strain CNDO.

Figures 22A, 22B:
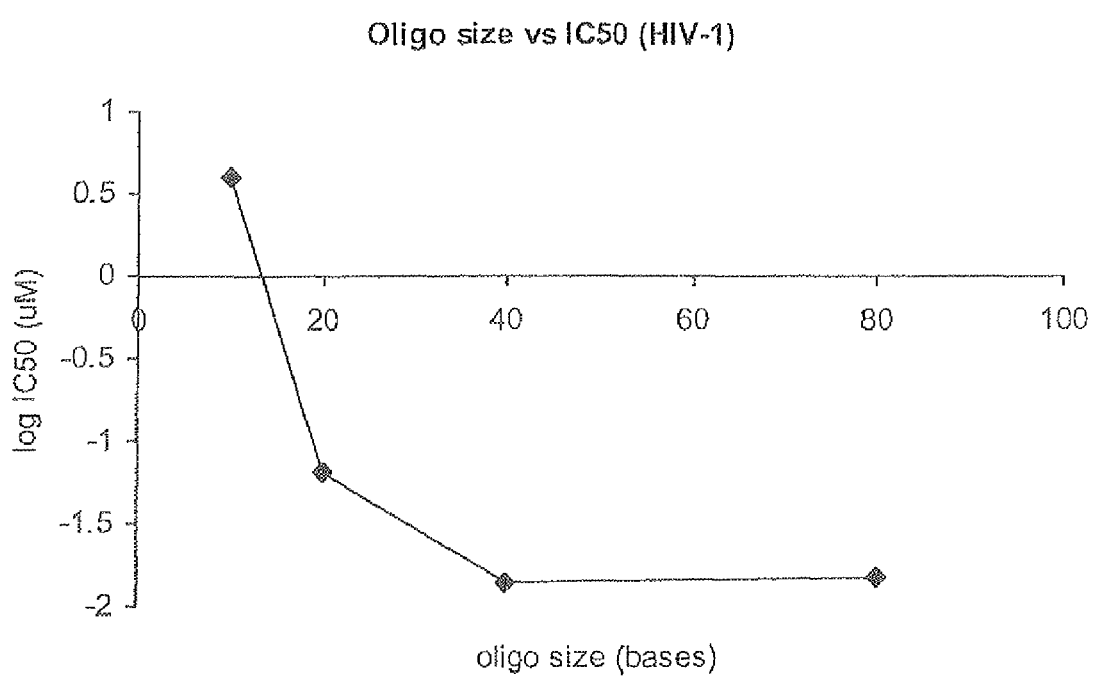
Figure 23A:
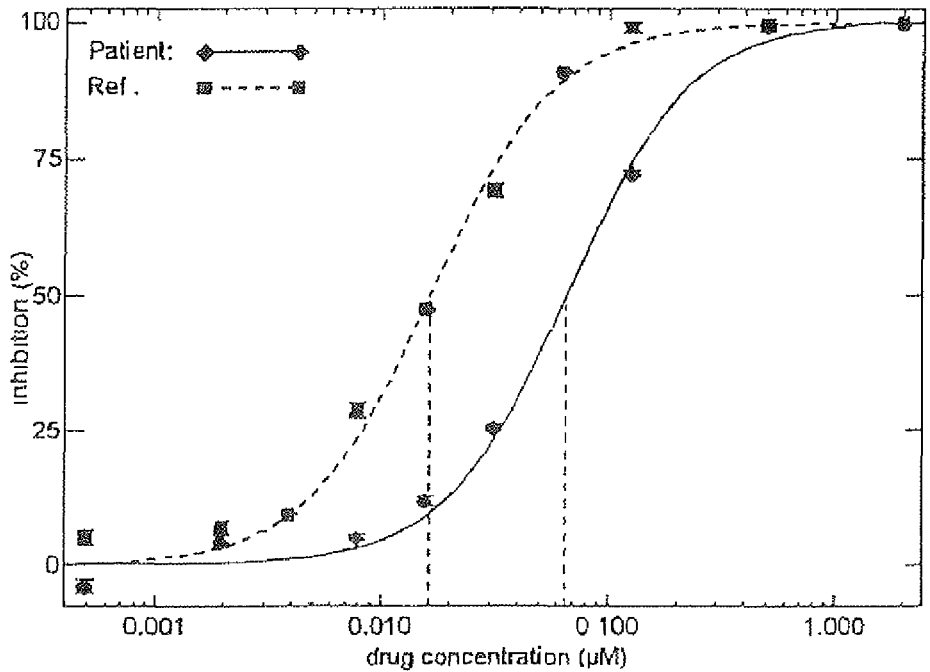
Figure 23B:
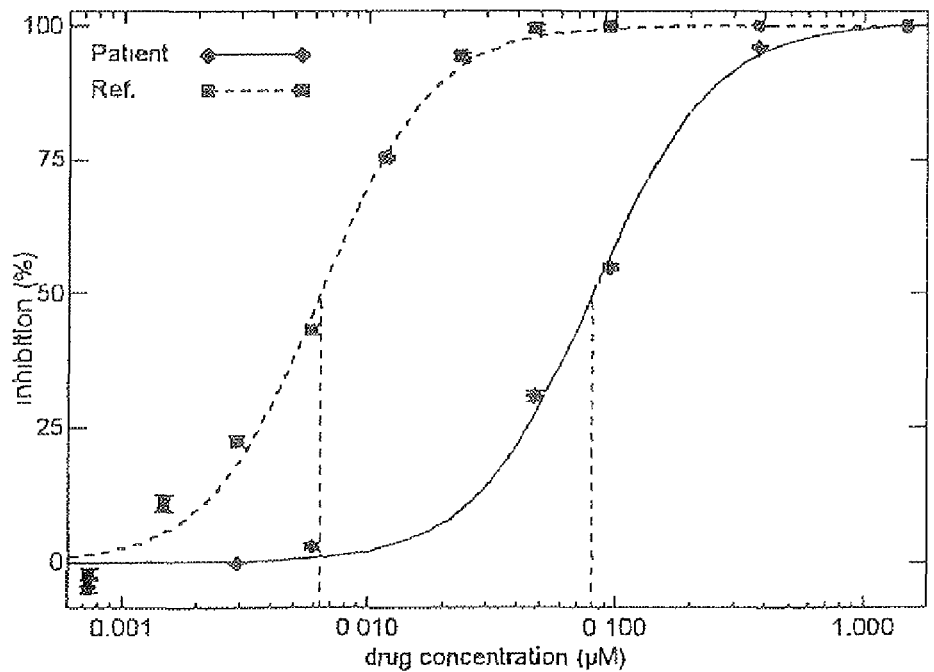
Figure 23C:
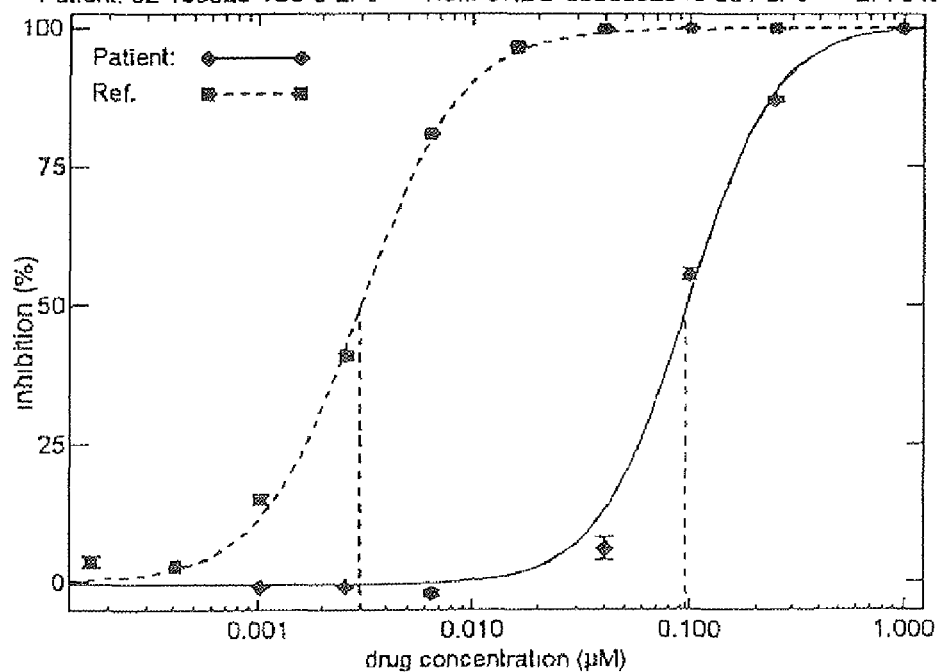
Figure 23D:
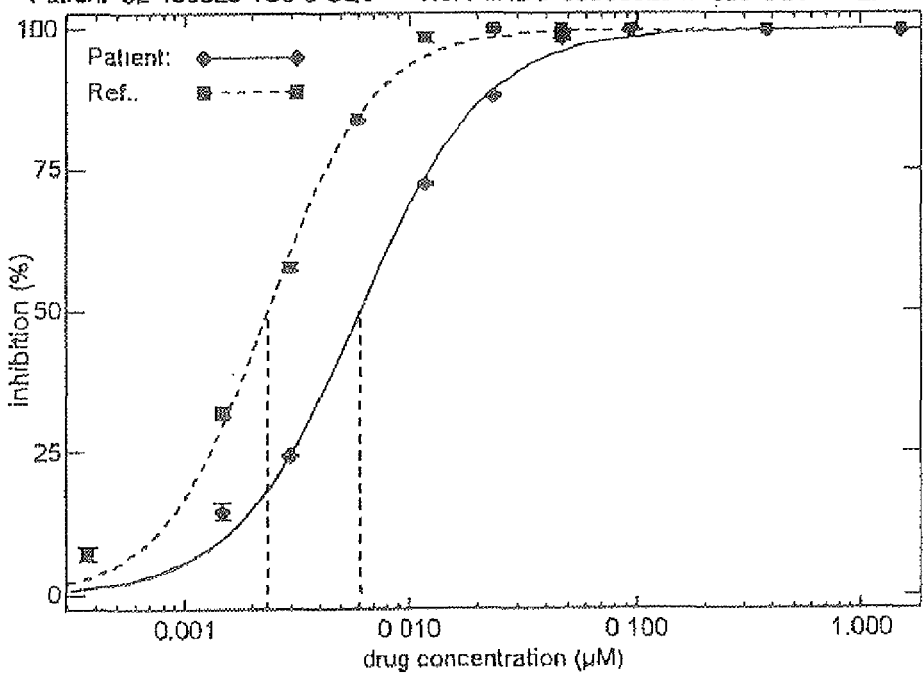
Figure 23E:
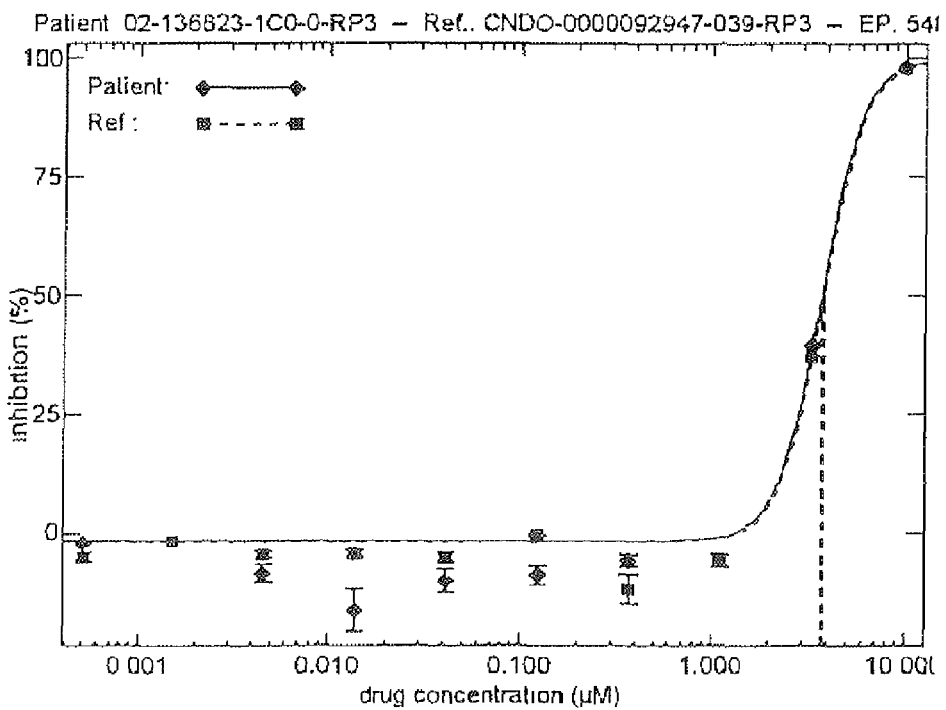
Figure 23F:
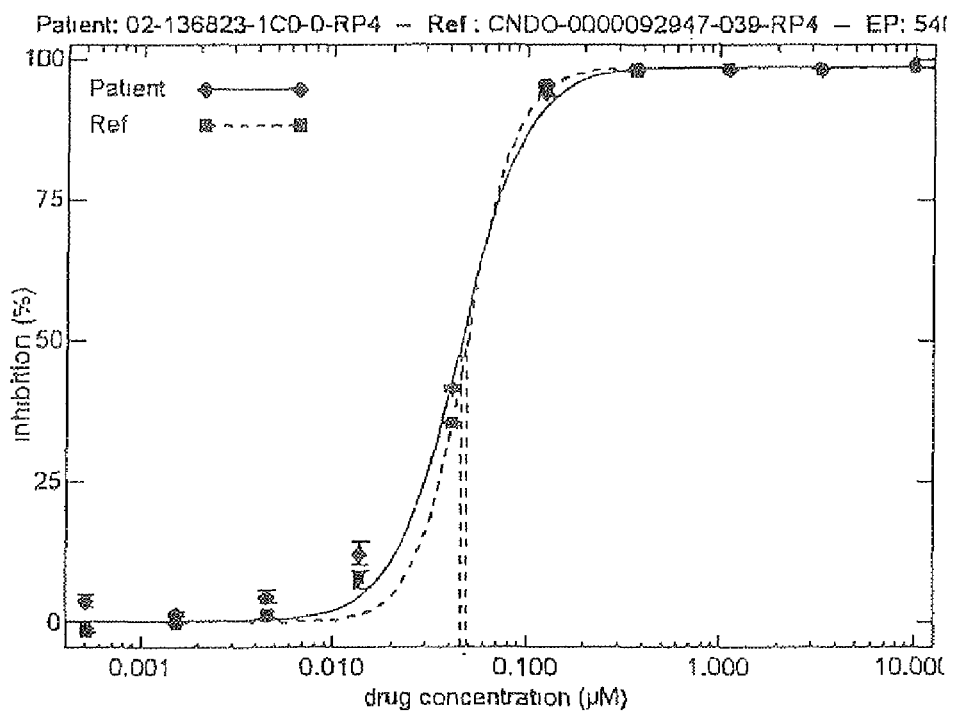
Figure 23G:
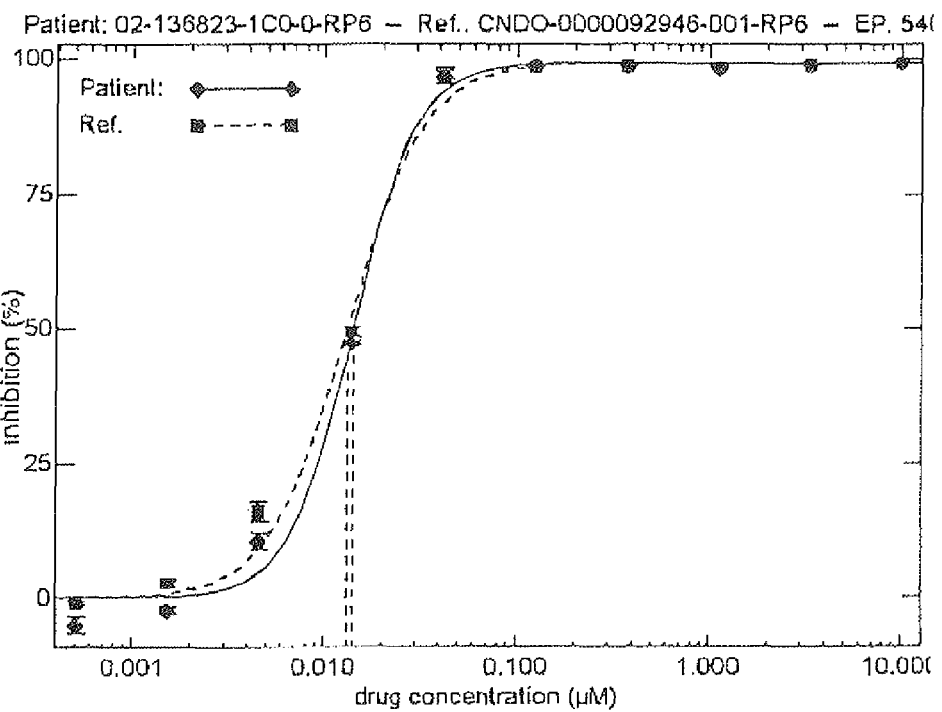
Figure 23H:
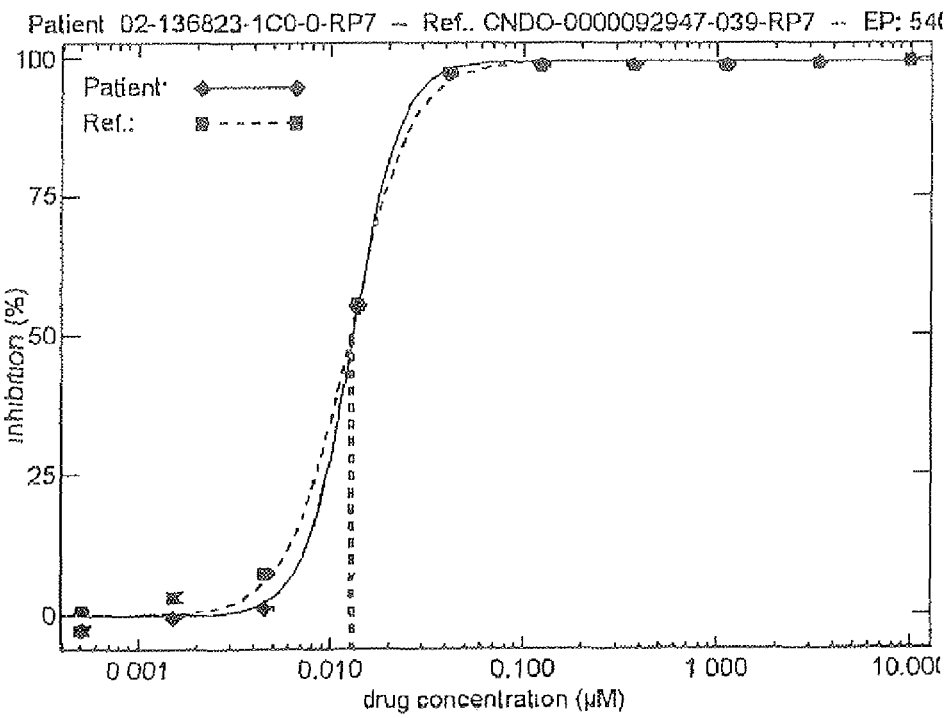
Figure 25A:
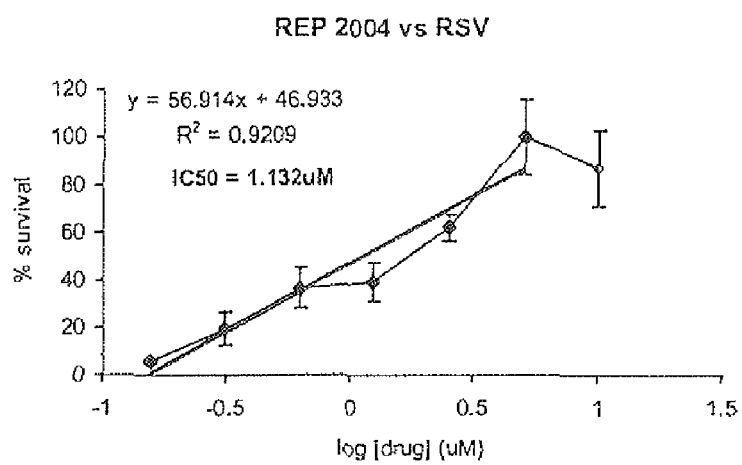
Figure 25B:
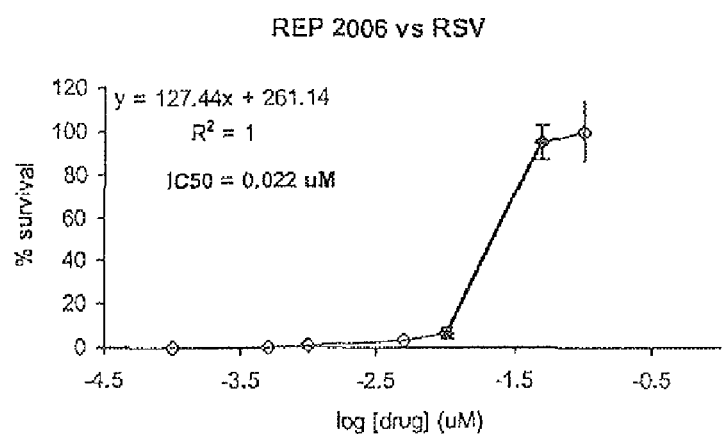
Figure 25C:
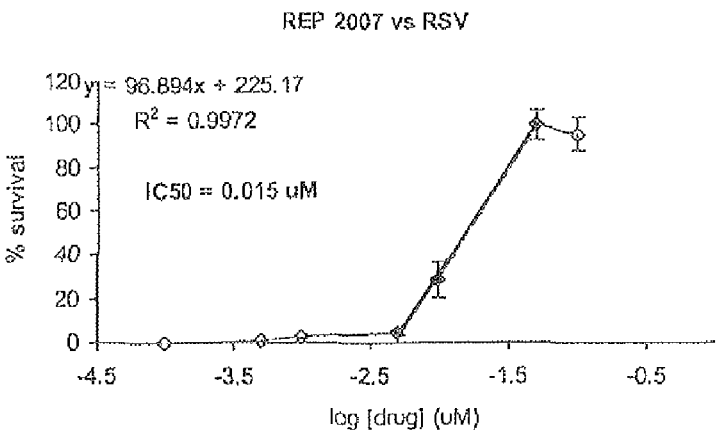
Figure 25D:
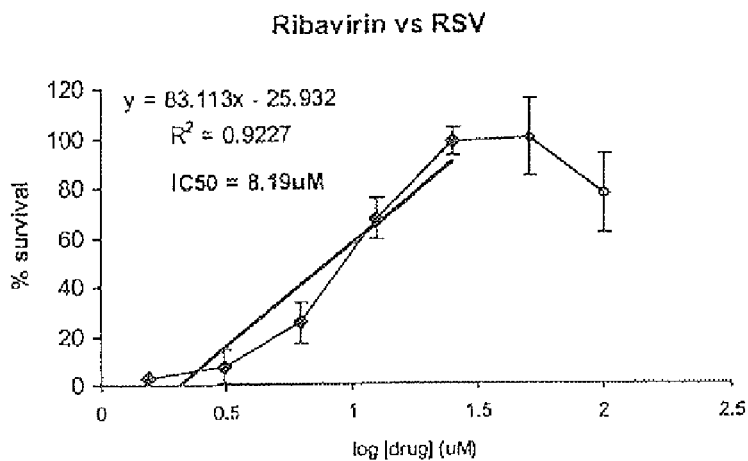
Figure 25E:
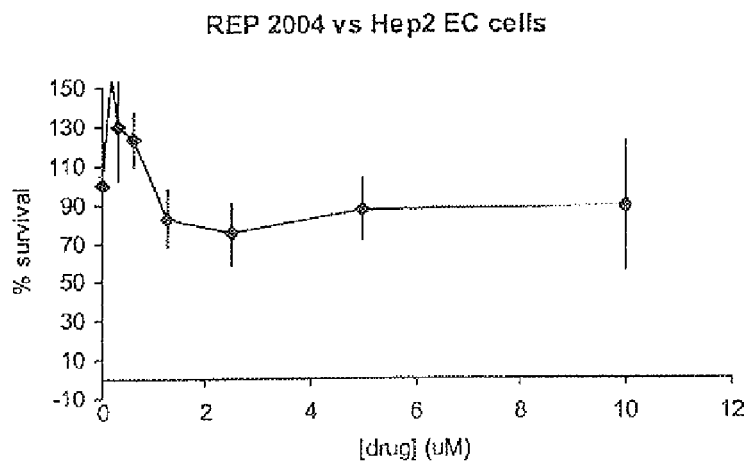
Figure 25F:
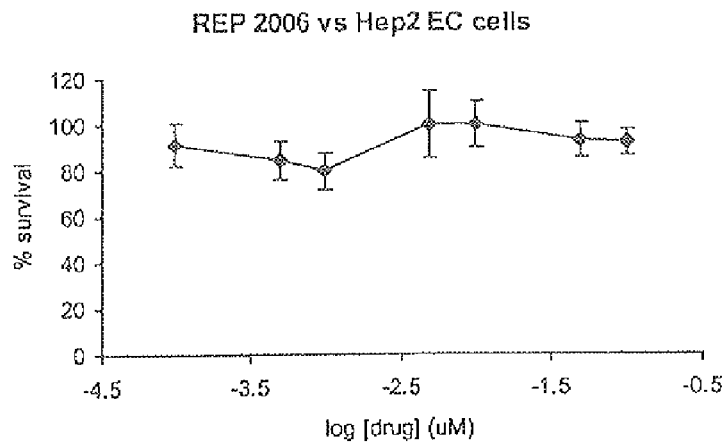
Figure 25G:
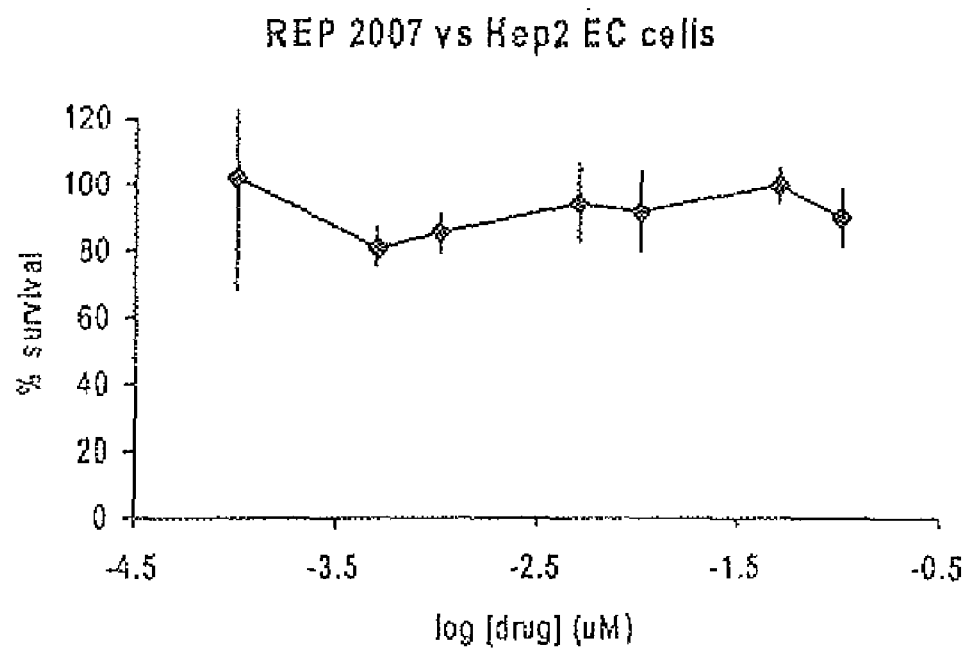
Figure 25H:
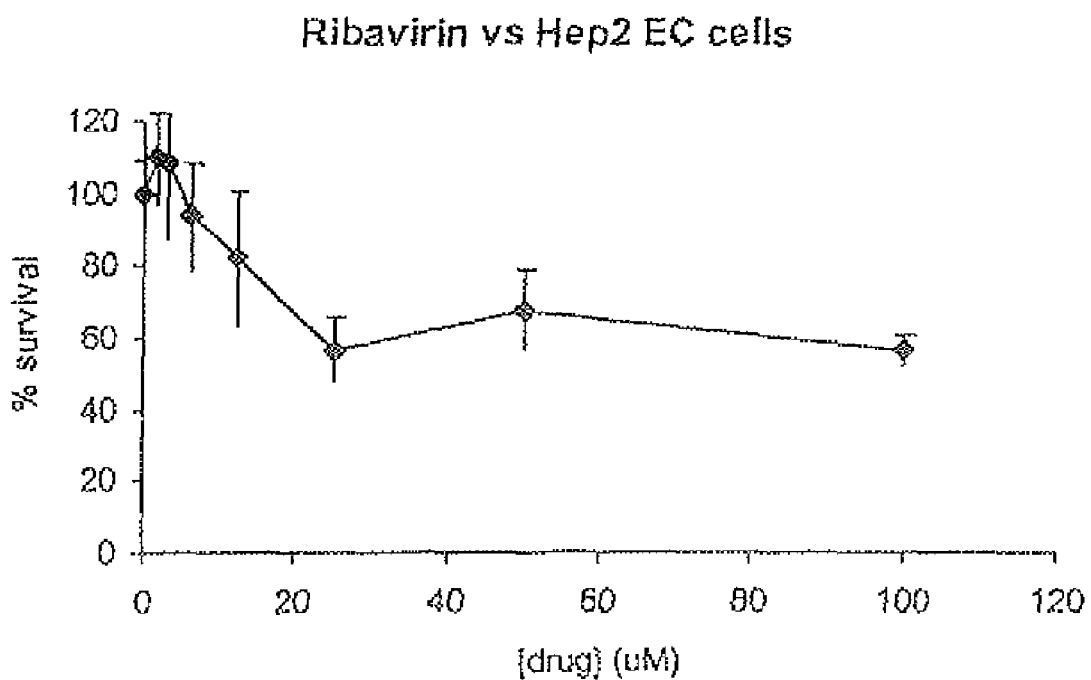

FIG. 22. (a) $IC_{50}$ values from FIG. 21 and (b), relationship between PS-ODN size and $IC_{50}$ against recombinant HIV-1. $IC_{50}$ values from (a) are plotted against the specific size of each PS-ODN tested in FIG. 21.

FIG. 23. Replication assay conducted in 293A cells using recombinant multi drug resistant HIV-1 (strain MDRC4). Infected cells are treated with increasing concentrations of Amprenavir (a), Indinavir (b), Lopinavir (c), Saquinavir (d), REP 2003 (e), REP 2004 (f), REP 2006 (g) and REP 2007 (h). Dose response curves for CNDO (wild type) are indicated in dotted lines and for MDRC4 (drug resistant) are indicated in solid lines.

FIG. 24. IC50 values from FIGS. 21 and 23 showing fold increases in IC50 values between wild type (CNDO) and drug resistant (MDRC4) strains of recombinant HIV-1.

FIG. 25. CPE assay conducted in Hep2 cells using RSV (strain A2). Infected cells are treated with increasing concentrations of REP 2004 (a), REP 2006 (b), REP 2007 (c) or Ribavirin (d). $IC_{50}$ values calculated from linear regressions are reported in each graph. Cytotoxicity profiles in uninfected Hep2 cells are presented for REP 2004 (e), REP 2006 (f), REP 2007 (g) or Ribavirin (h).

Figure 26:
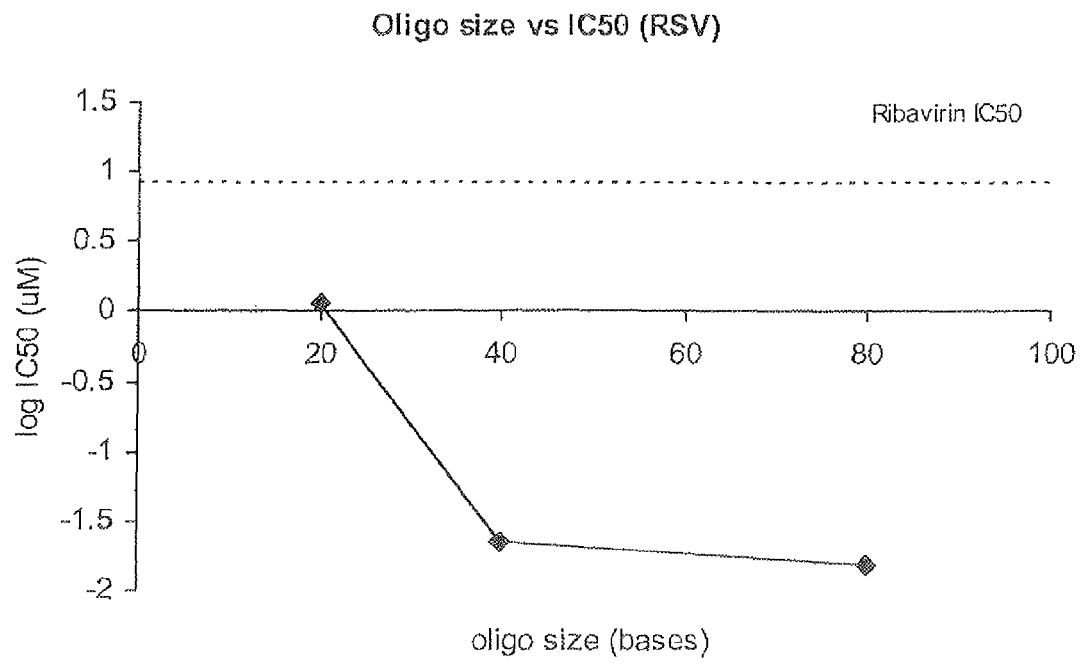

FIG. 26. Relationship between PS-ODN size and $IC_{50}$ against RSV. $IC_{50}$ values from FIG. 25 are plotted against the specific size of each PS-ODN tested in FIG. 25 which showed anti-RSV activity.

Figure 27A:
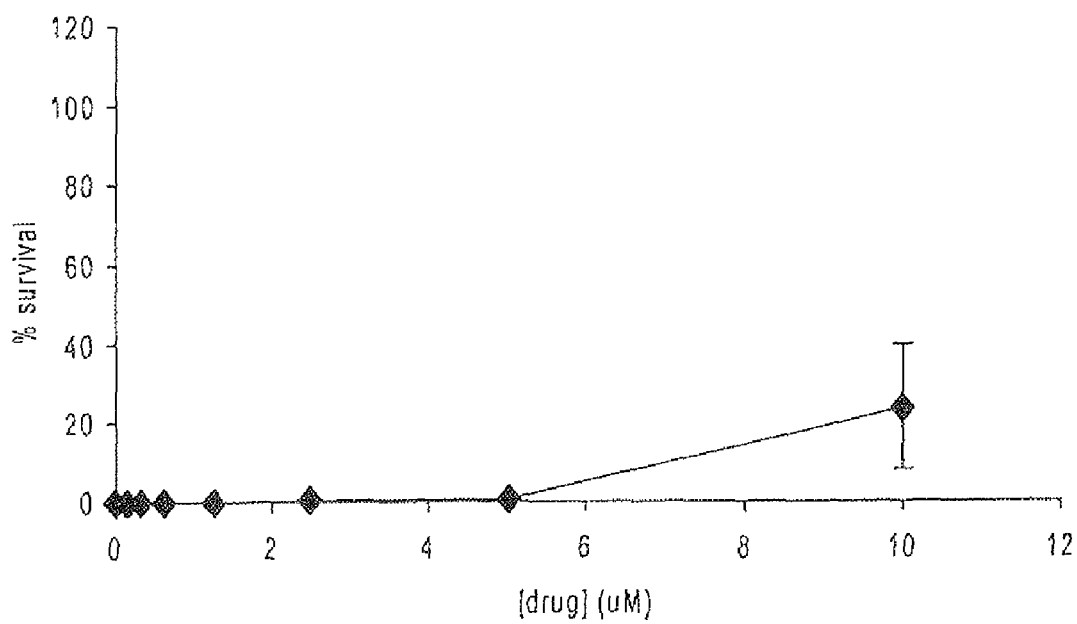
Figure 27B:
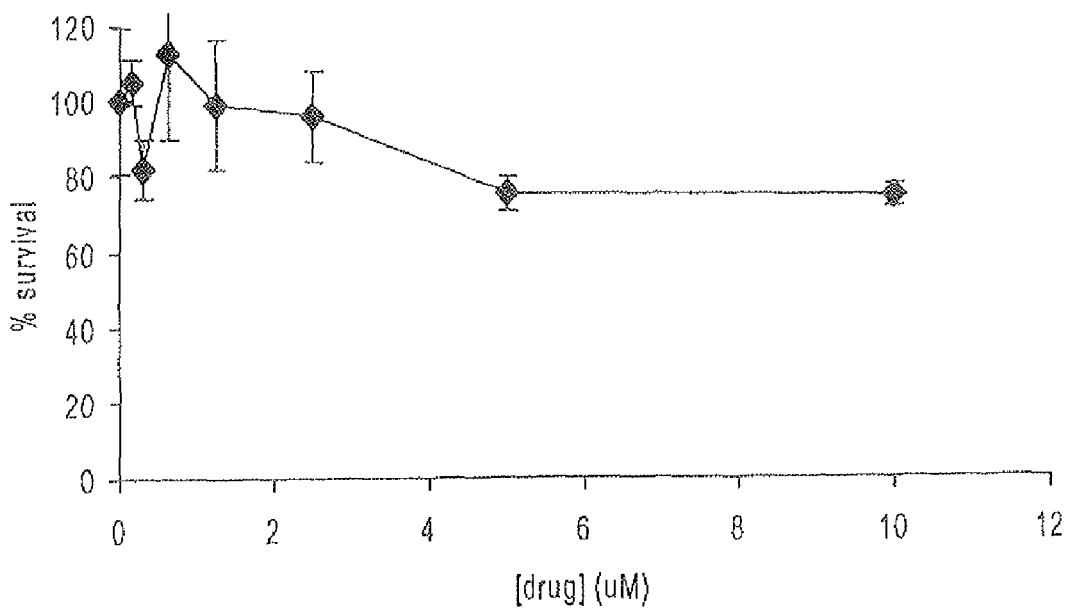

FIG. 27. CPE assay conducted in LLC-MK2 cells using Coxsackievirus B2 (strain Ohio-1). Infected cells are treated with increasing concentrations of REP 2006 (a). The cytotoxicity profile for REP 2006 is shown in (b).

FIG. 28. A) FP interaction assay showing the ability of PS-ODN randomers (REP 2003, 2004, 2006 and 2007) to compete the interaction of a 20 base PS-ODN randomer bait from FBS. Larger randomers compete more efficiently. B) and C) Serum protection and improved delivery of REP2006 in 293 A cells with DOTAP and Cytofectin. D) and E) Serum protection of REP 2006 encapsulated with DOTAP or cytofectin measured by FP.

FIG. 29. Determination of viral lysate binding to baits of different sizes by fluorescence polarization. REP 2032-FL, REP 2003-FL and REP 2004-FL were tested for lysate binding in lysates from HSV-1 (a), HIV-1 (b) or RSV (c).

FIG. 30. Determination of affinity of PS-ODN randomers for viral lysates by fluorescence polarization. Using REP 2004-FL as the bait, complex formation with HSV-1 lysate (a), HIV-1 lysate (b) or RSV lysate (c) was challenged with increasing concentrations of REP 2003, REP 2004, REP 2006 or REP 2007.

Figure 31:
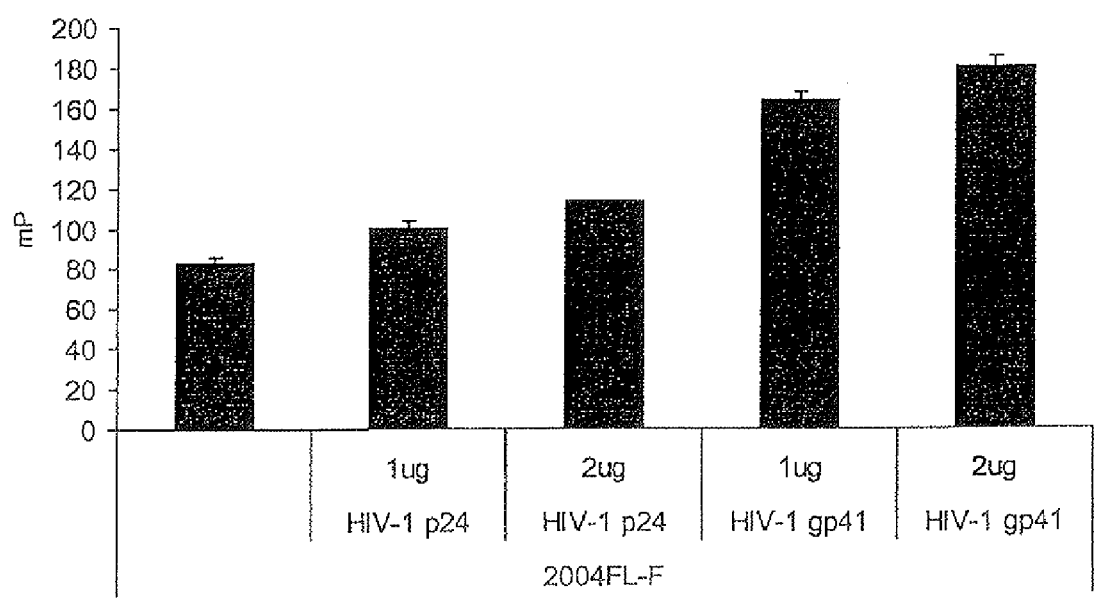

FIG. 31. REP 2004-FL can bind to HIV-1 p24gag and HIV-1 gp41. The ability of REP 2004-FL to interact with increasing amounts of these two purified proteins is tested by fluorescence polarization.

FIG. 32. Effect of bait size on p24 and gp41 binding. Baits of increasing sizes are tested for their ability to bind to p24gag and gp41 by fluorescence polarization.

Figure 33:
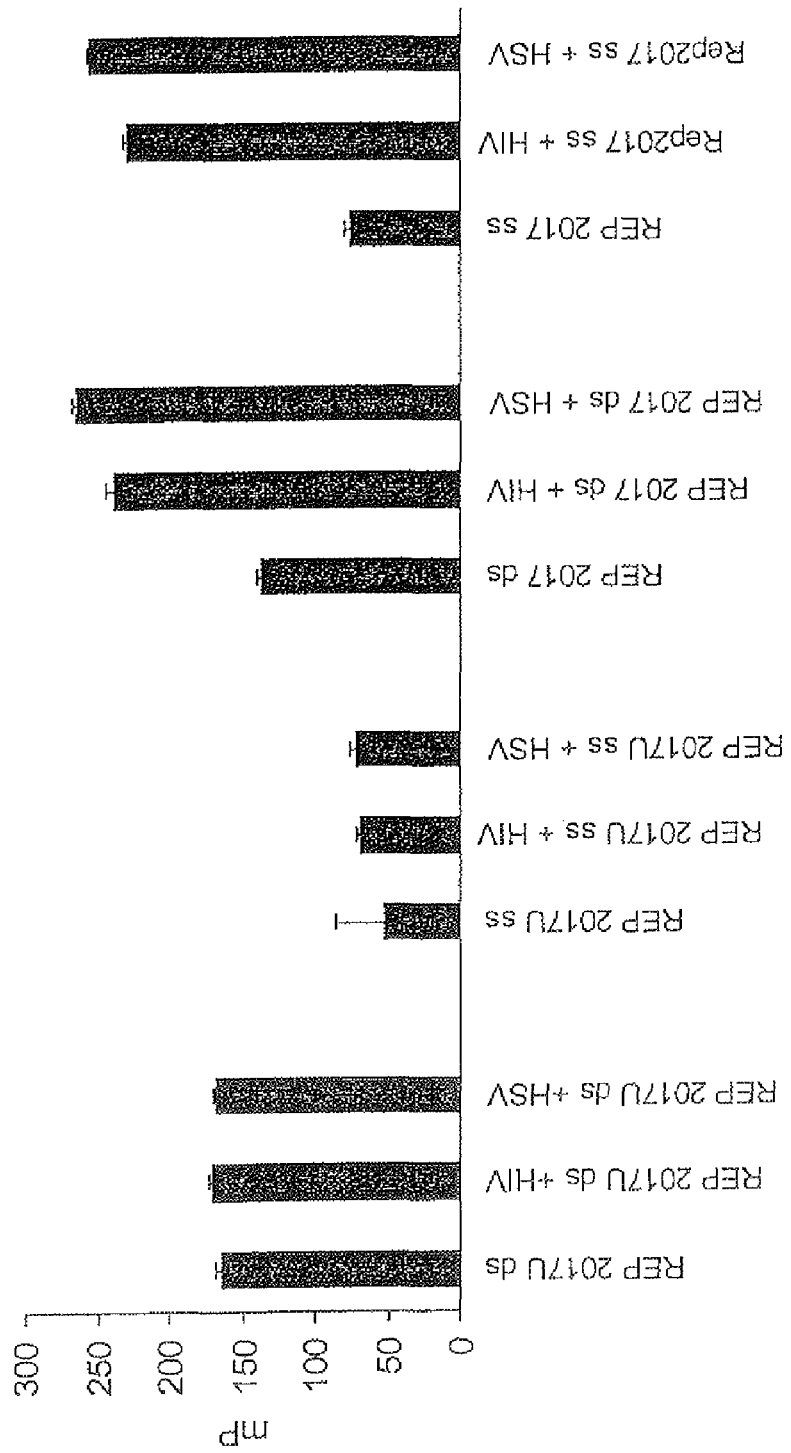

FIG. 33. The ability of double stranded PS-ODNs to bind to viral lysates is tested by fluorescence polarization. Single stranded (ss) or double stranded (ds) phosphorothioated REP 2017 (fluorescently labeled) was prepared as well as its non-thioated analog (2017U). These baits were tested for binding to HSV-1 and HIV-1 viral lysates.

Figure 34:
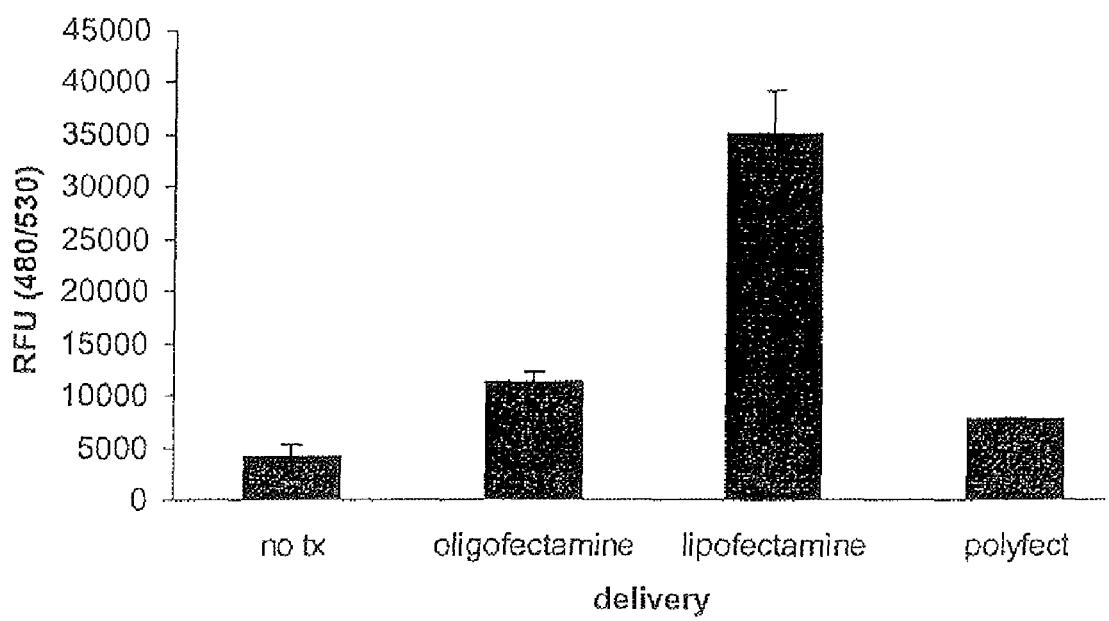

FIG. 34. The delivery of fluorescently tagged PS-ODNs into cells was measured by incubating 293A cells in the presence of 250 nM REP 2004-FL for 4 h. Following the incubation, cells were lysed and the relative fluorescence released from the cells upon lysis was measured by fluorometry.

Figure 35A:
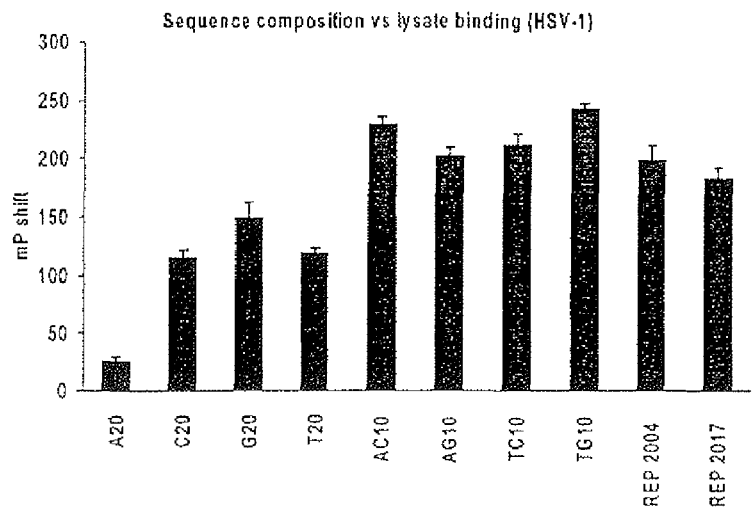
Figure 35B:
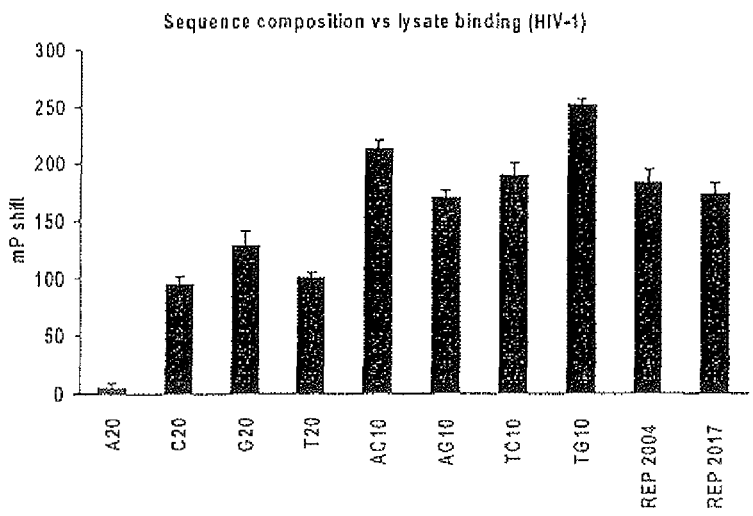
Figure 35C:
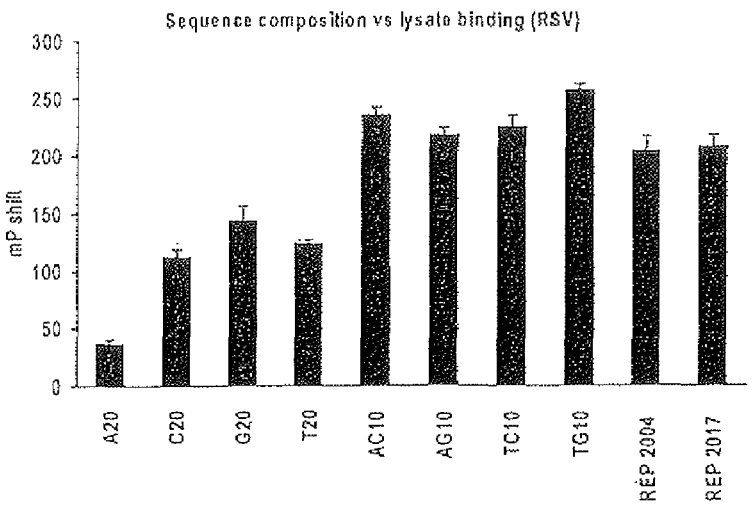

FIG. 35. The ability of 20-mer PS-ODNs of different sequence compositions to bind to viral lysates is measured by fluorescence polarization. PS-ODNs 3' labeled with FITC are incubated in the presence of 1 ug of HSV-1 (a), HIV-1 (b) or RSV (c) lysates. The binding profiles for these PS-ODNs is similar in all three viral lysates (see FIG. 35).

Figure 36:
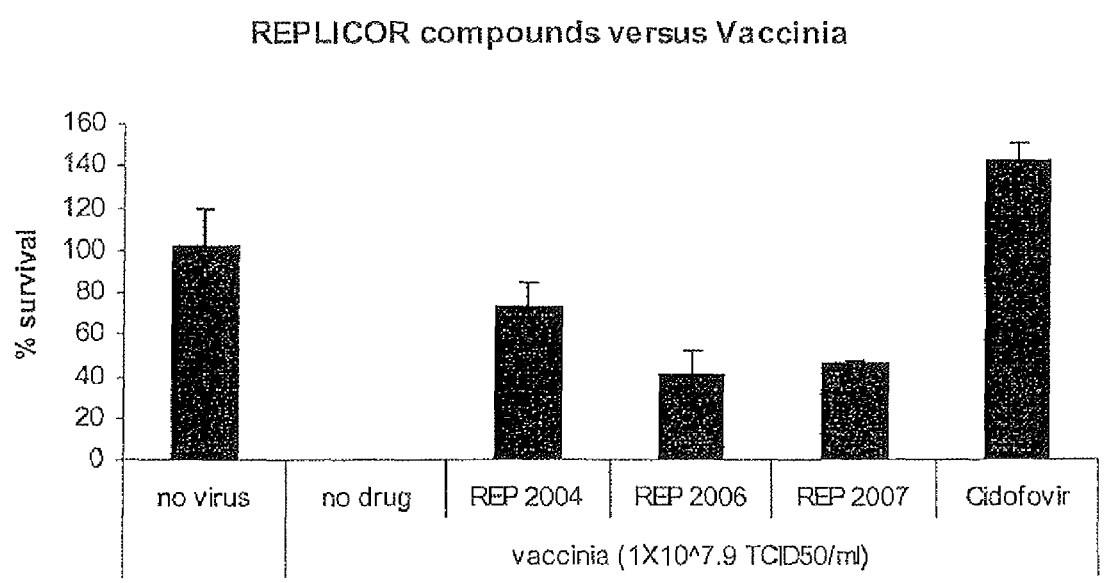

FIG. 36. Indirect determination of viral load in infected supernatants from vaccinia infected VERO cells by measuring the CPE induced by these supernatants in naive cells. REP 2004, 2006 and 2007 were tested at 10 uM while Cidofovir was tested at 50 uM).

FIG. 37. (A) IC50 values generated from a plaque reduction assay conducted in VERO cells using HSV-1 (strain KOS). Infected cells are treated with increasing concentrations of REP 2006 (N40), REP 2028 (G40) (SEQ ID NO: 21), REP 2029 (A40) (SEQ ID NO: 20), REP 2030 (T40) (SEQ ID NO: 23), and REP 2031 (C40) (SEQ ID NO: 22) to generate IC50 values. (B) HSV-1 PRA generated IC50 values of the following: N40 (REP 2006), AC20 (SEQ ID NO: 24) (REP 2055, TC20 (SEQ ID NO: 25) (REP 2056), or AG20 (SEQ ID NO: 26) (REP 2057).

SELECTED ABBREVIATIONS

ON: Oligonucleotide
ODN: Oligodeoxynucleotide
PS: Phosphorothioate
PRA: Plaque reduction assay
PFU: Plaque forming unit
INF A: Influenza A virus
HIV: Human immunodeficiency virus (includes both HIV-1 and HIV-2 if not specified)
HSV: Herpes simplex virus (includes both HSV-2 and HSV-3 if not specified)
RSV: Respiratory syncytial virus
COX: Coxsackievirus
DHBV: Duck hepatitis B virus

DETAILED DESCRIPTION OF THE PREFERRED EMBODIMENT

The present invention is concerned with the identification and use of antiviral oligonucleotides that act by a non-sequence complementary mechanism, and includes the discovery that for many viruses, the antiviral activity is greater for larger oligonucleotides, and are typically optimal for oligonucleotides that are 40 nucleotides or more in length.

As described in the Background, a number of antisense oligonucleotides (ONs) have been tested for antiviral activity. However, such antisense ONs are sequence-specific, and typically are about 16-20 nucleotides in length.

As demonstrated by the results in Examples 1 and 2, the antiviral effect of random PS-ODNs is not sequence specific. Considering the volumes and concentrations of PS-ODNs used in those tests, it is almost theoretically impossible that a particular random sequence is present at more than 1 copy in the mixture. This means than there can be no antisense effect in these PS-ODNs randomers. In the latter example, should the antiviral effect be caused by the sequence-specificity of the PS-ODNs, such effect would thus have to be caused by only one molecule, a result that does not appear possible. For example, for an ON randomer 40 bases in length, any particular sequence in the population would theoretically represent only $¼^{40}$ or $8.27 \times 10^{-25}$ of the total fraction. Given that 1 mole=$6.022 \times 10^{23}$ molecules, and the fact that our largest synthesis is currently done at the 15 micromole scale, all possible sequences will not be present and also, each sequence is present most probably as only one copy. Of course, one skilled in the art applying the teaching of the present invention could also use sequence specific ONs, but utilize the non-sequence complementary activity discovered in the present invention. Accordingly, the present invention is not to be restricted to non-sequence complementary ONs, but disclaims what has been disclosed in the prior art regarding sequence-specific antisense ONs for treating viral infections.

For applicable viruses (including, for example, those for which data is described herein), as the size of the randomer increases, so does its antiviral potency. It should be pointed out that due to limitations in current phosphoramidite-based DNA synthesis, the larger PS-ODNs (e.g., 80- and 120-mers) have a significant contamination of fragments smaller than the desired size. The weaker effects (on a per base basis) seen with larger oligos (80 and 120 bp) may reflect the lower concentration of full-length randomers in these populations and may also reflect a decreased uptake into the cell. It may be possible to achieve much larger increases in antiviral activity if larger randomers (>40 bases) of reasonable purity (75% full length) were synthesized or purified, and/or if the cellular uptake of any of these ODNs is facilitated by a delivery system.

In the present invention, randomers (or other oligonucleotides) may block viral replication by several mechanisms, including but not limited to the following: 1. preventing the adsorption or receptor interaction of virions, thus preventing infection, 2. doping the virus assembly or the packaging of viral genomes into capsids (competing with viral DNA or RNA for packaging), resulting in defective virions, 3. disrupting and or preventing the formation of capsids during packaging or the interaction of capsid proteins with other structural proteins, resulting in inhibition of viral release or causing the release of defective virions, 4. binding to key viral components and preventing or reducing their activity, 5. binding to key host components required for viral proliferation.

Without being limited on the mechanism by which the present viral inhibition is achieved, as indicated above there are several possible mechanisms that could explain and/or predict the inhibitory properties of ONs against viral replication. The first of these is that the general aptameric effect of ONs is allowing for their attachment, either to proteins on the cell surface or to viral proteins, preventing viral adsorption and fusion. The size threshold for effect may be a result of a certain cumulative charge required for interaction.

A second possible mechanism is that ONs may function within the cell by preventing packaging and/or assembly of the virus. ONs above a certain size threshold may compete or interfere with the normal capsid/nucleic acid interaction, preventing the packaging of a functional viral genome inside new viruses. Alternatively, ONs may prevent the formation of a normal capsid, which could prevent normal viral budding, alter viral stability, or prevent proper virion disassembly upon internalization.

While the mechanism of action is not yet entirely clear, assay results demonstrate that the present ONs can exhibit greater efficacy in viral inhibition compared to the clinical correlates, acyclovir, gancyclovir, Ribavirin, and protease inhibitors. ONs in accordance with the present invention could thus be used for treating or preventing viral infection. The viral infections treated could be those caused by human, animal, and plant viruses Broad Spectrum Antiviral Activity According to the conclusions discussed above and the data reported herein, it appeared that random ONs and ON randomers could have broad-spectrum antiviral activity with viruses where assembly and/or packaging and/or encapsidation of the viral genome is a required step in replication. Therefore to test this hypothesis, several PS-ODN randomers of different sizes were selected to be tested in cellular models of various viral Infections. A number of such tests are described herein in the Examples, including tests with CMV, HIV-1, RSV, Coxsackie virus B2, DHBV, Hantavirus, Parainfluenza virus, and Vaccinia virus, as well as the tests on HSV-1 and HSV-2 described in Examples 1 and 2. Despite the high activity level exhibited for some of the tested oligonucleotides, an oligo delivery system such as DOTAP, lipofectamine or oligofectamine could result in much greater efficacies, especially with the larger ($\geq 40$ bases) randomers.

Conclusions on Broad Spectrum Antiviral Activity

The efficacy studies with different viruses demonstrate that random ONs and randomers display inhibitory properties against a variety of different viruses. Moreover, these studies support the conclusion that larger randomers display greater efficacy for viral inhibition than smaller randomers. This suggests a common size and/or charge dependent mechanism for the random ONs or ON randomers activity in all encapsidating viruses.

While HSV and CMV are both double-stranded DNA viruses of the herpesviridae family, HIV is a RNA virus from the retroviridae, and RSV a RNA virus from the paramyxoviridae. Given the fact that ON randomers can inhibit viral function in a variety of different viruses, without being limited to the mechanisms listed, as discussed above the following mechanisms are reasonable: A) ONs/ON randomers are inhibiting viral infection via an aptameric effect, preventing viral fusion with the plasma membrane; and/or B) ONs/ON randomers are preventing or doping the assembly of virions or the packaging of viral DNA within capsids resulting in defective virions; and/or C) ONs/ON randomers are interfering with host proteins or components required in the assembly and/or packaging and/or gene expression of the virus.

Requirement for Antiviral Activity

Since a randomized DNA sequence seems to be sufficient for viral inhibition, it was interesting to see if antiviral activity could be maintained in the absence of the phosphorothioate modification and also if the efficacy was augmented by either choosing a random sequence or a specific sequence found in the viral genome.

Accordingly, DNA and RNA modifications were investigated with respect to their effect on the antiviral efficacy of the randomers. Since randomers work via a non-sequence complementary mechanism, these experiments were designed to test the slight changes in nucleic acid conformation and charge distribution on antiviral efficacy.

To test if ODNs with different nucleotide/nucleoside modifications could inhibit HSV-1, REP 2024, 2026, 2059, and 2060 were tested in the HSV-1 PRA as described in the Examples. REP 2024 (a PS-ODN with a 2-O-Methyl modification to the ribose on 4 bases at both termini of the ODN), REP 2026 (a PO-ODN with methylphosphonate modifications to the linkages between the 4 bases at both termini of the ODN), REP 2059 (RNA PS-ODN randomer 20 bases in length), and REP 2060 (RNA PS-ODN randomer 30 bases in length) showed anti-HSV-1 activity (see FIG. 11).

In the latter example, should the antiviral effect be caused only by the ONs consisting of DNA phosphorothioate backbone, such effect would thus be caused by only one molecule. But other backbones and modifications gave positive antiviral activity. Of course, one skilled in the art applying the teaching of the present invention could also use different chemistry ONs. A modification of the ON, such as, but not limited to, a phosphorothioate modification, appears to be beneficial for antiviral activity. This is most likely due to the needed charge of ONs and/or the requirement for stabilization of DNA both in the media and intracellularly, and it may also be due to the chirality of the PS-ODNs.

Compound REP 2026 showed an antiviral activity while having a central portion comprising unmodified PO-nucleotides and 4 methylphosphonate linkages at both termini protecting from degradation. This indicates that PO-ODNs can be used as antivirals while protected from degradation. This protection can be achieved by modifying nucleotides at termini and/or by using a suitable delivery system as described later.

Figure 10:
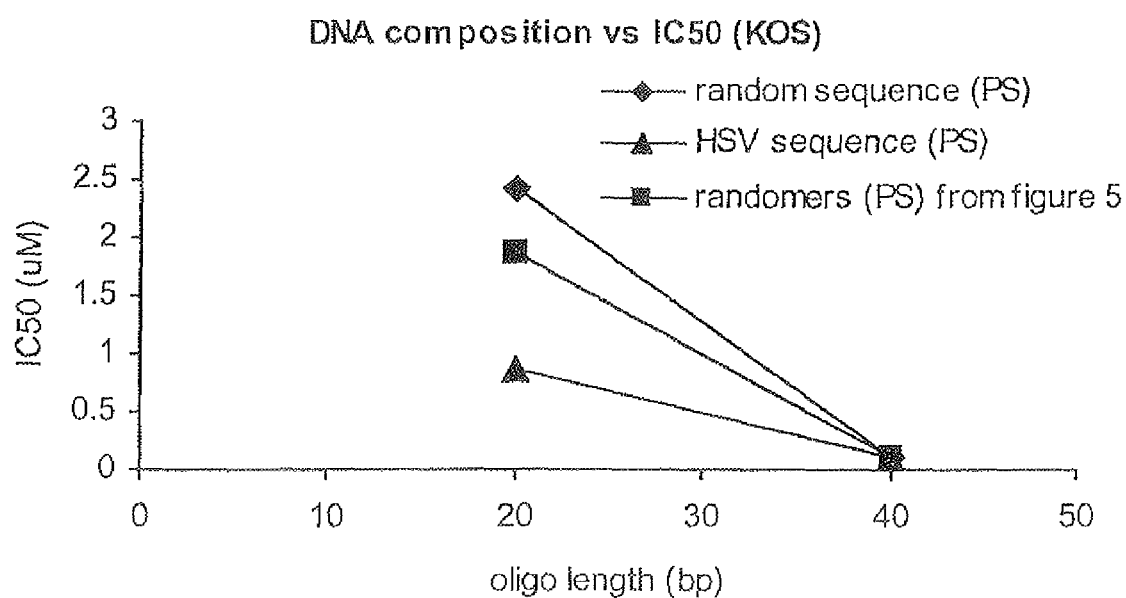
FIG. 10. Relationship between PS-ODN randomer, PS-ODN random sequence, PS-ODN HSV-1 IE110 sequence and $IC_{50}$ against HSV-1. $IC_{50}$ values from FIG. 8 are plotted against the specific size of each PS-ODN tested in FIG. 8 which showed anti-HSV-1 activity. Additional $IC_{50}$ values from FIG. 5 are included for comparison against PS-ODN randomers.
Figure 11A:
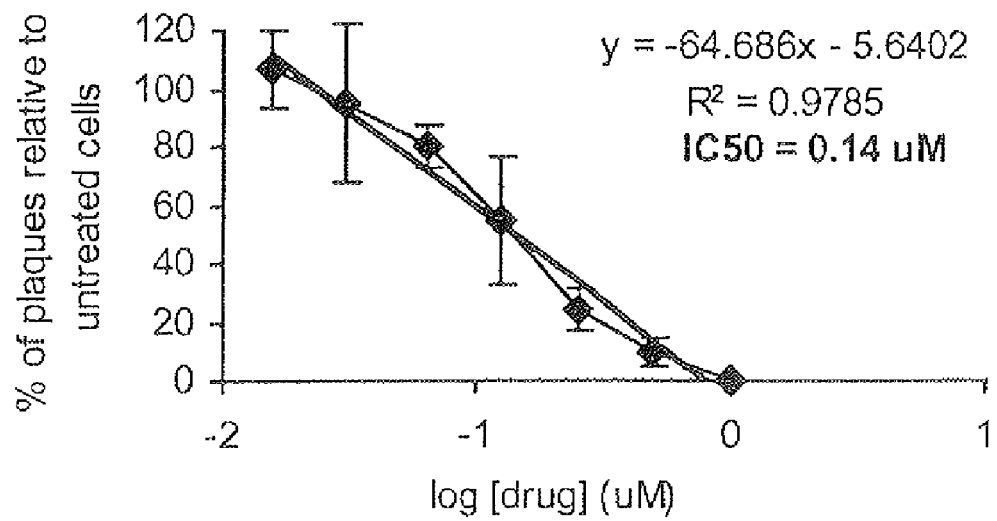
Figure 11B:
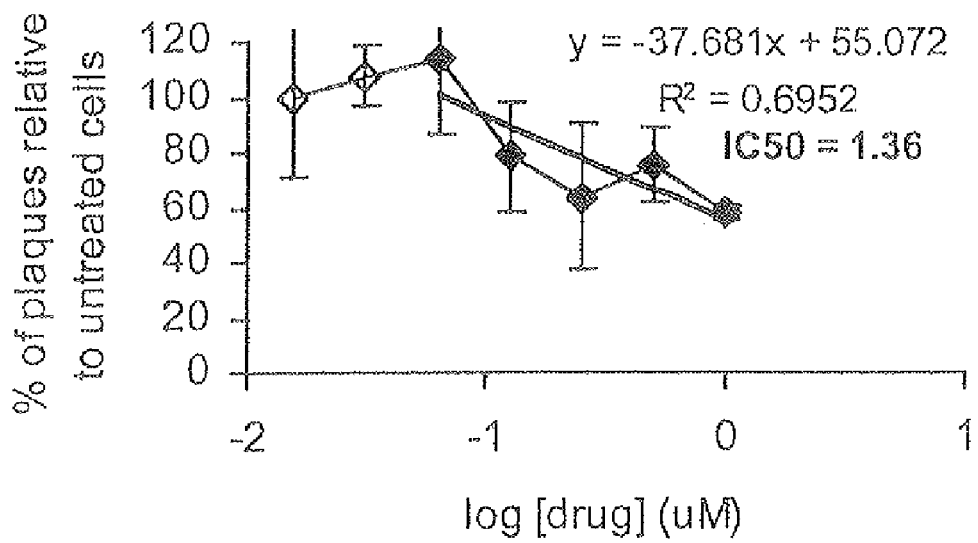
Figure 11C:
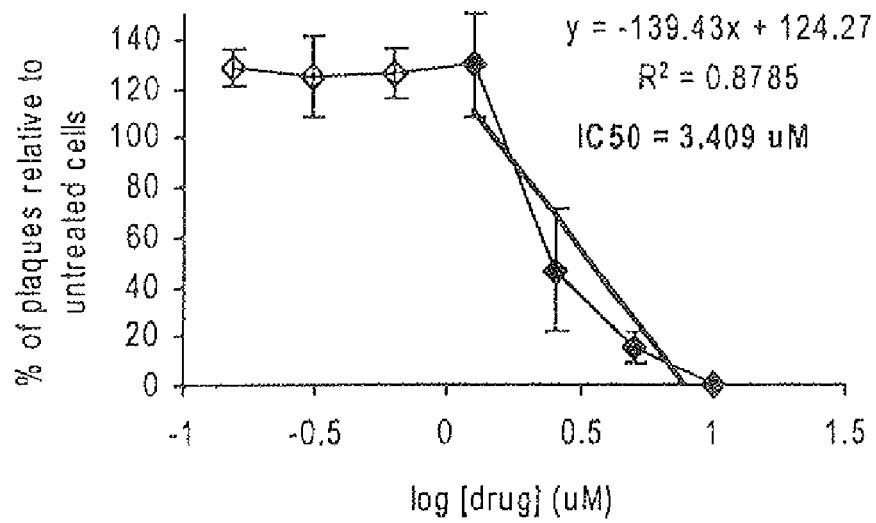
Figure 11D:
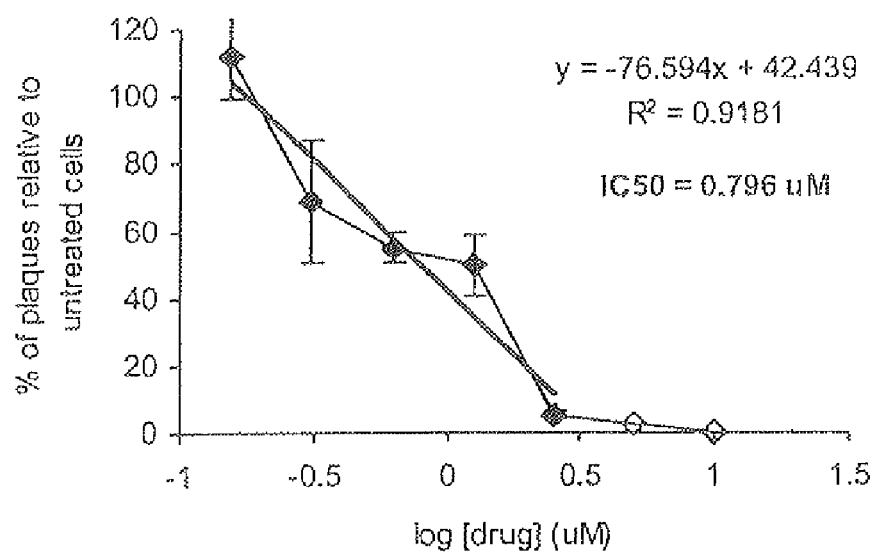

In general, the sequence composition of the DNA used has little effect on the overall efficacy, whether randomer, random sequence or a specific HSV-1 sequence. However, at intermediate lengths, HSV-1 sequence was almost 3× more potent than a random sequence (see FIG. 10). This data suggests that while specific antisense functionality exists for specific HSV sequences, the non-antisense mechanism (non-sequence complementary mechanism) elucidated herein may represent the predominant part of this activity. Indeed, as the ON grows to 40 bases, essentially all of the antiviral activity can be attributed to a non-antisense effect.

Lower Toxicity of Randomer

One goal of using an ON randomer is to lower the toxicity. It is known that different sequences may trigger different responses in the animal, such as general toxicity, interaction with serum proteins, and interaction with immune system (Monteith et al (1998) *Toxicol Sci* 46:365-375). The mixture of ONs may thus decrease toxic effects because the level of any particular sequence will be very low, so that no significant interaction due to sequence or nucleotide composition is likely.

Pharmaceutical Compositions

The ONs of the invention may be in the form of a therapeutic composition or formulation useful for treating (or prophylaxis of) viral diseases, which can be approved by a regulatory agency for use in humans or in non-human animals, and/or against a particular virus or group of viruses. These ONs may be used as part of a pharmaceutical composition when combined with a physiologically and/or pharmaceutically acceptable carrier. The characteristics of the carrier may depend on the route of administration. The pharmaceutical composition of the invention may also contain other active factors and/or agents which enhance activity.

Administration of the ONs of the invention used in the pharmaceutical composition or formulation or to practice the method of treating an animal can be carried out in a variety of conventional ways, such as intraocular, oral ingestion, enterally, inhalation, or cutaneous, subcutaneous, intramuscular, intraperitoneal, intrathecal, intratracheal, or intravenous injection.

The pharmaceutical composition or oligonucleotide formulation of the invention may further contain other chemotherapeutic drugs for the treatment of viral diseases, such as, without limitation, Rifampin, Ribavirin, Pleconaryl, Cidofovir, Acyclovir, Pencyclovir, Gancyclovir, Valacyclovir, Famciclovir, Foscarnet, Vidarabine, Amantadine, Zanamivir, Oseltamivir, Resquimod, antiproteases, HIV fusion inhibitors, nucleotide HIV RT inhibitors (e.g., AZT, Lamivudine, Abacavir), non-nucleotide HIV RT inhibitors, Doconosol, Interferons, Butylated Hydroxytoluene (BHT) and Hypericin. Such additional factors and/or agents may be included in the pharmaceutical composition, for example, to produce a synergistic effect with the ONs of the invention.

The pharmaceutical composition or oligonucleotide formulation of the invention may further contain a polymer, such as, without restriction, polyanionic agents, sulfated polysaccharides, heparin, dextran sulfate, pentosan polysulfate, polyvinylalcohol sulfate, acemannan, polyhydroxycarboxylates, cellulose sulfate, polymers containing sulfonated benzene or naphthalene rings and naphthalene sulfonate polymer, acetyl phthaloyl cellulose, poly-L-lysine, sodium caprate, cationic amphiphiles, cholic acid. Polymers are known to affect the entry of virions in cells by, in some cases, binding or adsorbing to the virion itself. This characteristic of antiviral polymers can be useful in competing with ONs for the binding, or adsorption to the virion, the result being an increased intracellular activity of the ONs compared to its extracellular activity.

Exemplary Delivery System

We monitored the uptake of PS-ODN randomers by exposing cultured cells to fluorescently labeled randomers and then examined the fluorescence intensity in lysed cells after two rounds of washing. The cellular uptake of cells exposed to 250 nM REP 2004-FL was tested with no delivery and after encapsulation in one of the following lipid based delivery systems; Lipofectamine™ (Invitrogen), Polyfect™ (Qiagen) and Oligofectamine™ (Invitrogen). After 4 hours, cells were washed twice with PBS and lysed using MPER lysis reagent (PROMEGA). FIG. 34 shows the relative fluorescence yield from equivalent numbers of exposed cells with and without delivery. We observe than in the presence of all three delivery agents tested, there was a significant increase in the intracellular PS-ODN concentration compared to no delivery.

In keeping with the test results, the use of a delivery system can significantly increase the antiviral potency of ON randomers. Additionally, they will serve to protect these compounds from serum interactions, reducing side effects and maximizing tissue and cellular distribution.

Although PS-ODNs are more resistant to endogenous nucleases than natural phosphodiesters, they are not completely stable and are slowly degraded in blood and tissues. A limitation in the clinical application of PS oligonucleotide drugs is their propensity to activate complement on i.v. administration. In general, liposomes and other delivery systems enhance the therapeutic index of drugs, including ONs, by reducing drug toxicity, increasing residency time in the plasma, and delivering more active drug to disease tissue by extravasation of the carriers through hyperpermeable vasculature. Moreover in the case of PS-ODN, lipid encapsulation prevents the interaction with potential protein-binding sites while in circulation (Klimuk et al., (2000) J Pharmacol Exp Ther 292:480-488).

According to our results described herein, an approach is to use a delivery system such as, but without restriction, lipophilic molecules, polar lipids, liposomes, monolayers, bilayers, vesicles, programmable fusogenic vesicles, micelles, cyclodextrins, PEG, iontophoresis, powder injection, and nanoparticles (such as PIBCA, PIHCA, PHCA, gelatine, PEG-PLA) for the delivery of ONs described herein. The purpose of using such delivery systems are to, among other things, lower the toxicity of the active compound in animals and humans, increase cellular delivery, lower the IC50, increase the duration of action from the standpoint of drug delivery and protect the oligonucleotides from non-specific binding with serum proteins.

We have shown that the antiviral activity of PS-ODN randomers increases with increasing size. Moreover this activity is correlated with increased affinity for viral proteins (in a viral lysate). Since it is well known in the art that the phosphorothioate modification increases the affinity of protein-DNA interaction, we tested the ability of increasingly larger PS-ODN randomers to bind to fetal bovine serum (FBS) (FIG. 28a) using the same FP-based assay used for measuring interaction with viral lysates. In this assay, 250 ug of non-heat inactivated FBS was complexed with a fluorescently labeled 20 base PS-ODN randomer, under conditions where the binding (mP value) was saturated. Unlabelled PS-ODN randomers of increasing size (REP 2003, REP 2004, REP 2006 and REP 2007) were used to compete the interaction of FBS with the labeled bait. The results of this test clearly show that as the size of the PS-ODN randomer increases, so does its affinity for FBS. This result suggests that the most highly active anti-viral PS-ODNs will also be the ones to bind with the highest affinity to proteins.

It is known in the art that one of the main therapeutic problems for phosphorothioate antisense oligonucleotides is their side effects due mainly to this increased interaction with proteins (specifically with serum proteins) as described by Kandimalla and co-workers (Kandimalla et al. (1998) *Bioorg. Med. Chem. Lett.* 8:2103-2108). Our data suggests substantial benefits by a suitable delivery system capable of delivering antiviral ONs into the cell while preventing their interaction with serum proteins.

Figure 28A:
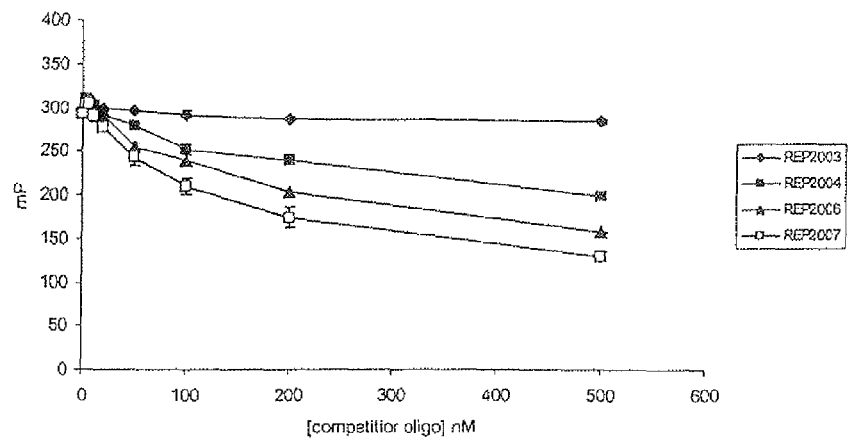
Figure 28B:
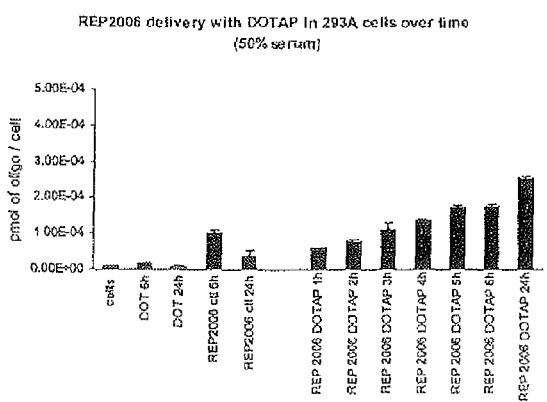
Figure 28D:
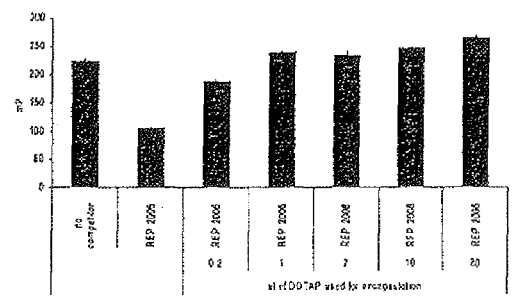
Figure 28C:
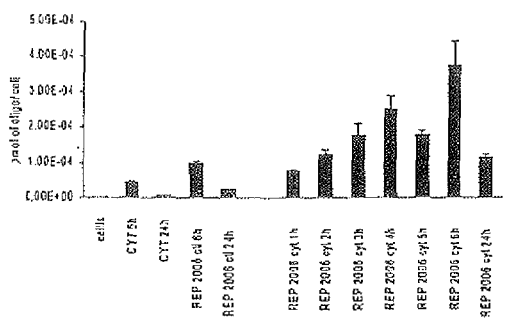
Figure 28E:
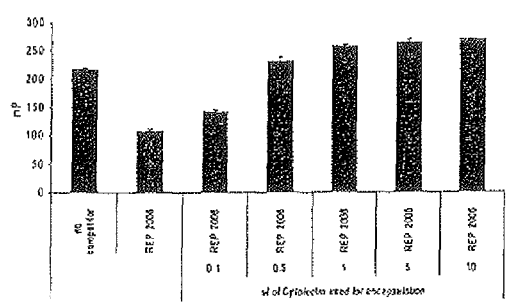

To demonstrate the benefits of a delivery system, we tested two different delivery technologies which are liposomal based; Cytofectin and DOTAP. We measured the delivery of the PS-ODN randomer REP 2006 (encapsulated with either Cytofectin or DOTAP) into 293A cells in the presence of high concentrations of serum (50%) by measuring the intracellular concentration of labeled REP 2006 by fluorometry (FIG. 28b, c). These results show that delivery increases the intracellular concentration of REP 2006, and also that, in the case of DOTAP, the levels of intracellular REP 2006 after 24 hours were markedly increased. Finally, we measured the protection of REP2006 from serum protein interactions by DOTAP (28d) and cytofectin (28e) in our in vitro FP-based interaction assay. Unencapsulated REP 2006 was able to compete bound fluorescent oligo from serum but when REP 2006 was encapsulated with either DOTAP or cytofectin it was no longer able to compete for serum binding. These data suggest that encapsulation protects oligos from serum interaction and will result in a more effective therapeutic effect with fewer side effects.

Another potential benefit in using a delivery system is to protect the ONs from interactions, such as adsorption, with infective virions in order to prevent amplification of viral infection through different mechanisms such as increased cellular penetration of virions.

Another approach is to accomplish cell specific delivery by associating the delivery system with a molecule(s) that will increase affinity with specific cells, such molecules being without restriction antibodies, receptor ligands, vitamins, hormones and peptides.

Additional options for delivery systems are provided below.

Linked ODN

In certain embodiments, ONs of the invention are modified in a number of ways without compromising their ability to inhibit viral replication. For example, the ONs are linked or conjugated, at one or more of their nucleotide residues, to another moiety. Thus, modification of the oligonucleotides of the invention can involve chemically linking to the oligonucleotide one or more moieties or conjugates which enhance the activity, cellular distribution or cellular uptake, increase transfer across cellular membranes specifically or not, or protecting against degradation or excretion, or providing other advantageous characteristics. Such advantageous characteristics can, for example, include lower serum interaction, higher viral-protein interaction, the ability to be formulated for delivery, a detectable signal, improved pharmacokinetic properties, and lower toxicity. Such conjugate groups can be covalently bound to functional groups such as primary or secondary hydroxyl groups. For example, conjugate moieties can include a steroid molecule, a non-aromatic lipophilic molecule, a peptide, cholesterol, bis-cholesterol, an antibody, PEG, a protein, a water soluble vitamin, a lipid soluble vitamin, another ON, or any other molecule improving the activity and/or bioavailability of ONs.

In greater detail, exemplary conjugate groups of the invention can include intercalators, reporter molecules, polyamines, polyamides, polyethylene glycols, polyethers, SATE, t-butyl-SATE, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, fluorescent nucleobases, and dyes.

Groups that enhance the pharmacodynamic properties, in the context of this invention, include groups that improve oligomer cellular uptake and/or enhance oligomer resistance to degradation and/or protect against serum interaction. Groups that enhance the pharmacokinetic properties, in the context of this invention, include groups that improve oligomer uptake, distribution, metabolism or excretion. Exemplary conjugate groups are described in International Patent Application PCT/US92/09196, filed Oct. 23, 1992, which is incorporated herein by reference in its entirety.

Conjugate moieties can include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et at., *EMBO J.*, 1991, 10, 1111-1118; Kabanov et al., *FEBS Lett.*, 1990, 259, 327-330; Svinarchuk et at., *Biochimie*, 1993, 75, 49-54), a phospholipid, e.g., dihexadecyl-rac-glycerol or triethyl-ammonium 1,2-di-O-hexadecyl-rac-glycero-3-H-phosphonate (Manoharan et at., *Tetrahedron Lett.*, 1995, 36, 3651-3654; Shea et al., *Nucl. Acids Res.*, 1990, 18, 3777-3783), a polyamine or a polyethylene glycol chain (Manoharan et at., *Nucleosides & Nucleotides*, 1995, 14, 969-973), or adamantane acetic acid (Manoharan et at., *Tetrahedron Lett*, 1995, 36, 3651-3654), a palmityl moiety (Mishra et at., *Biochim. Biophys. Acta*, 1995, 1264, 229-237), or an octadecylamine or hexylaminocarbonyl-oxycholesterol moiety (Crooke et al., *J. Pharmacol Exp. Ther.*, 1996, 277, 923-937.

The present oligonucleotides may also be conjugated to active drug substances, for example without limitation, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Exemplary U.S. patents that describe the preparation of exemplary oligonucleotide conjugates include, for example, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is incorporated by reference herein in its entirety.

Another approach is to prepare antiviral ONs as lipophilic pro-oligonucleotides by modification with enzymatically cleavable charge neutralizing adducts such as s-acetylthio-ethyl or s-pivasloylthio-ethyl (Vives et al., 1999, *Nucl Acids Res* 27: 4071-4076). Such modifications have been shown to increase the uptake of ONs into cells.

Design of Non-Specific ONs

In another approach, an antiviral ON demonstrating low, preferably the lowest possible, homology with the human (or other subject organism) genome is designed. The goal is to obtain an ON that will show the lowest toxicity due to interactions with human or animal genome sequence(s) and mRNAs. The first step is to produce the desired length sequence of the ON, e.g., by aligning nucleotides A, C, G, T in a random fashion, manually or, more commonly, using a computer program. The second step is to compare the ON sequence with a library of human sequences such as GenBank and/or the Ensemble Human Genome Database. The sequence generation and comparison can be performed repetitively, if desired, to identify a sequence or sequences having a desired low homology level with the subject genome. Desirably, the ON sequence is at the lowest homology possible with the entire genome, while also preferably minimizing self interaction.

Non-Specific ONs with Antisense Activity

In another approach, an antiviral non-specific sequence portion(s) is/are coupled with an antisense sequence portion(s) to increase the activity of the final ON. The non-specific portion of the ONs is described in the present invention. The antisense portion is complementary to a viral mRNA.

Non-Specific ONs with a G-Rich Motif Activity

In another approach, an antiviral non-specific sequence portion(s) is/are coupled with a motif portion(s) to improve the activity of the final ON. The non-specific portion of the ON is described in the present invention. The motif portion can, as non-limiting examples, include, CpG, Gquartet, and/or CG that are described in the literature as stimulators of the immune system. Agrawal et al. (2001) *Curr. Cancer Drug Targets* 3:197-209.

Non-Watson-Crick ONs

Another approach is to use an ON composed of one type or more of non-Watson-Crick nucleotides/nucleosides. Such ONs can mimic PS-ODNs with some of the following characteristics similar to PS-ODNs: a) the total charge; b) the space between the units; c) the length of the chain; d) a net dipole with accumulation of negative charge on one side; e) the ability to bind to proteins; f) the ability to bind viral proteins, g) the ability to penetrate cells, h) an acceptable therapeutic index, i) an antiviral activity. The ON has a preferred phosphorothioate backbone but is not limited to it. Examples of non-Watson-Crick nucleotides/nucleosides are described in Kool, 2002, *Acc. Chem. Res.* 35:936-943; and Takeshita et al., (1987) *J. Biol. Chem*, 262:10171-10179 where ODNs containing synthetic abasic sites are described.

Antiviral Polymer

Another approach is to use a polymer mimicking the activity of phosphorothioate ODNs. As described in the literature, several anionic polymers were shown to have antiviral inhibitory activity. These polymers belong to several classes: (1) sulfate esters of polysaccharides (dextrin and dextran sulfates; cellulose sulfate); (2) polymers containing sulfonated benzene or naphthalene rings and naphthalene sulfonate polymers; (3) polycarboxylates (acrylic acid polymers); and acetyl phthaloyl cellulose (Neurath et al. (2002) *BMC Infect Dis* 2:27); and (4) abasic oligonucleotides (Takeshita et al., 1987, *J. Biol. Chem.* 262:10171-10179). Other examples of non-nucleotide antiviral polymers are described in the literature. The polymers described herein mimic PS-ODNs described in this invention and have the following characteristics similar to PS-ODNs: a) the length of the chain; b) a net dipole with accumulation of negative charge on one side; c) the ability to bind to proteins; d) the ability to bind viral protein, e) an acceptable therapeutic index, f) an antiviral activity. In order to mimic the effect of a PS-ODN, the antiviral polymer may preferably be a polyanion displaying similar space between its units as compared to a PS-ODN. It may also have the ability to penetrate cells alone or in combination with a delivery system.

Antiviral Activity of Double-Stranded PS-ODNs

A random sequence (REP 2017) and its complement (either PS modified or unmodified) are fluorescently labeled as described elsewhere and tested for their ability to bind to purified HSV-1 and HIV-1 proteins by fluorescence polarization as described in the present invention. Hybridization was verified by acrylamide gel electrophoresis. Unmodified REP 2017 (2017U), either single (ss) or double stranded (ds), had no binding activity in either HSV-1 or HIV-1 lysates. However, PS modified REP 2017, either single stranded or double stranded, was capable of HSV-1 and HIV-1 interaction (see FIG. 33).

According to our results described herein, an approach is to use double stranded ONs as effective antiviral agents. Preferentially such ONs have a phosphorothioate backbone but may also have other and/or additional modifications which increase either their delivery and/or antiviral activity and/or stability as described herein for single stranded ONs.

In Vitro Assay for Drug Discovery

An in vitro assay is developed based on fluorescence polarization to measure the ability of PS-ODNs to bind to viral components, e.g., viral proteins. When a protein (or another interactor) binds to the fluorescently labeled bait, the three dimensional tumbling of the bait in solution is retarded. The retardation of this tumbling is measured by an inherent increase in the polarization of excited light from the labeled bait. Therefore, increased polarization (reported as a dimensionless measure [mP]) is correlated with increased binding.

One methodology is to use as bait a PS-ODN randomer labeled at the 3' end with FITC using an inflexible linker (3'-(6-Fluorescein) CPG). This PS-ODN randomer is diluted to 2 nM in assay buffer (10 mM Tris, pH7.2, 80 mM NaCl, 10 mM EDTA, 100 mM b-mercaptoethanol and 1% tween 20). This oligo is then mixed with an appropriate interactor. In this case, we use lysates of sucrose gradient purified HSV-1 (strain MacIntyre), HIV-1 (strain Mn) or RSV (strain A2) suspended in 0.5M KCl and 0.5% Triton X-100 (HSV-1 and HIV-1) or 10 mM Tris, pH7.5, 150 mM NaCl, 1 mM EDTA and 0.1% Triton X-100 (RSV). Following bait interaction, the complexes are challenged with various unlabelled PS-ODNs to assess their ability to displace the bait from its complex.

Figure 29A:
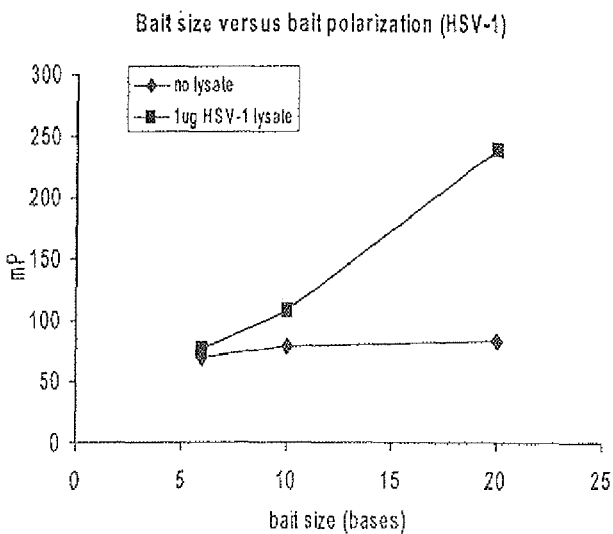
Figure 29B:
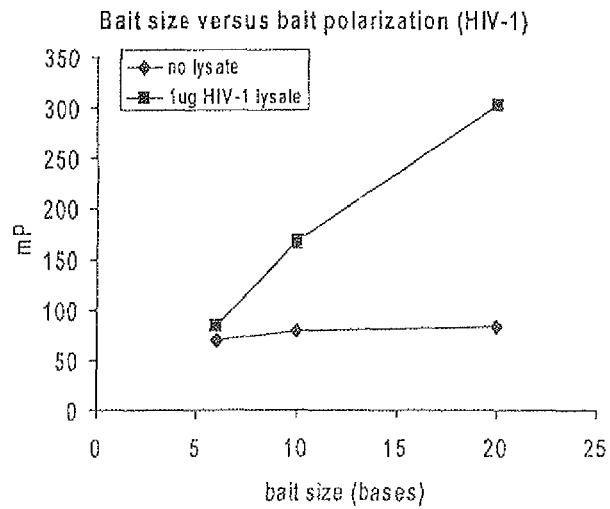
Figure 29C:
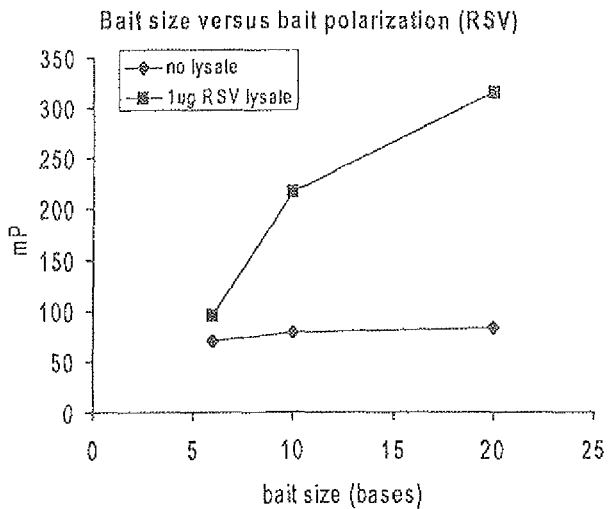

In FIG. 29, we show a preliminary test with three baits of different sizes; 6 (REP 2032-FL), 10 (REP 2003-FL) and 20 bases (REP 2004-FL). These baits were tested for their ability to interact with HSV-1 (FIG. 29a), HIV-1 (FIG. 29b) and RSV (FIG. 29c) lysates. In the presence of any of the viral lysates the degree of binding was dependent on the size of the bait used, with 2004-FL displaying the largest shift in mP (binding) in the presence of viral lysate. We note that this is similar to the size dependent antiviral efficacy of PS-ODN randomers. This bait was then used to assess the ability of PS-ODNs of different sizes to compete the interaction of the bait with the lysate.

Figure 30A:
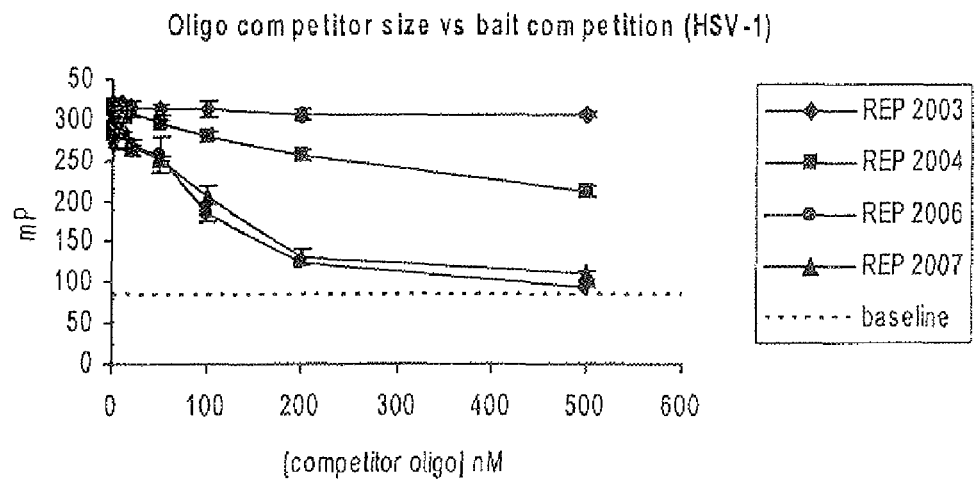
Figure 30B:
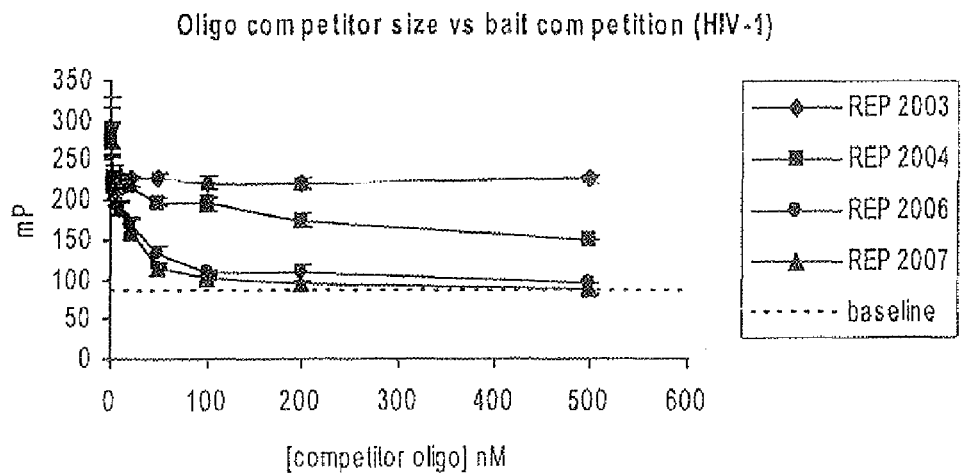
Figure 30C:
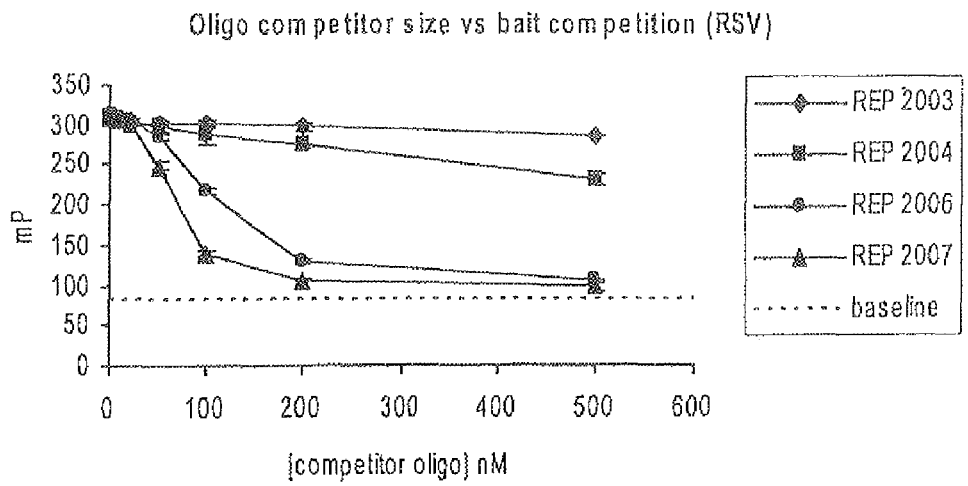

In FIG. 30, the interaction of REP 2004-FL with HSV-1 (FIG. 30a), HIV-1 (FIG. 30b) and RSV (FIG. 30c) lysates is challenged with PS-ODNs of increasing size. For each viral lysate tested, we note that REP 2003 is unable to compete the bait away from the lysate. The bait interaction was very strong as revealed by the relatively weak competition elicited by the REP 2004 (unlabeled bait) competitor. However, it was observed that as the size of the competitor PS-ODN increased above 20 bases, its ability to displace the bait became more robust. This indicates an increased affinity to protein components in the viral lysate as the PS-ODN randomer size increases. This phenomenon mirrors the increased antiviral activity of larger PS-ODN randomers against HSV-1, HSV-2, CMV, HIV-1 and RSV.

The similarity between the efficacy in bait competition and antiviral activity of PS-ODN randomers indicates that this assay paradigm is a good predictor of antiviral activity. This assay is robust, easy to perform and very stable, making it a very good candidate for a high throughput screen to identify novel antiviral molecules based not on specific target identification but on their ability to interact with one or more components, e.g., viral proteins.

While the exemplary method described herein utilizes fluorescence polarization to measure interaction with the viral lysate, numerous techniques are known in the art for monitoring protein interactions, and can be used in the present methods. These include without restriction surface plasmon resonance, fluorescence resonance energy transfer (FRET), enzyme linked immunosorbent assay (ELSIA), gel electrophoresis (to measure mobility shift), isothermal titration and differential scanning microcalorimetry and column chromatography. These other different techniques can be applied to measure the interaction of ONs with a viral lysate or component, and thus can be useful in screening for compounds which have anti-viral activity.

The method described herein is used to screen for novel compounds from any desired source, for example, from a library synthesized by combinatorial chemistry or isolated by purification of natural substances. It can be used to a) determine appropriate size, modifications, and backbones of novel ONs; b) test novel molecules including novel polymers; predict a particular virus' susceptibility to novel ONs or novel compounds; or d) determine the appropriate suite of compounds to maximally inhibit a particular virus.

The increased lysate affinity with larger sized PS-ODN randomers suggests that the antiviral mechanism of action of PS-ODN randomers is based on an interaction with one or more viral protein components which prevents either the infection or correct replication of virions. It also suggests that this interaction is charge (size) dependent and not dependent on sequence. As these PS-ODN randomers have a size dependent activity across multiple viruses spanning several different families, we suggest that PS-ODN randomers interfere with common, charge dependent protein-protein interactions, protein-DNA/RNA interactions, and/or other molecule-molecule interactions. These interactions can include (but are not limited to):

a. The interaction between individual capsid subunits during capsid formation.
b. The interaction between the capsid/nucleocapsid protein and the viral genome.
c. The interaction between the capsid and glycoproteins during budding.
d. The interaction between the glycoprotein and its receptor during infection.
e. The interaction between other viral key components involved in viral replication.

These multiple, simultaneous inhibitions of protein-protein interactions represent a novel mechanism for antiviral inhibition.

Effect of PS-ODN Sequence Composition on Lysate

We monitored the ability of PS-ODNs of different sequences to interact with several viral lysates. In each case, a 20-mer PS-ODN is labeled at the 3' end with FITC as previously described herein. The PS-ODNs tested consisted of A20 (SEQ ID NO: 12), T20 (SEQ ID NO: 15), G20 (SEQ ID NO: 13), C20 (SEQ ID NO: 14), AC10 (SEQ ID NO: 16), AG10 (SEQ ID NO: 17), TC10 (SEQ ID NO: 18), TG10 (SEQ ID NO: 19), REP 2004 and REP 2017. Each of these sequences is diluted to 4 nM in assay buffer and incubated in the presence of 1 ug of HSV-1, HIV-1 or RSV lysate. Interaction is measured by fluorescence polarization.

The profile of interaction with all sequences tested is similar in all viral lysates, indicating that the nature of the binding interaction is very similar. Within each lysate, the PS-ODNs of uniform composition (A20 (SEQ ID NO:12), G20 (SEQ ID NO:13), T20 (SEQ ID NO:15), C20 (SEQ ID NO:14)) were the weakest interactors with A20 (SEQ ID NO:12) being the weakest interactor of these by a significant margin. For the rest of the PS-ODNs tested, all of them displayed a similar, strong interaction with the exception of TG10 (SEQ ID NO:19), which consistently displayed the strongest interaction in each lysate (see FIG. 35).

Target Identification for PS-ODN Randomers in HIV-1

The ability of PS-ODN randomers to bind to purified HIV-1 proteins is tested by fluorescence polarization as described in example 9. Increasing quantities of purified HIV-1 p24 or purified HIV-1 gp41 were reacted with REP 2004-FL (see FIG. 31). We note that for both these proteins, there is a protein concentration dependent shift in fluorescence polarization, indicating an interaction with both these proteins.

Figure 32A:
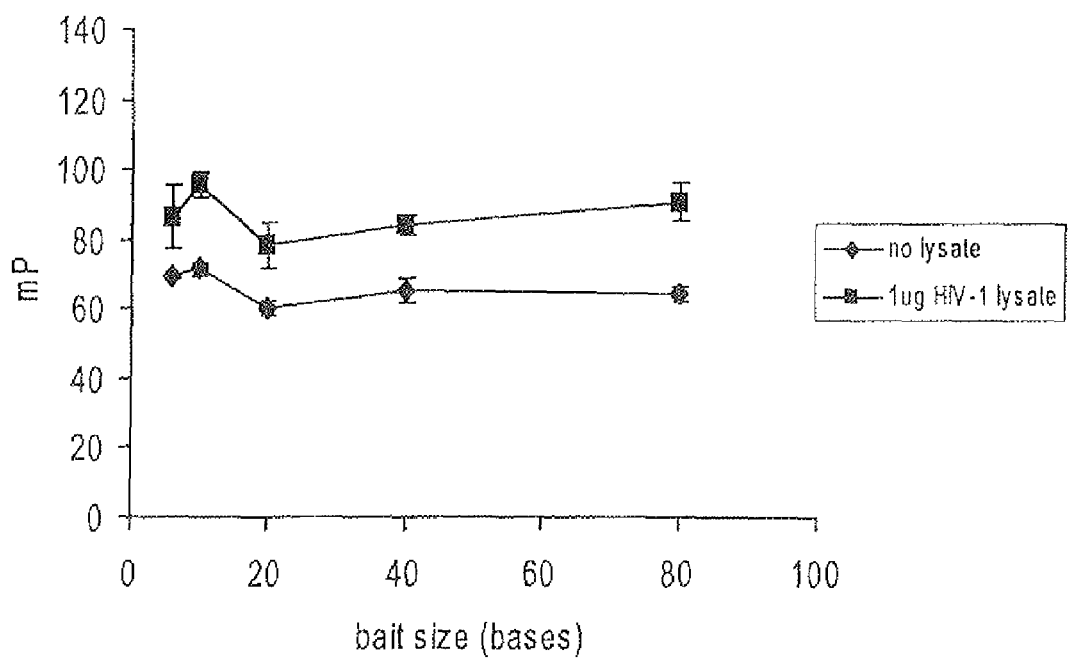
Figure 32B:
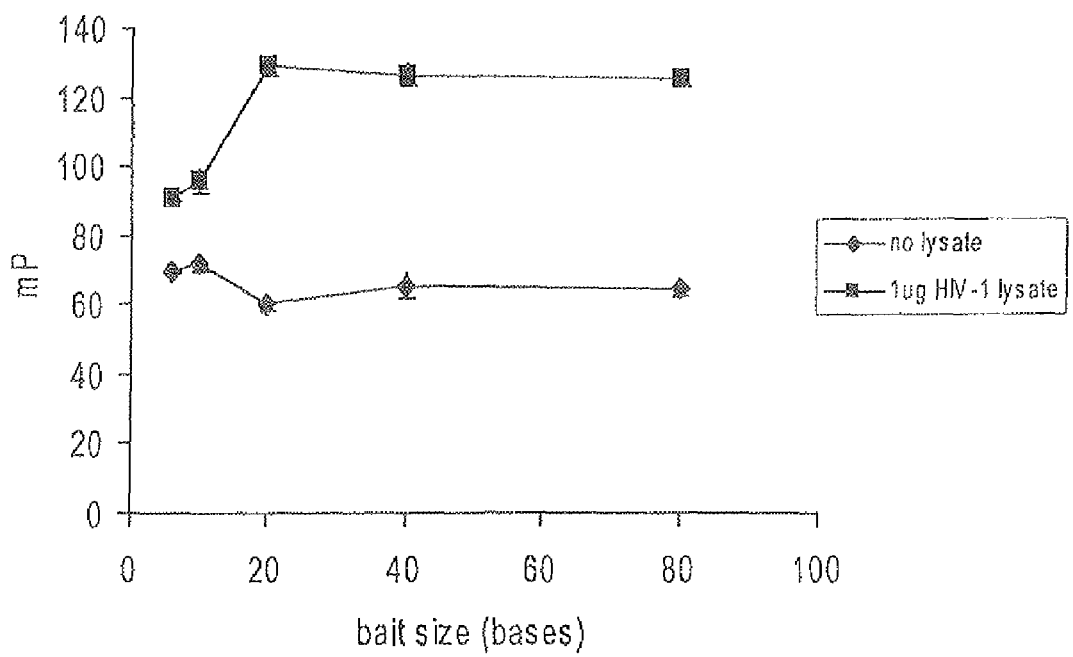

The ability of a range of sizes of PS-ODN randomers to bind to these proteins was also tested using fluorescent versions of REP 2032, REP 2003, REP 2004, REP 2006 and REP 2007 (see FIG. 32). We observe that for p24, there is no size dependent interaction with p24 (see FIG. 32a) however; we did see an increase in gp41 binding in PS-ODN randomers larger than 20 bases versus those less than 20 bases (see FIG. 32b). This suggests when PS-ODN randomer length increases above 20 bases, multiple copies of gp41 can bind to individual randomers, increasing their polarization.

This is a significant observation as it demonstrates the potential of larger ONs to sequester structural proteins during viral synthesis and limit their availability for the formation of new virions.

High Affinity Oligonucleotides

Another approach is a method to enrich or purify antiviral ON(s) having a higher affinity for viral components, such as viral proteins, than the average affinity of the ONs in a starting pool of ONs. The method will thus provide one or more non-sequence complementary ON(s) that will exhibit increased affinity to one or more viral components, e.g., having a three-dimensional shape contributing to such elevated binding affinity. The rationale is that while ON(s) will act as linear molecules in binding with viral components, they can also fold into a 3-dimensional shape that can enhance the interaction with such viral components. Without being limited to the specific technique, high affinity ONs can be purified or enriched in the following ways.

One method for purifying a high affinity ON, or a plurality of high affinity ONs, involves using a stationary phase medium with bound viral protein(s) as an affinity matrix to bind ONs, which can then be eluted under increasingly stringent conditions (e.g., increasing concentration of salt or other chaotropic agent, and/or increasing temperature and/or changes in pH). Such a method can, for example, be carried out by:

(a) loading a pool of ONs onto an exchange column having a viral protein or several viral proteins or a viral lysate bound to a stationary phase;
(b) displacing (eluting) bound ONs from the column, e.g., by using a displacer solution such as an increasing salt solution;
(c) collecting fractions of eluted ONs at different salt concentration;
(d) cloning and sequencing eluted ONs from different fractions, more preferably from a fraction(s) at high salt concentration, such that the ONs eluted at the high salt concentration have a greater binding affinity with the viral protein(s); and
(e) Testing the activity of sequenced ON(s) in assays such binding and/or viral inhibition assay, e.g., a fluorescence polarization-binding assay as described herein and/or in a cellular viral inhibition assay and/or in an animal viral inhibition assay.

In a second example, a method derived and modified from the SELEX methodology (Morris et al (1998) Biochemistry 95:2902-2907) can be used for purifying the high affinity ON. One implementation of such a method can be performed as:

(a) providing a starting ON pool material, for example, a collection of synthetic random ONs containing a high number of sequences, e.g., one hundred trillion ($10^{14}$) to ten quadrillion ($10^{16}$) different sequences. Each ON molecule contains a segment of random sequence flanked by primer-binding sequences at each end to facilitate polymerase chain reaction (PCR). Because the nucleotide sequences of essentially all of the molecules are unique, an enormous number of structures are sampled in the population. These structures determine each molecule's biochemical properties, such as the ability to bind a given viral target molecule;
(b) contacting ONs with a viral protein or several viral proteins or a viral lysate;
(c) selecting ONs that bind to viral protein(s), using a partition technique(s) that can partition bound and unbound ONs, such as native gel shifts and nitrocellulose filtration. Either of these methods physically separates the bound species from the unbound species, allowing preferential recovery of those sequences that bind best. Also, to select ON (s) that bind to a small protein, it is desirable to attach the target to a solid support and use that support as an affinity purification matrix. Those molecules that are not bound get washed off and the bound ones are eluted with free target, again physically separating bound and unbound species;
(d) amplifying the eluted binding ON(s), e.g., by using PCR using primers hybridizing with both flanking sequences of ONs;
(e) steps (b) (c) and (d) can be performed multiple times (i.e., multiple cycles or rounds of enrichment and amplification) in order to preferentially recover ONs that display the highest binding affinity to viral protein(s). After several cycles of enrichment and amplification, the population is dominated by sequences that display the desired biochemical property;

(f) cloning and sequencing one or more ONs selected from an enrichment cycle, e.g., the last such cycle; and (g) testing the binding and/or activity of sequenced ON(s) in assays, e.g., in a fluorescence polarization binding assay as described herein and/or in a cellular viral inhibition assay and/or in an animal viral inhibition assay.

Another approach is to apply a modification of a split synthesis methodology to create one-bead one-PS-ODN and one-bead one-PS2-ODN libraries as described in Yang et al (2002) *Nucl. Acids Res.* 30(e132):1-8. Binding and selection of specific beads to viral proteins can be done. Sequencing both the nucleic acid bases and the positions of any thioate/dithioate linkages can be carried out by using a PCR-based identification tag of the selected beads. This approach can allow for the rapid and convenient identification of PS-ODNs or PS2-ODNs that bind to viral proteins and that exhibit potent antiviral properties.

Once the specific sequences that bind to the viral proteins with high affinity are determined (e.g., by amplification and sequencing of individual sequences), one or more such high affinity sequences can be selected and synthesized (e.g., by either chemical or enzymatic synthesis) to provide a preparation of high affinity ON(s), which can be modified to improve their activity, including improving their pharmacokinetic properties. Such high affinity ONs can be used in the present invention.

Prion Diseases

Another approach is used in an alternative embodiment of the present invention for the treatment, the control of the progression, or the prevention of prion disease. This fatal neurodegenerative disease is infectious and can affect both humans and animals. Structural changes in the cellular prion protein, PrPC to its scrapie isoform, PrPSC, are considered to be the obligatory step in the occurrence and propagation of the prion disease. Amyloid polymers are associated with neuropathology of the prion disease.

The incubation of a prion protein fragment and double stranded nucleic acid results in the formation of amyloid fibres (Nandi et al (2002), *J Mol Biol* 322: 153-161). ONs having affinity to proteins such as phosphorothioates are used to compete or inhibit the interaction of double stranded nucleic acid with the PrPC and consequently stop the formation of the amyloid polymers. Such ONs of different sizes and different compositions can be used in an appropriate delivery form to treat patients suffering from prion diseases or for prophylaxis in high risk situations. Such interfering ONs can be identified by measuring folding changes of amyloid polymerase as described by Nandi et al. (supra) in the presence of test ONs.

Putative Viral Etiologies

Another approach is used in another embodiment of the present invention for the treatment or prevention of diseases or conditions with putative viral etiologies as described without limitation in the following examples. Viruses are putative causal agents in diseases and conditions that are not related to a primary viral infection. For example, arthritis is associated with HCV (Olivieri et al. (2003) *Rheum Dis Clin North Am* 29:111-122), Parvovirus B19, HIV, HSV, CMV, EBV, and VZV (Stahl et al. (2000) *Clin Rheumatol* 19:281-286). Other viruses have also been identified as playing a role in different diseases. For example, influenza A in Parkinson's disease (Takahashi et al. (1999), *Jpn J Infect Dis* 52:89-98), Coronavirus, EBV and other viruses in Multiple Sclerosis (Talbot et al (2001) *Curr Top Microbiol Immunol* 253:247-71); EBV, CMV and HSV-6 in Chronic Fatigue Syndrome (Lerner et al. (2002) *Drugs Today* 38:549-561); and paramyxoviruses in asthma (Walter et al (2002) *J Clin Invest* 110:165-175) and in Paget's disease; and HBV, HSV, and influenza in Guillain-Barre Syndrome.

Because of these etiologies, inhibition of the relevant virus using the present invention can delay, slow, or prevent development of the corresponding disease or condition, or at least some symptoms of that disease.

Oligonucleotide Modifications and Synthesis

As indicated in the Summary above, modified oligonucleotides are useful in this invention. Such modified oligonucleotides include, for example, oligonucleotides containing modified backbones or non-natural internucleoside linkages. Oligonucleotides having modified backbones include those that retain a phosphorus atom in the backbone and those that do not have a phosphorus atom in the backbone.

Such modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, carboranyl phosphate and borano-phosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity typically include a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Preparation of Oligonucleotides with Phosphorus-Containing linkages as indicated above are described, for example, in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is incorporated by reference herein in its entirety.

Some exemplary modified oligonucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Particularly advantageous are backbone linkages that include one or more charged moieties. Examples of U.S. patents describing the preparation of the preceding oligonucleotides include U.S. Pat. Nos. 5,034,506; 5,166,315; 5,185,444; 5,214,134; 5,216,141; 5,235,033; 5,264,562; 5,264,564; 5,405,938; 5,434,257; 5,466,677;

5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is incorporated by reference herein in its entirety.

Modified oligonucleotides may also contain one or more substituted sugar moieties. For example, such oligonucleotides can include one of the following 2'-modifications: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl, or 2'-O—(O-carboran-1-yl)methyl. Particular examples are $O[(CH_2)_nO]_mCH_3$, $O(CH_2)$ ~$OCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to 10. Other exemplary oligonucleotides include one of the following 2'-modifications: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, a reporter group, an intercalator, a group for improving the pharmacokinetic properties of an oligonucleotide, or a group for improving the pharmacodynamic properties of an oligonucleotide. Examples include 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group; 2'-dimethyl-laminooxyethoxy, i.e., a $O(CH_2)_2ON(CH_3)_2$ group, also known as 2'-DMAOE; and 2'-dimethylaminoethoxyethoxy (also known as 2'-O-dimethylaminoethoxyethyl or 2'-DMAEOE), i.e., 2'-O—$CH_2$—O—$CH_2$—$N(CH_3)_2$.

Other modifications include Locked Nucleic Acids (LNAs) in which the 2'-hydroxyl group is linked to the 3' or 4' carbon atom of the sugar ring thereby forming a bicyclic sugar moiety. The linkage can be a methelyne (—$CH_2$—)~ group bridging the 2' oxygen atom and the 4' carbon atom wherein n is 1 or 2. LNAs and preparation thereof are described in WO 98/39352 and WO 99/14226, which are incorporated herein by reference in their entireties.

Other modifications include sulfur-nitrogen bridge modifications, such as locked nucleic acid as described in Orum et al. (2001) *Curr. Opin. Mol. Ther.* 3:239-243.

Other modifications include 2'-methoxy (2'-O—$CH_3$), 2'-methoxyethyl (2'O—$CH_2$—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. Similar modifications may also be made at other positions on the oligonucleotide, particularly the 3' position of the sugar on the 3' terminal nucleotide or in 2'-5' linked oligonucleotides and the 5' position of the 5' terminal nucleotide. Oligonucleotides may also have sugar mimetics such as cyclobutyl moieties in place of the pentofuranosyl sugar. Exemplary U.S. patents describing the preparation of such modified sugar structures include, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is incorporated by reference herein in its entirety.

Still other modifications include an ON concatemer consisting of multiple oligonucleotide sequences joined by a linker(s). The linker may, for example, consist of modified nucleotides or non-nucleotide units. In some embodiments, the linker provides flexibility to the ON concatemer. Use of such ON concatemers can provide a facile method to synthesize a final molecule, by joining smaller oligonucleotide building blocks to obtain the desired length. For example, a 12 carbon linker (C12 phosphoramidite) can be used to join two or more ON concatemers and provide length, stability, and flexibility.

As used herein, "unmodified" or "natural" bases (nucleobases) include the purine bases adenine (A) and guanine (G), and the pyrimidine bases thymine (T), cytosine (C) and uracil (U). Oligonucleotides may also include base modifications or substitutions. Modified bases include other synthetic and naturally-occurring bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl(—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Additional modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further nucleobases include those described in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Another modification includes phosphorodithioate linkages. Knowing that phosphorodithioate ODNs (PS2-ODNs) and PS-ODNs have a similar binding affinity to proteins (Tonkinson et al. (1994) *Antisense Res. Dev.* 4:269-278) (Cheng et al. (1997) *J. Mol. Recogn.* 10:101-107) and knowing that a possible mechanism of action of ODNs is binding to viral proteins, it could be desirable to include phosphorodithioate linkages on the antiviral ODNs described in this invention.

Another approach to modify ODNs is to produce stereodefined or stereo-enriched ODNs as described in Yu at al (2000) *Bioorg. Med. Chem.* 8:275-284 and in Inagawa et al. (2002) *FEBS Lett.* 25:48-52. ODNs prepared by conventional methods consist of a mixture of diastereomers by virtue of the asymmetry around the phosphorus atom involved in the internucleotide linkage. This may affect the stability of the binding between ODNs and viral components such as viral proteins. Previous data showed that protein binding is significantly stereo-dependent (Yu et al.). Thus, using stereodefined or stereo-enriched ODNs could improve their protein binding properties and improve their antiviral efficacy.

The incorporation of modifications such as those described above can be utilized in many different incorporation patterns and levels. That is, a particular modification need not be included at each nucleotide or linkage in an oligonucleotide, and different modifications can be utilized in combination in a single oligonucleotide, or even in a single nucleotide.

Oligonucleotide Synthesis

The present oligonucleotides can by synthesized using methods known in the art. For example, unsubstituted and substituted phosphodiester (P=O) oligonucleotides can be synthesized on an automated DNA synthesizer (e.g., Applied Biosystems model 380B) using standard phosphoramidite chemistry with oxidation by iodine. Phosphorothioates (P=S) can be synthesized as for the phosphodiester oligonucleotides except the standard oxidation bottle can be replaced by 0.2 M solution of 311-1,2-benzodithiole-3-one 1,1-dioxide in acetonitrile for the step-wise thioation of the phosphite linkages. The thioation wait step can be increased to 68 sec, followed by the capping step. After cleavage from the CPG column and deblocking in concentrated ammonium hydroxide at 55° C. (18 h), the oligonucleotides can be purified by precipitating twice with 2.5 volumes of ethanol from a 0.5 M NaCl solution.

Phosphinate oligonucleotides can be prepared as described in U.S. Pat. No. 5,508,270; alkyl phosphonate oligonucleotides can be prepared as described in U.S. Pat. No. 4,469,863; 3'-Deoxy-3'-methylene phosphonate oligonucleotides can be prepared as described in U.S. Pat. Nos. 5,610,289 and 5,625,050; phosphoramidite oligonucleotides can be prepared as described in U.S. Pat. No. 5,256,775 and U.S. Pat. No. 5,366,878; alkylphosphonothioate oligonucleotides can be prepared as described in published PCT applications PCT/US94/00902 and PCT/US93/06976 (published as WO 94/17093 and WO 94/02499, respectively); 3'-Deoxy-3'-amino phosphoramidate oligonucleotides can be prepared as described in U.S. Pat. No. 5,476,925; Phosphotriester oligonucleotides can be prepared as described in U.S. Pat. No. 5,023,243; borano phosphate oligonucleotides can be prepared as described in U.S. Pat. Nos. 5,130,302 and 5,177,198; methylenemethylimino linked oligonucleotides, also identified as MMI linked oligonucleotides, methylenedimethylhydrazo linked oligonucleotides, also identified as MDH linked oligonucleotides, and methylenecarbonylamino linked oligonucleotides, also identified as amide-3 linked oligonucleotides, and methyleneaminocarbonyl linked oligonucleotides, also identified as amide-4 linked oligonucleosides, as well as mixed backbone compounds having, for instance, alternating MMI and P=O or P=S linkages can be prepared as described in U.S. Pat. Nos. 5,378,825, 5,386,023, 5,489,677, 5,602,240 and 5,610,289; formacetal and thioformacetal linked oligonucleotides can be prepared as described in U.S. Pat. Nos. 5,264,562 and 5,264,564; and ethylene oxide linked oligonucleotides can be prepared as described in U.S. Pat. No. 5,223,618. Each of the cited patents and patent applications is incorporated by reference herein in its entirety.

Oligonucleotide Formulations and Pharmaceutical Compositions

The present oligonucleotides can be prepared in an oligonucleotide formulation or pharmaceutical composition. Thus, the present oligonucleotides may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Exemplary United States patents that describe the preparation of such uptake, distribution and/or absorption assisting formulations include, for example, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is incorporated herein by reference in its entirety.

The oligonucleotides, formulations, and compositions of the invention include any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular embodiments, prodrug versions of the present oligonucleotides are prepared as SATE [(S-acetyl-2-thioethyl)phosphate] derivatives according to the methods disclosed in Gosselin et al., WO 93/24510 and in Imbach et al., WO 94/26764 and U.S. Pat. No. 5,770,713, which are hereby incorporated by reference in their entireties.

The term "pharmaceutically acceptable salts" refers to physiologically and pharmaceutically acceptable salts of the present compounds: i.e., salts that retain the desired biological activity of the parent compound and do not impart undesired toxicological effects thereto. Many such pharmaceutically acceptable salts are known and can be used in the present invention.

For oligonucleotides, useful examples of pharmaceutically acceptable salts include but are not limited to salts formed with cations such as sodium, potassium, ammonium, magnesium, calcium, polyamines such as spermine and spermidine, etc.; acid addition salts formed with inorganic acids, for example hydrochloric acid, hydrobromic acid, sulfuric acid, phosphoric acid, nitric acid and the like; salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and salts formed from elemental anions such as chlorine, bromine, and iodine.

The present invention also includes pharmaceutical compositions and formulations which contain the antiviral oligonucleotides of the invention. Such pharmaceutical compositions may be administered in a number of ways depending upon whether local or systemic treatment is desired and upon the area to be treated. For example, administration may be topical (including ophthalmic and to mucous membranes including vaginal and rectal delivery); pulmonary, e.g., by inhalation or insufflation of powders or aerosols, including by nebulizer; intratracheal; intranasal; epidermal and transdermal; oral; or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, laurie acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Exemplary surfactants include fatty acids and/or esters or salts thereof, bile acids and/or salts thereof. Exemplary bile acids/salts include chenodeoxycholic acid (CDCA) and ursodeoxychenedeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Exemplary fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/ salts. A particularly preferred combination is the sodium salt of lauric acid, capric acid and UDCA. Further exemplary penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses, and starches. Particularly advantageous complexing agents include chitosan, N-trimethylchitosan, poly-L-lysine, polyhistidine, polyorithine, polyspermines, protamine, polyvinylpyridine, poly-thiodiethylamino-methylethylene P(TDAE), polyaminostyrene (e.g. p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG).

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaking the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The formulations and compositions of the present invention may be prepared and formulated as emulsions. Emulsions are typically heterogenous systems of one liquid dispersed in another in the form of droplets usually exceeding 0.1 µm in diameter. (Idson, in *Pharmaceutical Dosage Forms*, Lieberman, Rieger and Banker (lids.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et at., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety.

When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid, Antioxidants are also commonly added to emulsion formulations to prevent deterioration of the formulation Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically micro-emulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggre-* gate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385-1390; Ritschet, *Met/i. Find. Exp. Clin. PharmacoL*, 1993, 13, 205). Micro-emulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et at., *Pharmaceutical Research*, 1994, 11, 1385; Ho at al., *J. Pharm. Set*, 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92).

Liposomes

There are many organized surfactant structures besides microemulsions that have been studied and used for the formulation of drugs. These include monolayers, micelles, bilayers and vesicles. Vesicles offer specificity and extended duration of action for drug delivery. Thus, as used herein, the term "liposome" refers to a vesicle composed of amphiphilic lipids arranged in a spherical bilayer or bilayers, i.e., liposomes are unilamellar or multilamellar vesicles which have a membrane formed from a lipophilic material and an aqueous interior. The aqueous portion typically contains the composition to be delivered. In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores. Additional factors for liposomes include the lipid surface charge, and the aqueous volume of the liposomes.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245).

For topical administration, there is evidence that liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin. Compounds including analgesics, antibodies, hormones and high-molecular weight DNAs have been administered to the skin, generally resulting in targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et at., *Biochem. Biophys. Res. Commun.*, 1987, 147, 980-985).

Liposomes which are pH-sensitive or negatively-charged, entrap DNA rather than complex with it. Since both the DNA and the lipid are similarly charged, repulsion rather than complex formation occurs. The DNA is thus entrapped in the aqueous interior of these liposomes. pH-sensitive liposomes have been used, for example, to deliver DNA encoding the thymidine kinase gene to cell monolayers in culture (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et at., *Journal of Drug Targeting*, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasone™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et at. *S. T. P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome include one or more glycolipids, such as monosialoganglioside $G_{M1}$, or is derivatized with one or more hydrophilic polymers, such as a polyethylene glycol (PEG) moiety. Without being bound by any particular theory, it is believed that for sterically stabilized liposomes containing gangliosides, sphingomyelin, or PEG-derivatized lipids, the increase in circulation half-life of these sterically stabilized liposomes is due to a reduced uptake into cells of the reticuloendothelial system (RES) (Allen et at., *FEBS Lett.*, 1987, 223, 42; Wu et al., *Cancer Research*, 1993, 53, 3765).

Various liposomes that include one or more glycolipids have been reported in Papahadjopoulos et al., *Ann. N.Y. Acad. Sci.*, 1987, 507, 64 (monosiatoganglioside $G_{M1}$, galactocerebroside sulfate and phosphatidylinositol); Gabizon et at., *Proc. Natl. Acad. Sci. USA.*, 1988, 85, 6949; Allen et al., U.S. Pat. No. 4,837,028 and International Application Publication WO 88/04924 (sphingomyelin and the ganglioside $G_{M1}$ or a galactocerebroside sulfate ester); Webb et al., U.S. Pat. No. 5,543,152 (sphingomyelin); Lim et al., WO 97/13499 (1,2-sn-dimyristoylphosphatidylcholine).

Liposomes that include lipids derivatized with one or more hydrophilic polymers, and methods of preparation are described, for example, in Sunamoto et al., *Bull. Chem. Soc. Jpn.*, 1980, 53, 2778 (a nonionic detergent, $2C_{12}15G$, that contains a PEG moiety); Illum et al., *FEBS Let*, 1984, 167, 79 (hydrophilic coating of polystyrene particles with polymeric glycols); Sears, U.S. Pat. Nos. 4,426,330 and 4,534,899 (synthetic phospholipids modified by the attachment of carboxylic groups of polyalkylene glycols (e.g., PEG)); Klibanov et al., *FEBS Lett*, 1990, 268, 235 (phosphatidylethanolamine (PE) derivatized with PEG or PEG stearate); Blume et al., *Biochimica et Biophysica Acta*, 1990, 1029, 91 (PEG-derivatized phospholipids, e.g., DSPE-PEG, formed from the combination of distearoylphosphatidylethanolamine (DSPE) and PEG); Fisher, European Patent No. EP 0 445 131 B1 and WO 90/04384 (covalently bound PEG moieties on liposome external surface); Woodle et al., U.S. Pat. Nos. 5,013,556 and 5,356,633, and Martin et al., U.S. Pat. No. 5,213,804 and European Patent No. EP 0 496 813 B1 (liposome compositions containing 1-20 mole percent of PE derivatized with PEG); Martin et al., WO 91/05545 and U.S. Pat. No. 5,225,212 and in Zalipsky et al., WO 94/20073 (liposomes containing a number of other lipid-polymer conjugates); Choi et al., WO 96/10391 (liposomes that include PEG-modified ceramide lipids); Miyazaki et al., U.S. Pat. No. 5,540,935, and Tagawa et al., U.S. Pat. No. 5,556,948 (PEG-containing liposomes that can be further derivatized with functional moieties on their surfaces).

Liposomes that include nucleic acids have been described, for example, in Thierry et al., WO 96/40062 (methods for encapsulating high molecular weight nucleic acids in liposomes); Tagawa et al., U.S. Pat. No. 5,264,221 (protein-bonded liposomes containing RNA); Rahman et al., U.S. Pat. No. 5,665,710 (methods of encapsulating oligodeoxynucleotides in liposomes); Love et al., WO 97/04787 (liposomes that include antisense oligonucleotides).

Another type of liposome, transfersomes are highly deformable lipid aggregates which are attractive for drug delivery vehicles. (Cevc et al., 1998, *Biochim Biophys Acta.* 1368(2):201-15.) Transfersomes may be described as lipid droplets which are so highly deformable that they can penetrate through pores which are smaller than the droplet. Transfersomes are adaptable to the environment in which they are used, for example, they are shape adaptive, self-repairing, frequently reach their targets without fragmenting, and often self-loading. Transfersomes can be made, for example, by adding surface edge-activators, usually surfactants, to a standard liposomal composition.

Surfactants

Surfactants are widely used in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants are widely used in pharmaceutical and cosmetic products and are usable over a wide range of pH values, and with typical HLB values from 2 to about 18 depending on structure. Nonionic surfactants include nonionic esters such as ethylene glycol esters, propylene glycol esters, glyceryl esters, polyglyceryl esters, sorbitan esters, sucrose esters, and ethoxylated esters; and nonionic alkanolamides and ethers such as fatty alcohol ethoxylates, propoxylated alcohols, and ethoxylated/propoxylated block polymers are also included in this class. The polyoxyethylene surfactants are the most commonly used members of the nonionic surfactant class.

Surfactant molecules that carry a negative charge when dissolved or dispersed in water are classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isothionates, acyl laurates and sulfosuccinates, and phosphates. The alkyl sulfates and soaps are the most commonly used anionic surfactants.

Surfactant molecules that carry a positive charge when dissolved or dispersed in water are classified as cationic. Cationic surfactants include quaternary ammonium salts and ethoxylated amines, with the quaternary ammonium salts used most often.

Surfactant molecules that can carry either a positive or negative charge are classified as amphoteric. Amphoteric surfactants include acrylic acid derivatives, substituted alkylamides, N-alkylbetaines and phosphatides.

The use of surfactants in drug products, formulations and in emulsions has been reviewed in Rieger, in *Pharmaceutical Dosage Forms*, Marcel Dekker, Inc., New York, N.Y., 1988, p. 285).

Penetration Enhancers

In some embodiments, penetration enhancers are used in or with a composition to increase the delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating nonsurfactants (Lee et al., *Critical Reviews in Therapeutic Drug Carrier Systems*, 1991, p. 92). Each of these classes of penetration enhancers is described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. These penetration enhancers include, for example, sodium lauryl sulfate, polyoxyethylene-9-lauryl ether and polyoxyethylene-20-cetyl ether) (Lee et at., *Critical Reviews in Therapeutic Drug Carrier Systems*, 1991, p. 92); and perfluorochemical emulsions, such as FC-43. Takahashi et al., *J. Pharm. Pharmacol.*, 1988, 40, 252), each of which is incorporated herein by reference in its entirety.

Fatty acids: Various fatty acids and their derivatives which act as penetration enhancers include, for example, oleic acid, lauric acid, capric acid (n decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and diglycerides thereof (i.e., oleate, laurate, caprate, myristate, palmitate, stearate, linoleate, etc.) (Lee et al., *Critical Reviews in Therapeutic Drug Carrier Systems*, 1991, p. 92; Muranishi, *Critical Reviews in Therapeutic Drug Carrier Systems*, 1990, 7, 1-33; E I Hariri et al., *J. Pharm. Pharmacol.*, 1992, 44, 651-654), each of which is incorporated herein by reference in its entirety.

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782-783; Muranishi, *Critical Reviews in Therapeutic Drug Carrier Systems*, 1990, 7, 1-33; Yamamoto et al., *J. Pharm. Exp. Ther.*, 1992, 263, 25; Yamashita et al., *J. Pharm. Sci.*, 1990, 79, 579-583).

Chelating Agents: In the present context, chelating agents can be regarded as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315-339). Without limitation, chelating agents include disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1-33; Buur et al., *J. Control Rel.*, 1990, 14, 43-51).

Non-chelating non-surfactants: As used herein, non-chelating non-surfactant penetration enhancing compounds are compounds that do not demonstrate significant chelating agent or surfactant activity, but still enhance absorption of oligonucleotides through the alimentary mucosa (Muranishi, *Critical Reviews in Therapeutic Drug Carrier Systems*, 1990, 7, 1-33). Examples of such penetration enhancers include unsaturated cyclic ureas, 1-alkyl- and 1-alkenylazacyclo-alkanone derivatives (Lee et al., *Critical Reviews in Therapeutic Drug Carrier Systems*, 1991, page 92); and nonsteroidal anti-inflammatory agents such as diclofenac sodium, indomethacin and phenylbutazone (Yamashita et al., *J. Pharm. Pharmacol.*, 1987, 39, 621-626).

Agents that enhance uptake of oligonucleotides at the cellular level may also be added to the pharmaceutical and other compositions and formulations of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, often with an excess of the latter substance, can result in a substantial reduction of the amount of nucleic acid recovered in the liver, kidney or other extracirculatory reservoirs. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2-disulfonic acid (Miyao et al., *Antisense Res. Dev.*, 1995, 5, 115-121; Takakura et al., *Antisense & NucL Acid Drug Dev.*, 1996, 6, 177-183), each of which is incorporated herein by reference in its entirety.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal, and is typically liquid or solid. A pharmaceutical carrier is generally selected to provide for the desired bulk, consistency, etc., when combined with a nucleic acid and the other components of a given pharmaceutical composition, in view of the intended administration mode. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Other Pharmaceutical Composition Components

The present compositions may additionally contain other components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran, and/or stabilizers.

Certain embodiments of the invention provide pharmaceutical compositions containing (a) one or more antiviral oligonucleotides and (b) one or more other chemotherapeutic agents which function by a different mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin, and diethylstilbestrol (DES). See, generally, *The Merck Manual of Diagnosis and Therapy*, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-EU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to Ribavirin, cidofovir, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499-2506 and 46-49, respectively). Other non-oligonucleotide chemotherapeutic agents are also within the scope of this invention. Two or more combined compounds may be used together or sequentially.

EXAMPLES

Example 1

Herpes Simplex Virus

Herpes simplex virus (HSV) affects a significant proportion of the human population. It was found in the present invention that random ODNs or ODN randomers inhibited the infectivity of viruses such as HSV. Using cellular HSV replication assays in VERO cells (susceptible to HSV-1 (strain KOS) and HSV-2 (strain MS2) infection) it was found that a single stranded PS-ODN complementary to the HSV origin of replication inhibited replication of HSV-1 and HSV-2. Surprisingly, control PS-ODNs complementary to human (343 ARS) and plasmid (pBR322/pUC) origins also inhibited viral infectivity. Experiments with random sequence PS-ODNs and PS-ODN randomers demonstrated that inhibition of viral infection increased with increasing ODN size. These data show that ONs are potent antiviral agents useful for therapeutic treatment of viral infection.

The inventors have theorized that a potential mechanism for blocking the spread of viruses such as HHVs was to prevent the replication of its DNA. With this in mind, phosphorothioate oligonucleotides (ODNs) complementary to the origin of replication of HSV-1 and HSV-2 were introduced into infected cells. These ODNs would cause DNA triplex formation at the viral origin of replication, blocking the association of necessary trans-acting factors and viral DNA replication. Surprising results are presented herein of these experiments which show that, in an experimental paradigm, the potency of ODNs in inhibiting viral infection increases as their size (length) increases.

Inhibition of HSV-1

The ability of PS-ODNs to inhibit HSV-1 is measured in a plaque reduction assay (PRA). Immortalized African Green Monkey kidney (VERO) cells are cultured at 37° C. and 5% $CO_2$ in MEM (minimal essential medium) plus 10% fetal calf serum supplemented with gentamycin, vancomycin and amphoterecin B. Cells are seeded in 12 well plates at a density which yields a confluent monolayer of cells after 4 days of growth. Upon reaching confluency, the media is changed to contain only 5% serum plus supplements as described above and cells are then exposed to HSV-1 (strain KOS, approximately 40-60 PFU total) in the presence of the test compound for 90 minutes. After viral exposure, the media is replaced with new "overlay" media containing 5% serum, 1% human immunoglobulins, supplements as described above and the test compound. Plaque counting is performed 3-4 days post infection following formalin fixation and cresyl violet staining of infected cultures.

All ONs (except where noted otherwise) were synthesized at the University of Calgary Core DNA Services lab. ONs (see table 1) are prepared on a 1 or 15 micromol synthesis scale, deprotected and desalted on a 50 cm Sephadex G-25 column. The resulting ONs are analyzed by UV shadowing gel electrophoresis and are determined to contain ~95% of the full length, n-1 and n-2 oligo and up to 5% of shorter oligo species (these are assumed to have random deletions). For random oligo synthesis, adenine, guanosine, cytosine and thymidine amidites are mixed together in equimolar quantities to maximize the randomness of incorporation at each position of the ODNs during synthesis.

Figure 2:
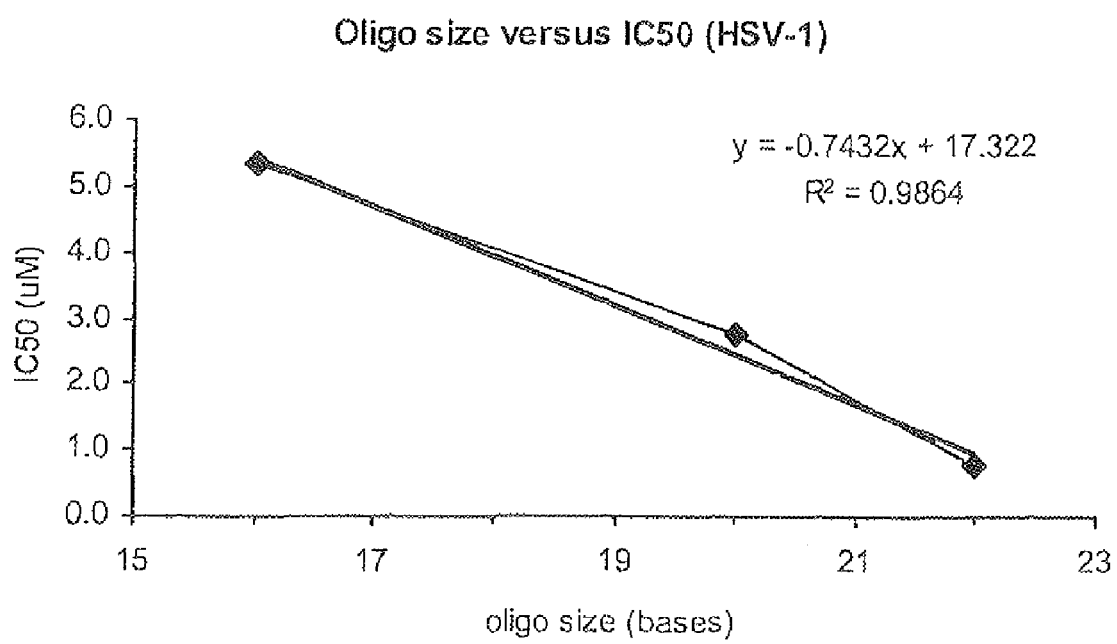
FIG. 2. Relationship between PS-ODN size and $IC_{50}$ against HSV-1. $IC_{50}$ values from FIG. 1 are plotted against the specific size of each PS-ODN tested in FIG. 1.
Figure 3A:
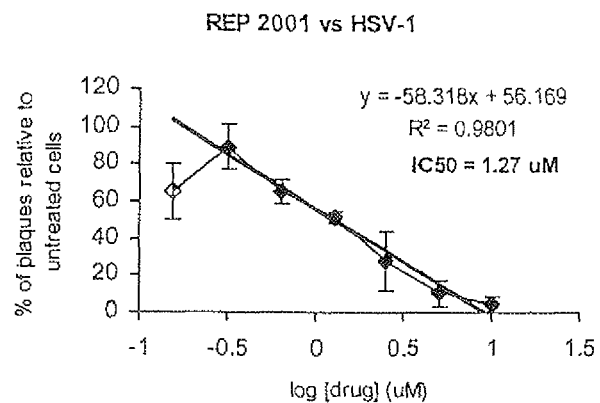
FIG. 3. Plaque reduction assay conducted in VERO cells using HSV-1 (strain KOS). Infected cells are treated with increasing concentrations of REP 2001 (a), REP 2002 (b) or REP 3003 (c), REP 2004 (d), REP 2005 (e), REP 2006 (f) and Acyclovir (g). $IC_{50}$ values calculated from linear regressions are reported in each graph.
Figure 3B:
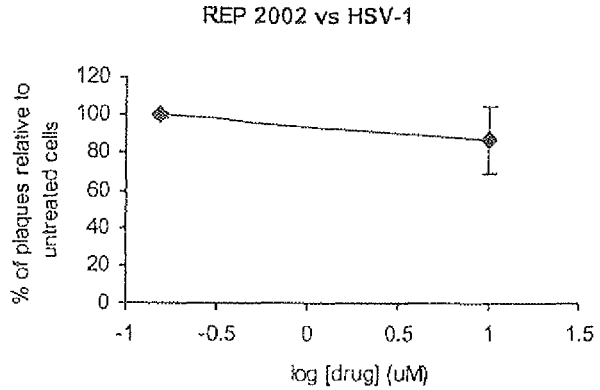
Figure 3C:
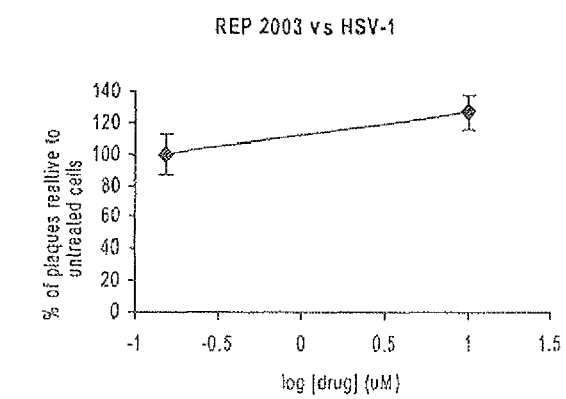
Figure 3D:
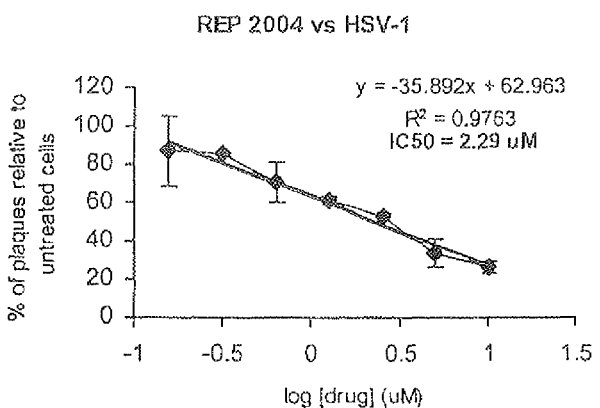
Figure 3E:
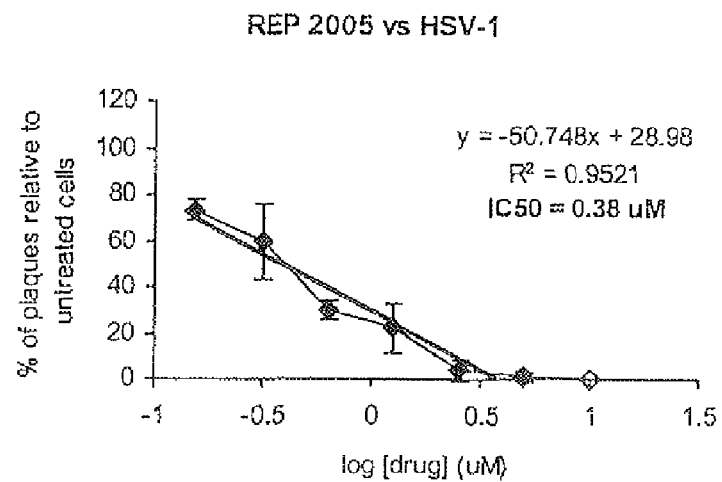
Figure 3F:
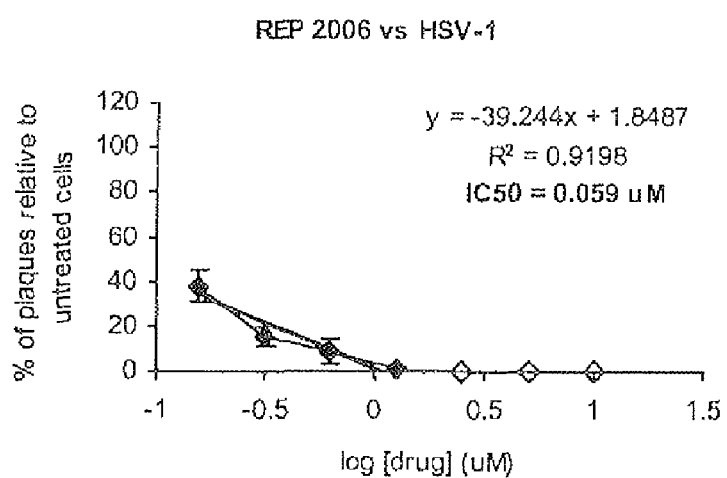
Figure 3G:
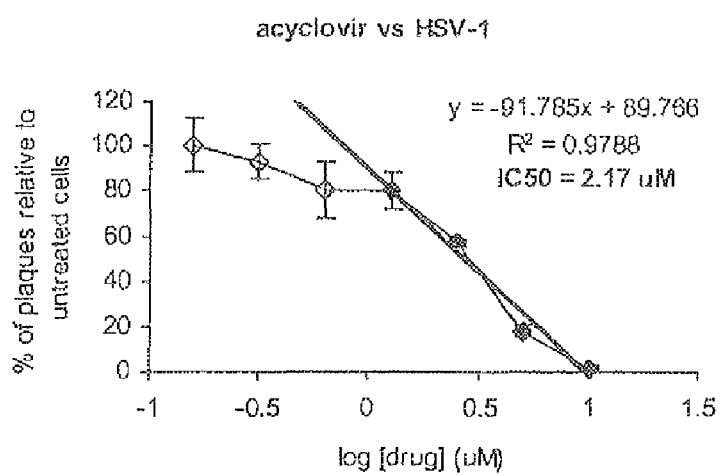

To test if PS-ODNs could inhibit HSV-1, REP 1001, 2001 and 3007 are tested in the HSV-1 PRA. It is expected that only REP 2001 will show any activity as this PS-ODN is directed against the origin of replication in HSV (the other two are directed against replication origins in humans and plasmids). However all three PS-ODNs showed anti-HSV-1 activity (see FIG. 1). Moreover, the potency of the anti-HSV-1 effect is dependent on the size of the oligo (see FIG. 2).

Figure 4:
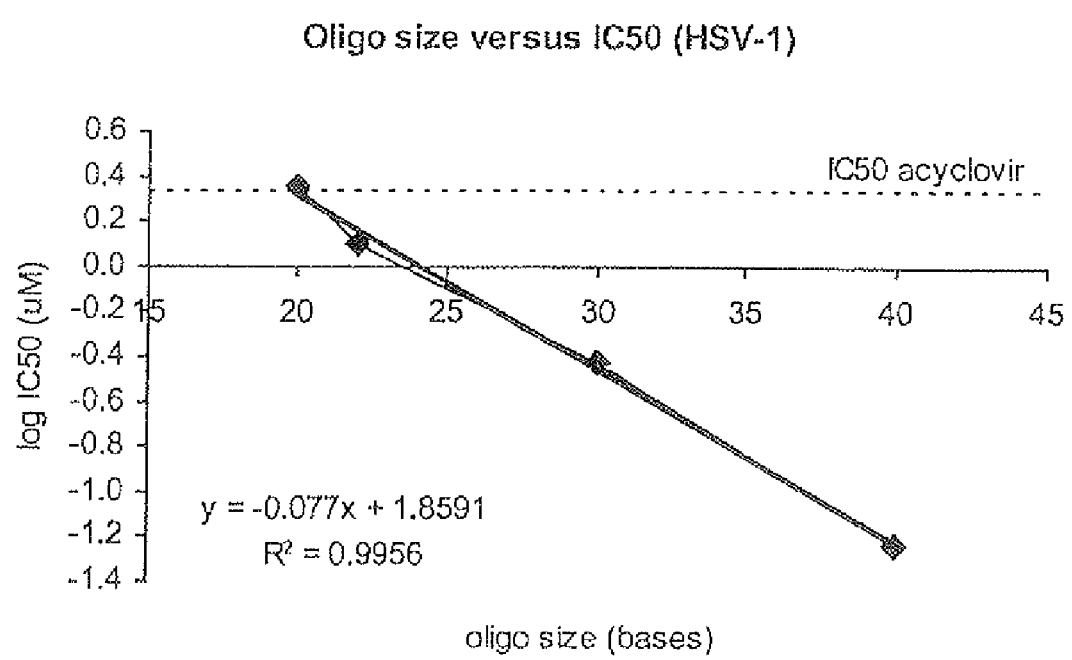
FIG. 4. Relationship between PS-ODN size and $IC_{50}$ against HSV-1. $IC_{50}$ values from FIG. 3 are plotted against the specific size of each PS-ODN tested in FIG. 3 which showed anti-HSV-1 activity. The $IC_{50}$ for Acyclovir is indicated for reference to a clinical correlate.
Figure 5A:
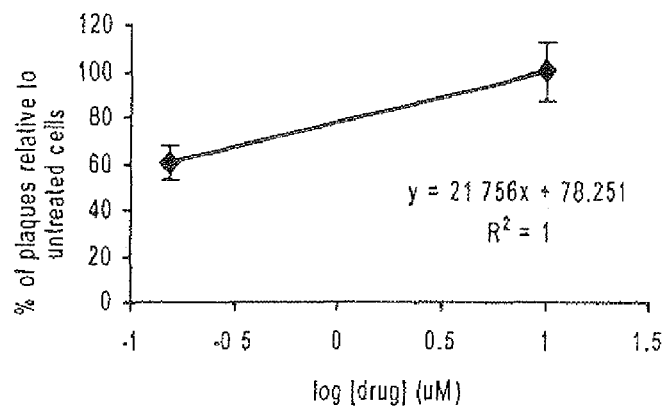
FIG. 5. Plaque reduction assay conducted in VERO cells using HSV-1 (strain KOS). A broad range of PS-ODN randomer sizes were tested in increasing concentrations; REP 2003 (a), REP 2009 (b), REP 2010 (c), REP 2011 (d), REP 2012 (e), REP 2004 (f), REP 2006 (g), REP 2007 (h) and REP 2008 (i). $IC_{50}$ values calculated from linear regressions are reported in each graph.
Figure 5B:
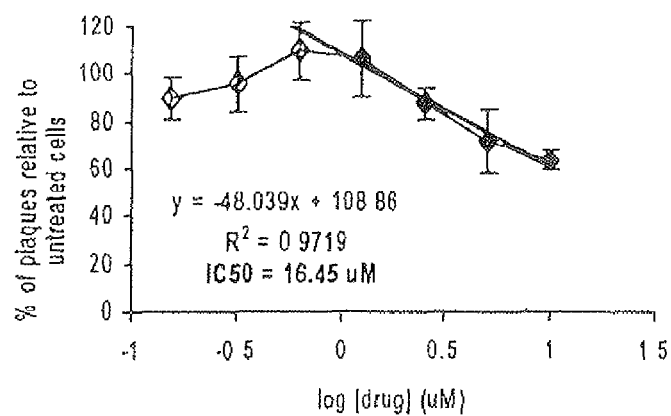
Figure 5C:
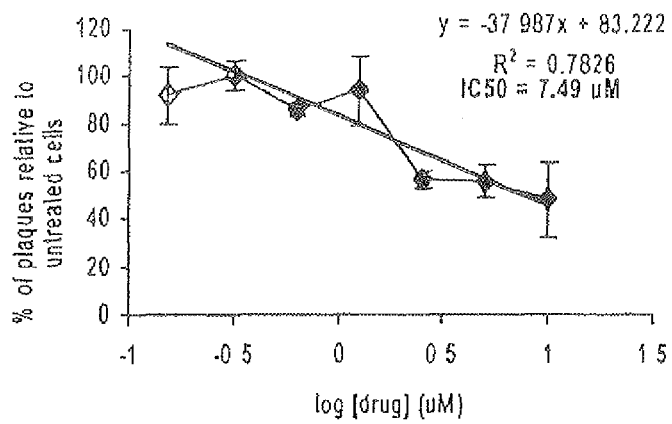
Figure 5D:
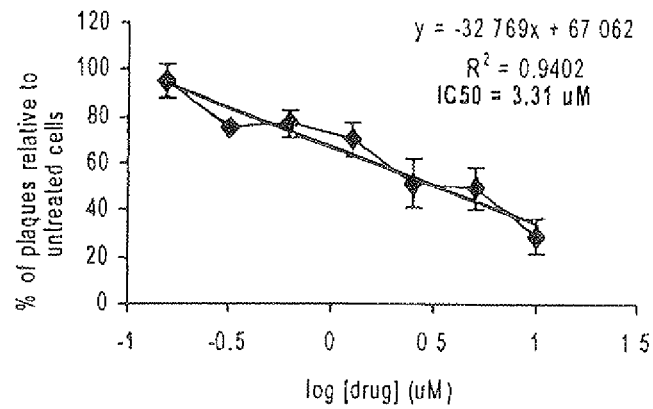
Figure 5E:
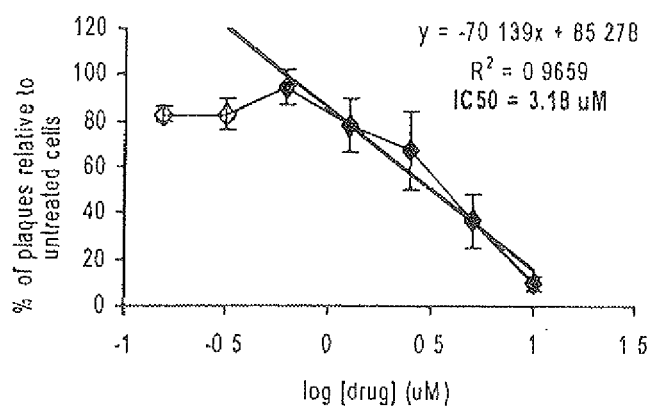
Figure 5F:
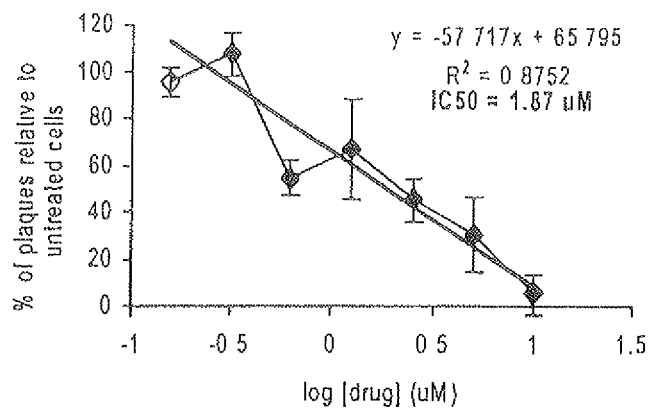
Figure 5G:
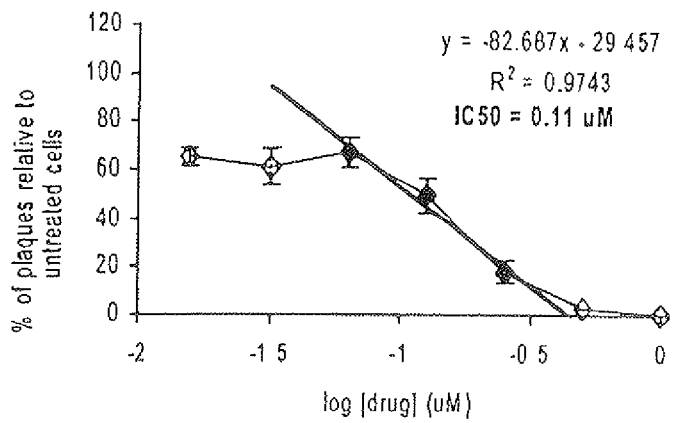
Figure 5H:
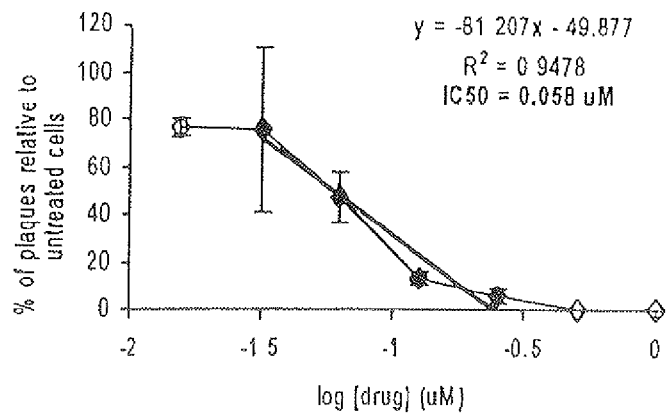
Figure 5I:
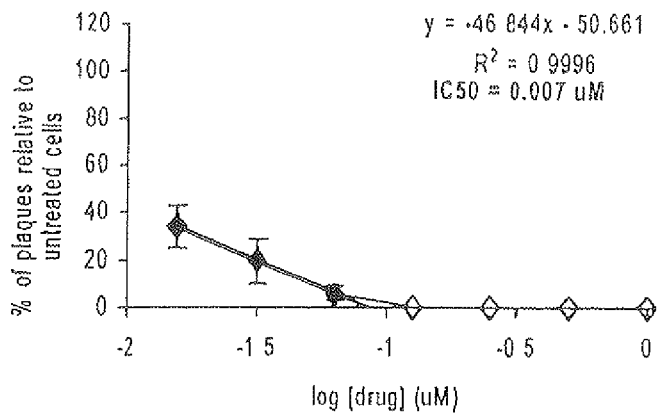

To confirm the size dependence and relative sequence independence of PS-ODNs on anti-HSV-1 activity, we tested PS-ODNs that vary in size (REP 2002, 2003, 2004, 2005 and 2006). These PS-ODNs are rendered inert with respect to sequence specific effects by synthesizing each base as a "wobble" (N) so that each PS-ODN actually represents a population of different random sequences with the same size, these PS-ODNs are termed "randomers". When these oligos are tested in the HSV-1 PRA, we find that oligos 10 bases or lower have no detectable anti-HSV-1 activity but as the size of the PS-ODN increases above 10 bases, the potency also increases ($IC_{50}$ decreases, see FIGS. 3 and 4). We also note that PS-ODNs greater than 20 bases had $IC_{50}$ values significantly lower than a clinically accepted anti-HSV-1 drug, acyclovir (see FIG. 4).

Figure 6:
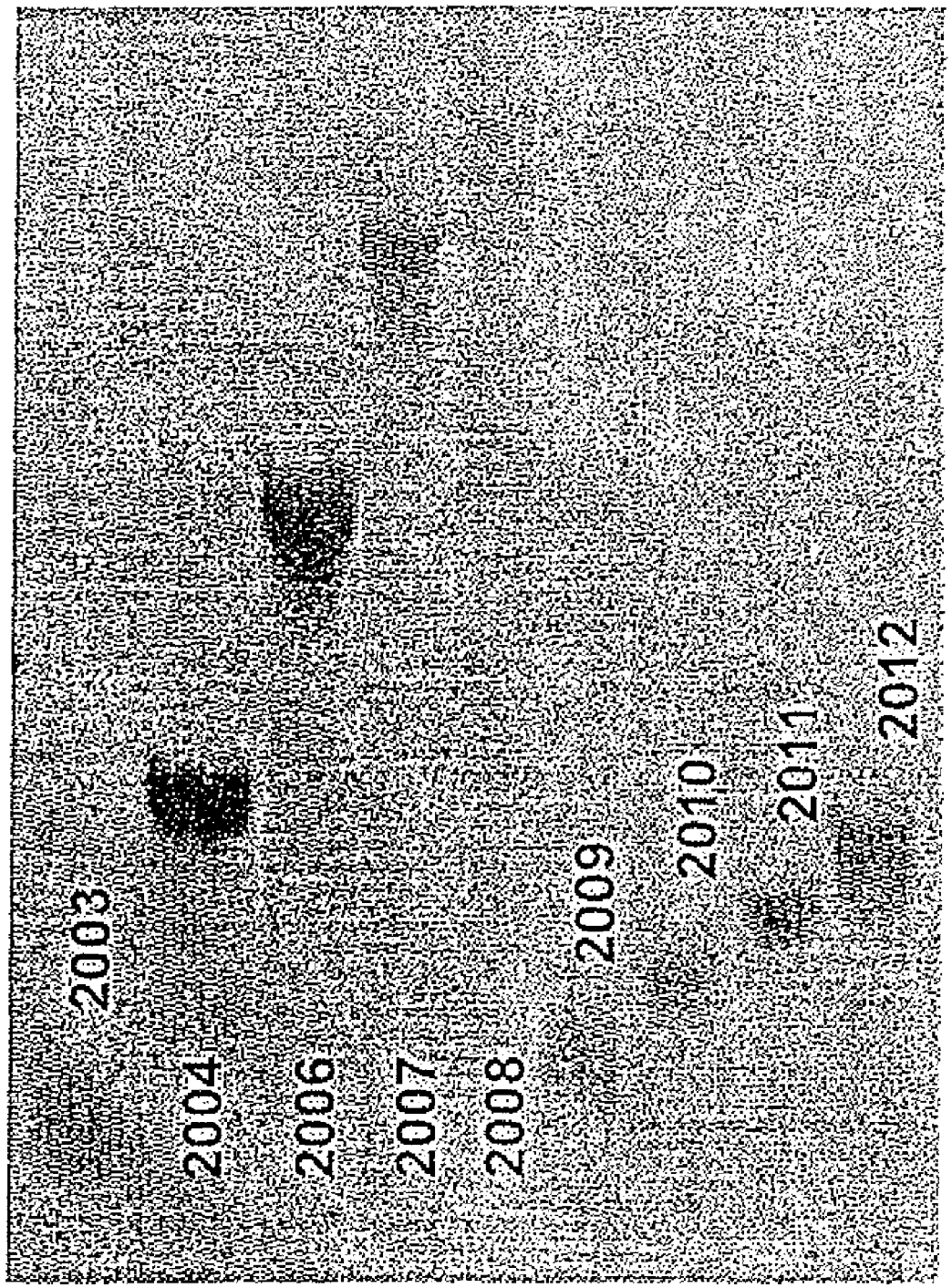
FIG. 6. UV backshadowing of PS-ODN randomers tested in FIG. 5 separated by acrylamide gel electrophoresis.
Figure 7:
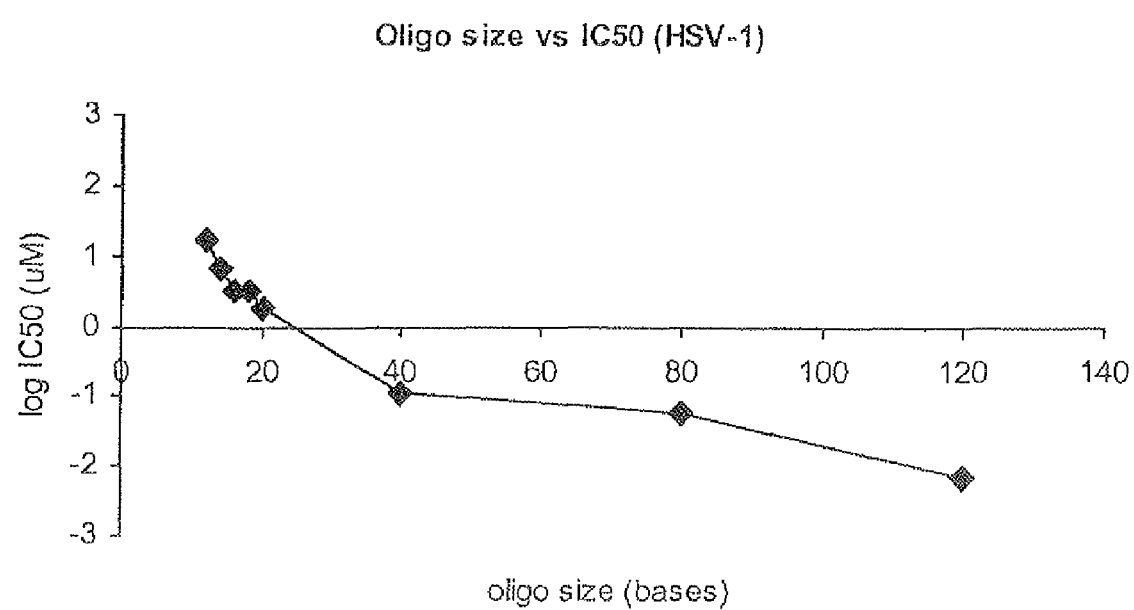
FIG. 7. Relationship between PS-ODN randomer size and $IC_{50}$ against HSV-1. $IC_{50}$ values from FIG. 5 are plotted against the specific size of each PS-ODN tested in FIG. 5 which showed anti-HSV-1 activity.
Figure 8A:
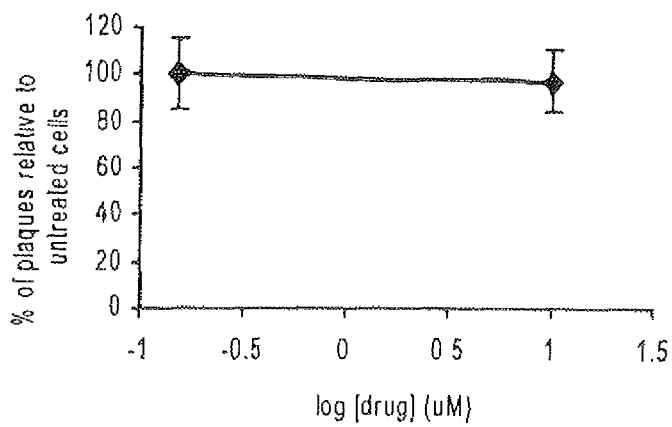
FIG. 8. Plaque reduction assay conducted in VERO cells using HSV-1 (strain KOS). Umodified ODNs, PS-ODNs with a random sequence and PS-ODNs targeting the start codon of HSV-1 IE110 were tested in increasing concentrations. REP 2013 (a), REP 2014 (b), REP 2015 (c), REP 2016 (d), REP 2017 (e), REP 2018 (f), REP 2019 (g), REP 2020 (h) and REP 2021 (i). $IC_{50}$ values calculated from linear regressions are reported in each graph.
Figure 8B:
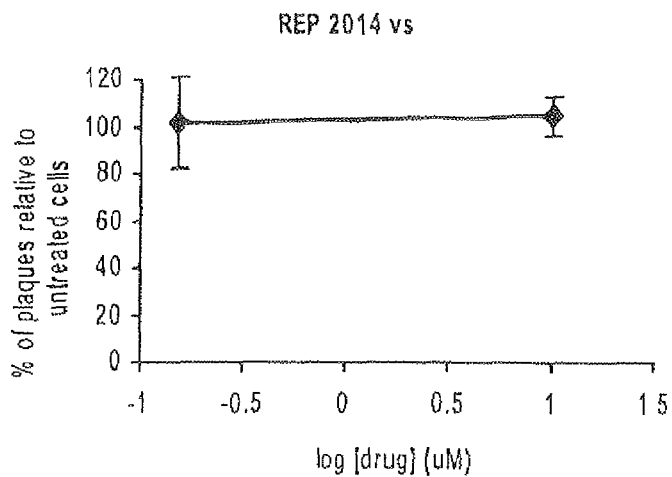
Figure 8C:
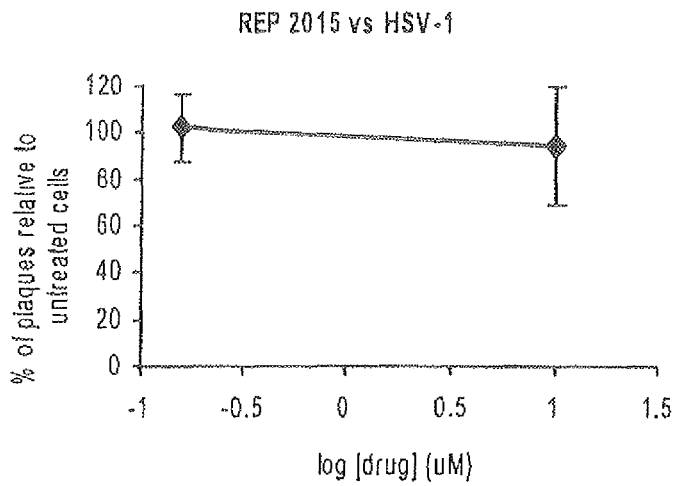
Figure 8D:
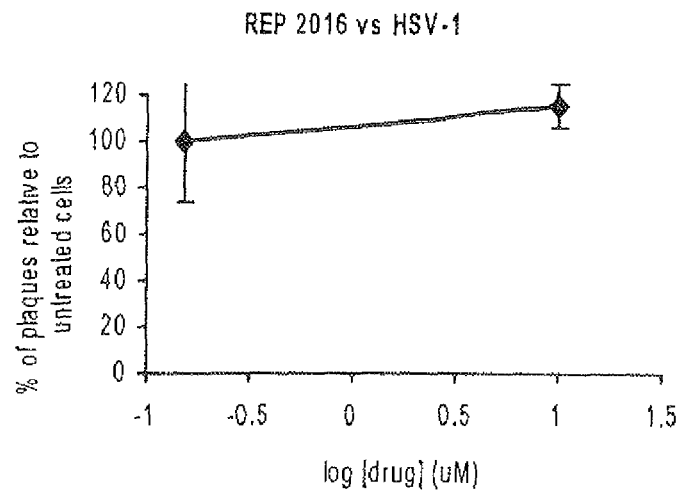
Figure 8E:
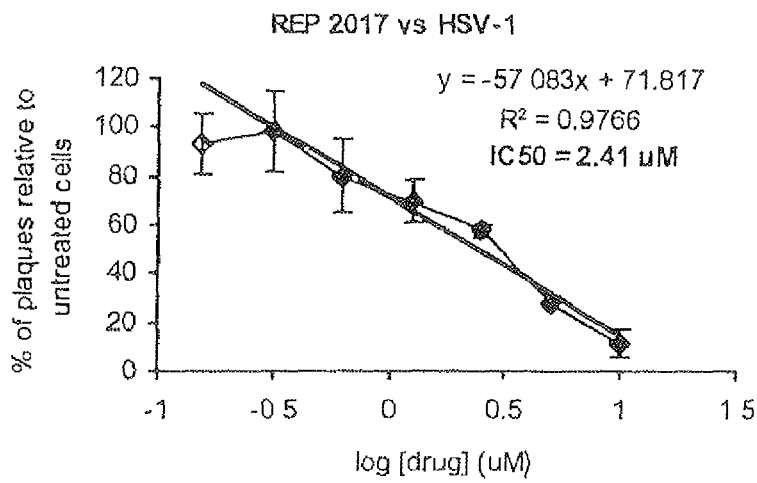
Figure 8F:
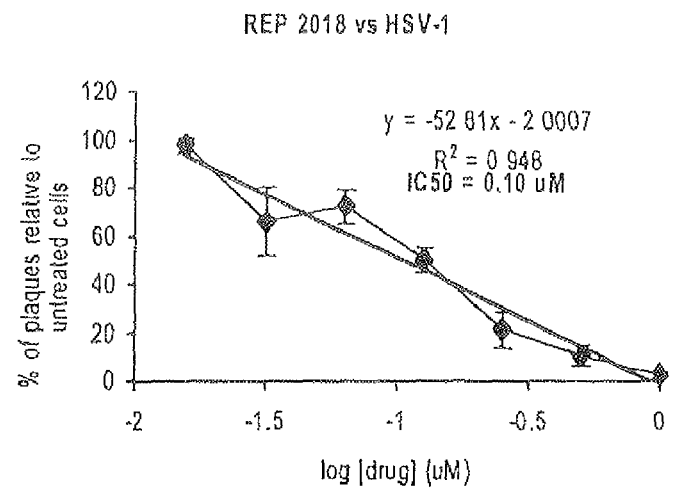
Figure 8G:
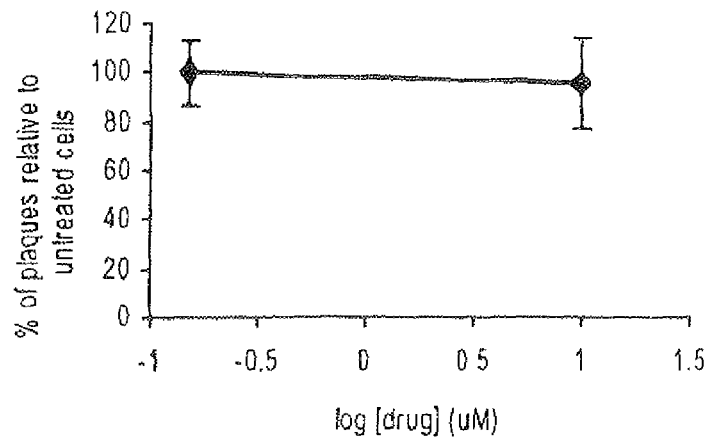
Figure 8H:
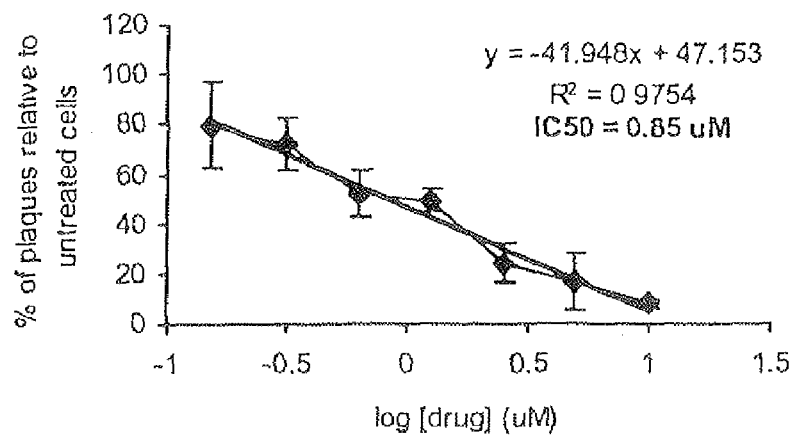
Figure 8I:
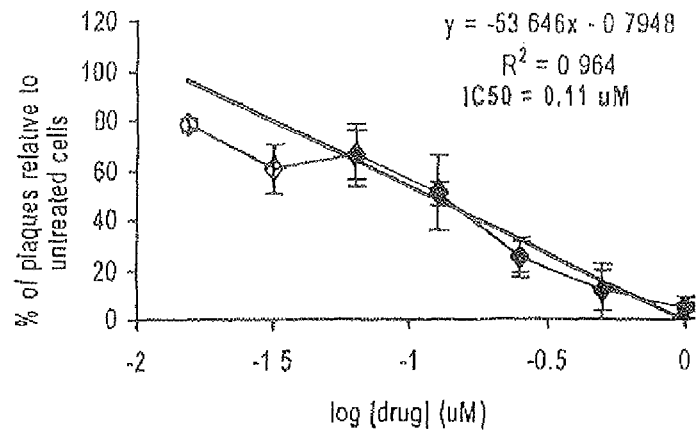

To better define the effective size range for PS-ODN anti-HSV-1 activity, we tested PS-ODN randomers covering a broader range of sizes from 10 to 120 bases (see FIGS. 5 and 6). We discovered that oligos 12 bases and larger have detectable anti-HSV-1 activity and that the efficacy against HSV-1 also increases with increased PS-ODN randomer length at least up to 120 bases. However, the increases in efficacy per base increase in size are smaller in PS-ODN randomers greater than 40 bases (see FIG. 7).

Figure 9:
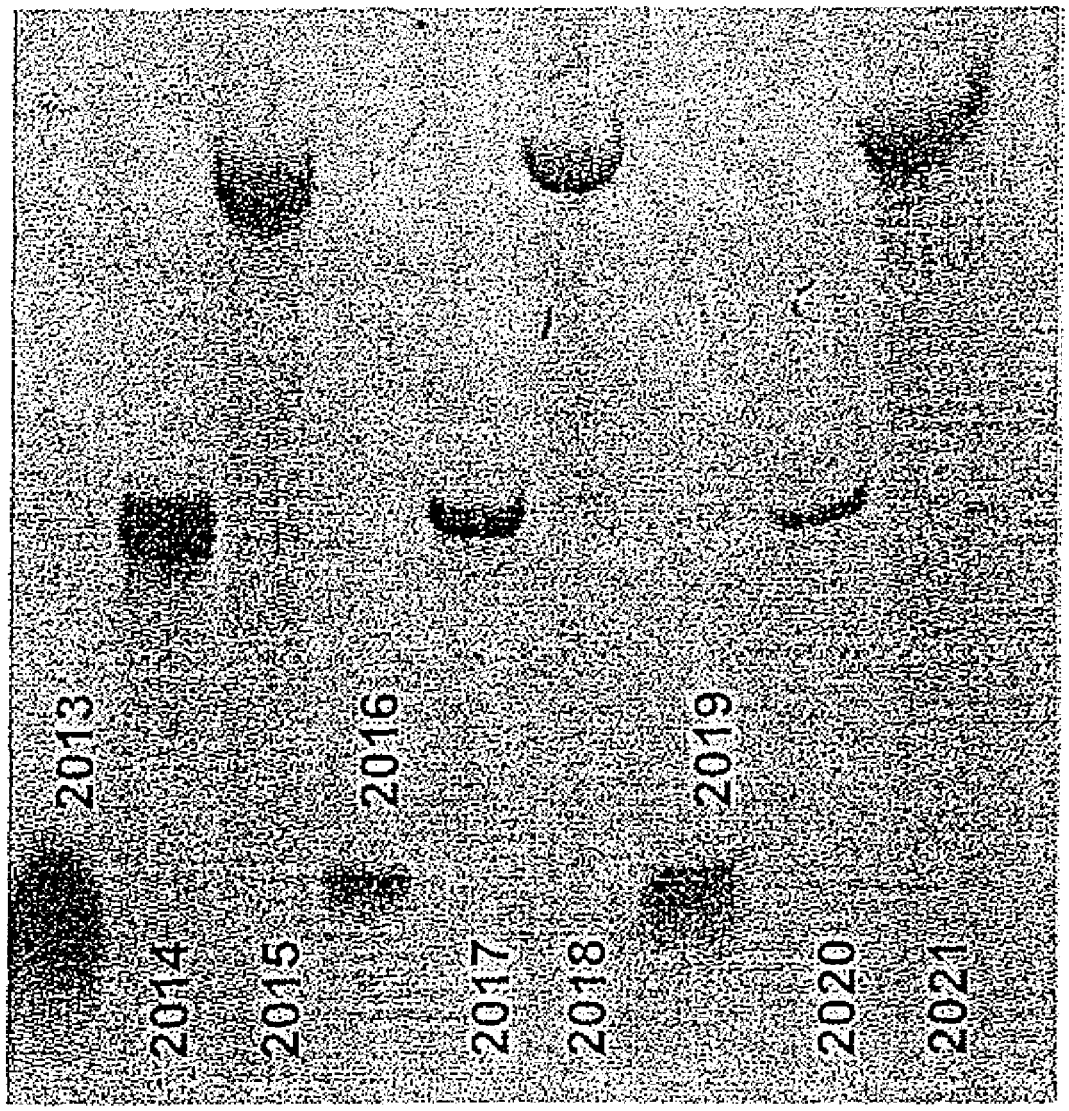
FIG. 9. UV backshadowing of PS-ODN randomers tested in FIG. 8 separated by acrylamide gel electrophoresis.

To compare the efficacy of non-PS-ODN randomers, a random sequence PS-ODN and a HSV-1 specific sequence PS-ODN, we tested these three types of modifications in ODNs 10, 20 and 40 bases in size (see FIGS. 8 and 9). Unmodified ODN randomers have no detectable anti-HSV-1 activity at tested sizes (see FIGS. 8a-c). Both random sequence and specific HSV-1 sequence PS-ODNs show size dependent anti-HSV-1 activity (no activity is observed at 10 bases for either of these modifications, see FIGS. 8d and g). A comparison of random sequence, specific HSV-1 sequence and randomer PS-ODNs (see FIG. 10) shows that for PS-ODNs 20 bases in length, there is an enhancement of anti-HSV-1 activity with the specific HSV-1 sequence but that at 40 bases in length, all modifications, whether randomer, random sequence or specific HSV-1 sequence were equally efficacious against HSV-1.

To the best of our knowledge, this is the first time IC50s for HSV-1 as low as 0.059 µM and 0.043 µM are reported for PS-ODNs.

Example 2

Inhibition of HSV-2

The ability of PS-ODNs to inhibit HSV-2 is measured by PRA. Immortalized African Green Monkey kidney (VERO) cells are cultured at 37° C. and 5% $CO_2$ in MEM plus 10% fetal calf serum supplemented with gentamycin, vancomycin and amphoterecin B. Cells are seeded in 12 well plates at a density which yields a confluent monolayer of cells after 4 days of growth. Upon reaching confluency, the media is changed to contain only 5% serum plus supplements as described above and cells are then exposed to HSV-2 (strain MS2, approximately 40-60 PFU total) in the presence of the test compound for 90 minutes. After viral exposure, the media is replaced with new "overlay" media containing 5% serum, 1% human immunoglobulins, supplements as described above and the test compound. Plaque counting is performed 3-4 days post infection following formalin fixation and cresyl violet staining of infected cultures.

To test if PS-ODNs could inhibit HSV-2, REP 1001, 2001 and 3007 are tested in the HSV-2 PRA. It is expected that only REP 2001 will show any activity as this PS-ODN is directed against the origin of replication in HSV-1/2 (the other two are directed against replication origins in humans and plasmids), however all three PS-ODNs showed anti-HSV-2 activity (see FIG. 12). Moreover, the potency of the anti-HSV-2 effect is dependent on the size of the PS-ODN and independent of the sequence (see FIG. 13).

To confirm the size dependence and sequence independence of PS-ODNs on anti-HSV-2 activity, we test PS-ODNs that vary in size (REP 2001, 2002, 2003, 2004, 2005 and 2006). These PS-ODNs are rendered inert with respect to sequence specific effects by synthesizing each base as a "wobble" (N) so that each PS-ODN actually represents a population of different random sequences with the same size, these PS-ODNs are termed "randomers". When these PS-ODNs are tested in the HSV-2 PRA, we find that PS-ODNs 10 bases or lower had no detectable anti-HSV-2 activity but as the size of the PS-ODN increases above 10 bases, the potency also increases ($IC_{50}$ decreases, see FIGS. 14 and 15). We also noted that PS-ODNs greater than 20 bases had $IC_{50}$ values significantly lower than a clinically accepted anti-HSV-2 drug, Acyclovir™ (see FIG. 15).

To the best of our knowledge, this is the first time an IC50 for HSV-2 as low as 0.012 µM has been reported for a PS-ODN.

To determine if non-specific sequence composition has an effect on ON antiviral activity, several PS-ODNs of equivalent size but differing in their sequence composition were tested for anti-HSV1 activity in the HSV-1 PRA. The PS-ODNs tested were REP 2006 (N20), REP 2028 (G40) (SEQ ID NO: 21), REP 2029 (A40) (SEQ ID NO: 20). REP 2030 (T40) (SEQ ID NO: 23) and REP 2031 (C40) (SEQ ID NO: 22). The IC50 values generated from the HSV-1 PRA (see FIG. 37) show that REP 2006 (N40) was clearly the most active of all sequences tested while REP 2029 (A40) (SEQ ID NO: 20) was the least active. We also note that, all the other PS-ODNs were significantly less active than N40 with their rank in terms of efficacy being N40>C40 (SEQ ID NO: 22)>T40>(SEQ ID NO: 23) A40 (SEQ ID NO: 20)>>G40 (SEQ ID NO: 21).

We also tested the efficacy of different PS ODNs having varying sequence composition with two different nucleotides (see FIG. 37b). The PS-ODN randomer (REP 2006) was significantly more efficacious against HSV-1 than AC20 (SEQ ID NO: 24)(REP 2055), TC20 (SEQ ID NO: 25) (REP 2056) or AG20 (SEQ ID NO: 26) (REP 2057) with their efficacies ranked as follows: N40>AG(20)(SEQ ID NO: 26)>AC(20) (SEQ ID NO: 24)>TC(20)(SEQ ID NO: 25). This data suggests that although the anti-viral effect is non-sequence complementary, certain non-specific sequence compositions (i.e. C40 (SEQ ID NO: 22) and N40) have the most potent anti-viral activity. We suggest that this phenomenon can be explained by the fact that, while retaining intrinsic protein binding ability, sequences like C40 (SEQ ID NO: 22), A40 (SEQ ID NO: 20), T40 (SEQ ID NO: 23) and G40 (SEQ ID NO: 21) bind fewer viral proteins with high affinity, probably due to some restrictive tertiary structure formed in these sequences. On the other hand, due to the random nature of N40, it retains its ability to bind with high affinity to a broad range of anti-viral proteins which contributes to its robust anti-viral activity.

Example 3

Inhibition of CMV

The ability of PS-ODNs to inhibit CMV is measured in a plaque reduction assay (PRA). This assay is identical to the assay used for testing anti-HSV-1 and anti-HSV-2 except that CMV (strain AD169) is used as the viral innoculum and human fibroblasts were used as cellular host.

To test the size dependence and sequence independence of PS-ODNs on anti-CMV activity, we test PS-ODN randomers that vary in size (see FIG. 16a, b). When these PS-ODNs are tested in the CMV PRA, we find that as the size of the PS-ODN increases, the potency also increases ($IC_{50}$ decreases, see FIG. 16c).

To more clearly elucidate the effective size range for PS-ODN anti-CMV activity, we tested PS-ODN randomers covering a broader range of sizes from 10 to 80 bases. We also included several clinically accepted small molecule CMV treatments (Gancyclovir, Foscarnet and Cidofovir) as well as 2 versions of a marketed antisense treatment for CMV retinitis, (Vitravene™; commercially available and synthesized by the University of Calgary) (see FIG. 17). We discovered that while increased PS-ODN randomer size leads to increased efficacy, this effect saturates at 40 bases (see FIG. 18). Moreover, the 20, 40 and 80 base PS-ODN randomers are all significantly more efficacious than any of the small molecule treatments tested (FIG. 17). In addition, 40 and 80 base PS-ODN randomers are more efficacious than Vitravene™.

To the best of our knowledge, this is the first time an IC50 for CMV as low as 0.067 µM has been reported for a PS-ODN.

Example 4

Inhibition of HIV-1

The ability of PS-ODN randomers to inhibit HIV-1 is measured by two different assays:

Cytopathic Effect (CPE)

Cytopathic effect is monitored using MTT dye to report the extent of cellular metabolism. Immortalized human lymphocyte (MT4) cells are cultured at 37° C. and 5% $CO_2$ in MEM plus 10% fetal calf serum supplemented with antibiotics. Cells are seeded in 96 well plates in media containing the appropriate test compound and incubated for 2 hours. After preincubation with the test compound, HIV-1 (strain NL 4-3) was added to the wells (0.0002 $TCID_{50}$/cell). After 6 days of additional incubation, CPE is monitored by MTT conversion. Cytotoxicity is measured by incubating the drugs for 6 days in the absence of viral inoculation. For transformation of MTT absorbance values into % survival, the absorbance of uninfected, untreated cells is set to 100% and the absorbance of infected, untreated cells is set to 0%.

Replication Assay (RA)

The ability of HIV to replicate is monitored in immortalized human embryonic kidney (293A) cells. These cells are cotransfected with two plasmids. One plasmid contains a recombinant wild type HIV-1 genome (NL 4-3) having its env gene disrupted by a luciferase expression cassette (identified as strain CNDO), the other plasmid contains the env gene from murine leukemia virus (MLV). These two plasmids provide all the protein factors in trans to produce a mature chimeric virus having all the components from HIV-1 except the protein products provided in trans from the MLV env gene. Virions produced from these cells are infectious and replicative but cannot produce another generation of infectious virions because they will lack the env gene products.

24 hours after transfection, these cells are trypsinized and plated in 96 well plates. After the cells have adhered, the media is washed and replaced with media containing the test compound. Virus production is allowed to proceed for an additional 24 hours. The supernatant is then harvested and used to reinfect naive 293A cells. Naive cells that are infected are identified by the luciferase gene product. The number of luciferase positive cells is a measure of the extent of replication and/or infection by the recombinant HIV-1. This assay is also adapted to test the resistance to many clinically accepted anti-HIV-1 drugs by using a HIV-1 genome with several point mutations known to induce resistance to several different classes of anti-HIV drugs. Percentage inhibition is set to 100% for no detectable luciferase positive cells and 0% for the number of positive cells in infected, untreated controls.

To test the size dependence and sequence independence of PS-ODNs on anti-HIV-1 activity, we test PS-ODN randomers that vary in size. When these PS-ODN randomers are tested the HIV-1 CPE assay, we find that as the size of the PS-ODN increases the potency also increases ($IC_{50}$ decreases, see FIGS. 19$a$, $b$ and 20). We also noted that the PS-ODN randomers exhibited no significant toxicity to the host cells in this assay (see FIG. 19$c,d$).

To the best of our knowledge, this is the first time an IC50 for HIV-1 as low as 0.011 µM has been reported for a PS-ODN.

To more clearly elucidate the effective size range for PS-ODN anti-HIV-1 activity, we tested more PS-ODN randomers covering a broader range of sizes from 10 to 80 bases by RA using wild-type HIV-1 (recombinant NL 4-3 (CNDO)). In addition, we tested four protease inhibitors currently used in the clinic (aprenavir, indinavir, lopinavir and saquinavir). We discovered that PS-ODN randomers 10 bases and larger have anti-HIV-1 activity and that the efficacy against HIV-1 also increases with increased PS-ODN randomer length but is saturated at 40 bases (see FIG. 21$e$-$h$ and FIG. 22$b$). Moreover, the 40 and 80 base PS-ODN randomers were almost equivalent in efficacy with the 4 clinical controls (see FIGS. 21$a$-$d$ and 22$a$).

To the best of our knowledge, this is the first time an IC50 for HIV-1 as low as 0.014 µM has been reported for a PS-ODN.

To test the ability of PS-ODN randomers to inhibit a drug resistant strain of HIV, we duplicated the above test using the recombinant MDRC4 strain of HIV-1. This recombinant strain exhibits significant resistance to at least 16 different clinically accepted drugs from all classes: nucleotide RT inhibitors, non-nucleotide RT inhibitors and protease inhibitors. All the PS-ODN randomers perform as well against the resistant strain as they do against the wild type strain (see FIG. 23$e$-$h$). However, three of the four protease inhibitors show a reduction in their efficacy against the mutant strain (see FIG. 23$a$-$d$ and 24), such that the 40 and 80 base PS-ODN randomers are now more potent against this resistant strain than these drugs.

Example 5

Inhibition of RSV

The ability of PS-ODN randomers to inhibit RSV is measured by monitoring CPE with alamar blue (an indirect measure of cellular metabolism). Human larynx carcinoma (Hep2) cells are cultured at 37° C. and 5% $CO_2$ in MEM plus 5% fetal calf serum. Cells are seeded in 96 well plates at a density which yields a confluent monolayer of cells after 5-6 days of growth. The day after plating, cells were infected with RSV (strain A2, $10^{8.2}$ $TCID_{50}$/ml) in the presence of the test compound in a reduced volume for 2 hours. Following inoculation, the media was changed and was supplemented with test compound. 6 days after infection, CPE was monitored by measuring the fluorescent conversion of alamar blue. Toxicity of test compounds in Hep2 cells was monitored by treating uninfected cells for 7 days and measuring alamar blue conversion in these cells. The alamar blue readings in uninfected, untreated cells were set to 100% survival and the readings in infected, untreated cells were set to 0% survival.

To confirm the size dependence and sequence independence of PS-ODNs on anti-RSV activity, we test PS-ODN randomers that vary in size. In addition, we tested the clinically accepted treatment for RSV infection, Ribavirin (Virazole™). When tested in the RSV CPE assay, we find that as the size of the PS-ODN randomer increases, the potency also increases but saturates at 40 bases in size (see FIGS. 25$a$-$c$ and 26). We also noted that 20, 40 and 80 base PS-ODN randomers had $IC_{50}$ values significantly lower than a clinically accepted anti-RSV drug, Ribavirin (see FIGS. 25$a$-$d$ and 26). PS-ODN randomers exhibited no toxicity in Hep2 cells while Ribavirin was significantly toxic (therapeutic index=2.08, see FIG. 25$e$-$h$).

To the best of our knowledge, this is the first time an IC50 for RSV-1 as low as 0.015 µM has been reported for a PS-ODN.

Example 6

Inhibition of Coxsackie Virus B2

The ability of PS-ODN randomers to inhibit COX B2 is measured monitoring CPE with alamar blue (an indirect measure of cellular metabolism). Rhesus monkey kidney (LLC-MK2) cells are cultured at 37° C. and 5% $CO_2$ in MEM plus 5% fetal calf serum. Cells are seeded in 96 well plates at a density which yields a confluent monolayer of cells after 5-6 days of growth. The day after plating, cells were infected with COX B2 (strain Ohio-1, $10^{7.8}$ $TCID_{50}$/ml) in the presence of the test compound in a reduced volume for 2 hours. Following inoculation, the media was changed and was supplemented with test compound. 6 days after infection, CPE was monitored by measuring the fluorescent conversion of alamar blue. Toxicity of test compounds in LLC-MK2 cells was monitored by treating uninfected cells for 7 days and measuring alamar blue conversion in these cells. The alamar blue readings in uninfected, untreated cells were set to 100% survival and the readings in infected, untreated cells were set to 0% survival.

We tested the anti-COX B2 activity of REP 2006 in the COX B2 CPE assay. We found that, while exhibiting some slight toxicity in LLC-MK2 cells (see FIG. 27$b$), this PS-ODN randomer was able to partially rescue infected LLC-MK2 cells from COX B2 infection (see FIG. 27$a$).

Example 7

Inhibition of Vaccinia Virus

We used the vaccinia infection model as a measure of the potential efficacy of our compounds against poxviruses, including smallpox virus. The ability of PS-ODN randomers to inhibit Vaccinia is measured by monitoring CPE with alamar blue (an indirect measure of cellular metabolism). Vero cells are cultured at 37° C. and 5% $CO_2$ in MEM plus 5% fetal calf serum. Cells are seeded in 96 well plates at a density which yields a confluent monolayer of cells after 5-6 days of growth. The day after plating, cells were infected with Vaccinia ($10^{7.9}$ $TCID_{50}$/ml) in the presence of the test compound in a reduced volume for 2 hours. Following inoculation, the media was changed and was supplemented with test compound (all at 10 uM, except for Cidofovir which was used at 50 uM). Five days after infection, the supernatants were harvested. The viral load in the supernatant was determined by reinfection of VERO cells with supernatant diluted 1:100 and the monitoring of CPE 7 days after reinfection by measuring the fluorescent conversion of alamar blue.

We tested PS-ODN randomers that vary in size (REP 2004, 2006 and 2007). In addition, we tested a known effective treatment for Vaccinia infection, Cidofovir (Vistide™). When tested in the Vacinnia CPE assay, we find that treatment with REP 2004, 2006 and 2007 all displayed antiviral activity (i.e. resulted in supernatants which showed a decreased CPE upon reinfection) but that this activity was weaker than that seen for Cidofovir (see FIG. 36).

Example 8

Inhibition of DHBV, Parainfluenza-3 Virus, and Hanta Virus

Because DHBV, Parainfluenza-3 virus and Hanta virus do not readily generate measurable plaques or CPE, we tested the efficacy of REP 2006 in these viruses using a fluorescence focus forming unit (FFFU) detection. In this assay, REP 2006 (at a final concentration of 10 uM) is mixed with the virus which is then adsorbed onto the cells. After adsorption, infected cells are allowed to incubate for an additional 7-14 days at which point they are fixed in methanol. Regions of viral replication are detected by immunofluorescence microscopy against the appropriate viral antigen. For each of the three viruses tested the specific experimental conditions and results are described below:

| Virus | Cellular Host | Antibody for FFFU detection | FFFU count (no drug) | FFFU count (10 uM REP 2006) |
|---|---|---|---|---|
| DHBV (HBV surrogate) | Primary duck hepatocytes | Mouse anti-DHBV IgG | 163 +/− 38.5 | 0 |
| Parainfluenza-3 | LLC-MK2 cells | Mouse anti-PI3 IgG | 288 +/− 126 | 0 |
| Hanta Virus (Strain Prospect Hill) | VERO E6 cells | Mouse anti-SinNombre nucleoprotein IgG | 232.3 +/− 38.17 | 0 |

This initial data shows that at 10 uM, REP 2006 is effective in inhibiting DHBV, Parainfluenza-2 and Hanta Virus. We anticipate that given the robust response in the preliminary test that $IC_{50}$ values will be lower. These data support the efficacy of PS-ODN randomers for the treatment of human infections of Hanta Virus and Hepatitis B (closely related to DHBV) as well as providing a rationale for the immediate treatment of pediatric bronchiolitis caused by RSV and Parainfluenza-3, which may not require differential diagnosis for treatment to begin.

Example 9

Currently Non-Responsive Viruses

To date we have not observed a detectable anti-viral efficacy with PS-ODN randomers (up to 10 uM) without using a delivery system, a drug combination, or a chemical modification in the following viral systems:

| Virus | Strain | Cellular Host | Assay paradigm |
|---|---|---|---|
| Influenza A | H3N2 | MDCK cells | Plaque reduction |
| Corona virus (SARS surrogate) | MHV2 (mouse) MHV-A59 (mouse) HCoV-OC43 (human) | NCTC-1496 cells DBT cells HRT-18 cells | Plaque reduction |
| BVDV (HCV surrogate) | NA | BT cells | CPE by alamar blue |
| Rhinovirus | HGP | HeLa cells | CPE by alamar blue |
| Adenovirus | Human Ad5 | 293A cells | Plaque reduction |

Under the current testing procedures, we did not demonstrate activity. However, the lack of antiviral activity may be due to a lower cellular penetration of the PS-ODN under the conditions of the assays. Nonetheless, additional testing is underway to achieve efficacious results with these viruses. These viruses may respond to PS-ODN when using a delivery system such as a liposomal formulation, in order to increase its intracellular concentration. Also in a combination with another antiviral drug, such as described herein, PS-ODNs may exhibit an antiviral efficacy for these viruses. A chemical modification to increase intracellular concentration may also be useful to render PS-ODNs active against these viruses.

Since we have good evidence that the charge characteristics of a PS-ODN are important for the inhibition of viruses from several different families, we expect that this charge dependent mechanism for the inhibition of viral activity has the potential to inhibit the activity of all encapsidating viruses. The corollary to this is that the lack of detected anti-viral efficacy against those viruses listed in Example 9 suggests that the interaction between the PS-ODN and the structural proteins of these viruses is not strong enough to prevent the interaction of viral proteins during the replication of these viruses. One way of achieving efficacy against these viruses is to alter the charge characteristics of the DNA or anti-viral polymer (e.g., substituting phosphorodithioate for phosphorothioate linkages in DNA) so their affinity for viral proteins is increased.

Example 10

Tests for Determining if an Oligonucleotide Acts Predominantly by a Non-Sequence Complementary Mode of Action An ON, e.g., ODN, in question shall be considered to be acting predominantly by a non-sequence complementary mode of action if it meets the criterion of any one of the 3 tests outlined below.

Test #1—Effect of Partial Degeneracy on Antiviral Efficacy

This test serves to measure the antiviral activity of a particular ON sequence when part of its sequence is made degenerate. If the degenerate version of the ON having the same chemistry retains its activity as described below, is it deemed to be acting predominantly by a non-sequence complementary mode of action. ONs will be made degenerate according to the following rule:

$L_{ON}$=the number of bases in the original ON

X=the number of bases on each end of the oligo to be made degenerate (but having the same chemistry as the original ON)

If $L_{ON}$ is even, then X=$L_{ON}$/4

If $L_{ON}$ is odd, then X=integer ($L_{ON}$/4)+1

Each degenerate base shall be synthesized according to any suitable methodology, e.g., the methodology described herein for the synthesis of PS-ODN randomers.

If the ON is claimed to have an anti-viral activity against a member of the herpesviridae, retroviridae, or paramyxoviridae families, the $IC_{50}$ generation will be performed using the assay described herein for that viral family preferably using the viral strains indicated. If the ON is claimed to have an anti-viral activity against a member of a particular virus family not mentioned above, then the IC50 values shall be generated by a test of antiviral efficacy accepted by the pharmaceutical industry. IC50 values shall be generated using a minimum of seven concentrations of compound, with three or more points in the linear range of the dose response curve. Using this test, the $IC_{50}$ of said ON shall be compared to its degenerate counterpart. If the $IC_{50}$ of the degenerate ON is less than 2-fold greater than the original ON for an ON of 25 bases and less, or is less than 10-fold greater than the original ON for ONs 26 bases or more (based on minimum triplicate measurements, standard deviation not to exceed 15% of mean) then the ON shall be deemed to be functioning predominantly by a non-sequence complementary mode of action.

Test #2—Comparison of Efficacy with Randomer

This test serves to compare the anti-viral efficacy of an ON with the antiviral efficacy of a randomer ON of equivalent size and the same chemistry in the same virus or viral family.

If the ON is claimed to have an anti-viral activity against a member of the herpesviridae, retroviridae, or paramyxoviridae families, the $IC_{50}$ generation will be performed using the assay described herein for that viral family preferably using the viral strains indicated. If the ON is claimed to have an anti-viral activity against a member of a particular virus family not mentioned above, then the IC50 values shall be generated by a test of antiviral efficacy accepted by the pharmaceutical industry. IC50 values shall be generated using a minimum of seven concentrations of compound, with three or more points in the linear range of the dose response curve. Using this test, the $IC_{50}$ of the ON shall be compared to an ON randomer of equivalent size and the same chemistry. If the $IC_{50}$ of the degenerate ON is less than 2-fold greater than the original ON for an ON of 25 bases and less, or is less than 10-fold greater than the original ON for ONs 26 bases or more (based on minimum triplicate measurements, standard deviation not to exceed 15% of mean) then the ON shall be deemed to be functioning predominantly by a non-sequence complementary mode of action.

Test #3—Comparison of Efficacy in a Different Viral Family

This test serves to compare the efficacy of an ON against a target virus whose genome is homologous to the ON with the efficacy of the ON against a second virus whose genome has no homology to ON. In many cases, the different virus will be selected from a different viral family than the viral family of the target virus. The comparison of the relative activities of the ON in the target virus and the second virus is accomplished by using the activities of a randomer of the same length and chemistry in the both viruses to normalize the $IC_{50}$ values for the ON obtained in the two viruses.

Thus, if the ON is claimed to have an anti-viral activity against a certain virus, then the $IC_{50}$ generation will be determined in this virus using one of the assays described herein for the herpesviridae, retroviridae, or paramyxoviridae families, or other assay known in the art. Similarly, $IC_{50}$ generation will be performed for the ON against a second virus using one of the assays as described herein for a virus whose genome has no homology to the sequence of the ON. $IC_{50}$ generation is also performed for a randomer of equivalent size and chemistry against each of the viruses. The $IC_{50}$ efficacies of the randomer against the two viruses are used to normalize the $IC_{50}$ values for the specific ON as follows:

1. An algebraic transformation is applied to the $IC_{50}$ of the ON and the randomer in the first (homologous) virus such that the $IC_{50}$ of the randomer is now 1.
2. An algebraic transformation is applied to the $IC_{50}$ of the ON and the randomer in the second (non-homologous) virus such that the $IC_{50}$ of the randomer in now 1.
3. The fold difference in the IC50s for the ON in the homologus versus the non-homologous virus is calculated by dividing the transformed IC50 of the ON in the non-homologous virus by the transformed IC50 of the ON in the homologous virus.

For an ON less than 25 bases in length, the ON shall be deemed to be acting by a non-sequence complementary mode of action if the fold difference is less than 2. For an ON 25 bases or more in length, the ON shall be deemed to be acting by a non-sequence complimentary mode of action if the fold difference in less than 10.

Test #4: Efficacy in a Different Viral Family

This test serves to determine if an ON has a drug like activity in a virus where the sequence of said ON is not homologous to any portion of the viral genome. Thus the ON shall be tested using one of the assays described herein for the herpesviridae, retroviridae or paramyxoviridae such that the sequence of the ON tested is not homologous to any portion of the genome of the virus to be used. An $IC_{50}$ value shall be generated using a minimum of seven concentrations of the ON, with three or more points in the linear range. If the resulting dose response curve indicates a drug like activity (which can be typically be seen as a decay or sigmoidal curve, having reduced anti-viral efficacy with decreasing concentrations of ON) and the $IC_{50}$ generated from said curve is less than 1 uM, the ON shall be deemed to have a drug like activity. If the ON is deemed to have a drug like activity in a virus to which the ON is not complementary and thus can have no complementary sequence dependent activity, it shall be considered to be acting by a non-sequence complementary mode of action.

Thresholds Used in these Tests

There is no scientific or empirical basis, either in the academic, or industrial fields, to design an antisense ON which is longer than 25 bases. In addition, to our knowledge, there has never been an ON formulation administered in any human trials that used an ON longer than 25 nucleotides.

Given these facts, we have established two different thresholds which we use to define a sequence as acting predominantly by a non-sequence complimentary mode of action. For oligos 25 bases and less, the ON must have an antiviral activity which is at least 2-fold greater than a randomer or a degenerate ON of the same chemistry in order to be considered to be acting predominantly by an antisense mechanism. If an antisense ON is not at least twice as good as a randomer or a degenerate ON, then we conclude that more than half of its activity can be attributed to a non-antisense mode of action.

For ONs 26 bases and larger, the ON must have an antiviral activity which is at least 10-fold (1 log) greater than a randomer or a degenerate ON of the same chemistry to be considered to be acting by an antisense mechanism. Our rationale for this larger threshold it that, given the current state of the art for ON design for antisense, it is reasonable to assume that oligos that are 26 bases and larger and claimed to have an antiviral activity were designed with the knowledge of the invention contained herein (the optimal length of antisense ONs is generally accepted to be between 16 and 21 bases).

The thresholds described in tests 1 to 3 above are the default thresholds. If specifically indicated, other thresholds can be used in the comparison tests 1 to 3 described above. Thus for example, for ONs under 25 bases in length and/or ONs 25 or more bases in length, if specifically indicated the threshold for determining whether an ON is acting principally by a non-sequence complementary mode of action can be any of 10-fold, 8-fold, 6-fold, 5-fold, 4-fold, 3-fold, 2-fold, 1.5-fold, or equal. The threshold described in test 4 above is also a default threshold. If specifically indicated, the threshold for determining whether an ON is acting principally by a non-sequence complementary mode of action in test 4 can be an $IC_{50}$ of less than 1 uM, 0.8 uM, 0.6 uM, 0.5 uM, 0.4 uM, 0.3 uM, 0.2 uM or 0.1 uM. Similarly, though the default is that satisfying any one of the above 4 tests is sufficient, if specifically indicated, the ON can be required to satisfy any two (e.g., tests 1 & 2, 1 & 3, 1 & 4, 2 & 3, 2& 4 and 3 & 4) or any three (e.g., tests 1 & 2 & 3, 1 & 3 & 4, and 2 & 3 & 4) or all 4 of the tests at a default threshold, or if specifically indicated, at another threshold as indicated above.

Antiviral Assay for Herpesviridae

A plaque reduction assay performed as follows:

For HSV-1 or HSV-2, VERO cells (ATCC# CCL-81) are grown to confluence in 12 well tissue culture plates (NUNC or equivalent) at 37 deg C. and 5% $CO_2$ in the presence of MEM supplemented with 10% heat inactivated fetal calf serum and gentamycin, vancomycin and amphoterecin B. Upon reaching confluency, the media is changed to contain 5% fetal calf serum and antibiotics as detailed above supplemented with either HSV-1 (strain KOS, 40-60 PFU total) or HSV-2 (strain MS2, 40-60 PFU total). Viral adsorbtion proceeds for 90 minutes, after which cells are washed and replaced with new "overlay" media containing 5% fetal calf serum and 1% human immunoglobins. Three to four days after adsorbtion, cells are fixed by formalin and plaques are counted following formalin fixation.

For CMV, human fibroblasts are grown as specified for VERO cells in the HSV-1/2 assay. Media components and adsorbtion/overlay procedures are identical with the following exceptions:

1. CMV (strain AD169, 40-60 PFU total) is used to infect cells during the adsorbtion.
2. In the overlay media, 1% human immunoglobins are replaced by 4% sea-plaque agarose.

For other herpesviridae, testing is to be conducted in a plaque assay described above using an appropriate cellular host and 40-60 PFU of virus during the adsorbtion.

This test is only valid if identifiable plaques are present in the absence of compound at the end of the test.

$IC_{50}$ is the concentration at which 50% of the plaques are present compared to the untreated control.

Compound to be tested is present during the adsorption and in the overlay.

Antiviral Assay for Retroviridae

Detection of total p24 in the supernatant of HIV-1 infected cells is performed as follows:

Human PBMCs are infected with a primary isolate of HIV-1 in the presence the compound. The cells are then incubated for an additional 7 days in fresh medium supplemented with the compound after which the levels of p24 in the supernatant are measured using a commercial p24 ELISA kit (BIOMERIEUX or equivalent.)

This test is only valid if there is an accumulation of p24 in the tissue culture supernatant in the infected, untreated cells.

$IC_{50}$ is the concentration at which the amount of p24 detectable is 50% of the p24 present in the untreated control.

Compound to be tested is present during the adsorption and in the media after adsorption.

Antiviral Assay for Paramyxoviridae

For RSV, A measurement of CPE is performed as follows:

Hep2 cells were plated in 96 well plates and allowed to grow overnight in MEM plus 5% fetal calf serum at 37 deg C. and 5% $CO_2$. The next day, cells are infected with RSV (strain A2, $10^{8.2}$ $TCID_{50}$/ml in 100 ul/well) by adsorbtion for 2 hours. Following adsorbtion, media is changed and after 7 days growth, CPE is measured by conversion of Alamar Blue dye to its fluorescent adduct by living cells.

This test is only valid if CPE measurement (as measured by Alamar Blue conversion) in infected cells in the absence of compound is 10% of the conversion measured in uninfected cells.

For purposes of $IC_{50}$ comparison, 100% CPE is set at the conversion level seen in infected cells and 0% CPE is set at the conversion seen in uninfected cells. Therefore $IC_{50}$ is the concentration of compound which generates 50% CPE.

Compound to be tested is present during the adsorption and in the media after adsorption.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to synthesis conditions and compositions of the oligonucleotides. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

TABLE 1

DESCRIPTION OF OLIGONUCLEOTIDES

| | | | |
|---|---|---|---|
| REP 1001 | 20mer from human autonomously replicating sequence | | |
| SEQUENCE | T T G A T A A A T A G T A C T A G G A C | | (SEQ ID NO: 1) |
| PS | ? ? ? ? ? ? ? ? ? ? ? ? ? ? ? ? ? ? ? ? | | |
| | | | |
| REP 2001 | 22mer from HSV-1 origin of replication | | |
| SEQUENCE | G A A G C G T T C G C A C T T C G T C C C A | | (SEQ ID NO: 2) |
| PS | ? ? ? ? ? ? ? ? ? ? ? ? ? ? ? ? ? ? ? ? ? ? | | |
| | | | |
| REP 3007 | 16mer from pUC19/pBR322 origin of replication | | |
| SEQUENCE | C T T G C G G T A T T C G G A A | | (SEQ ID NO: 3) |
| PS | ? ? ? ? ? ? ? ? ? ? ? ? ? ? ? ? | | |
| | | | |
| REP 2002 | 5mer randomer | | |
| SEQUENCE | N N N N N | | |
| PS | ? ? ? ? ? | | |
| | | | |
| REP 2032 | 6mer randomer | | |
| SEQUENCE | N N N N N N | | |
| PS | ? ? ? ? ? ? | | |
| | | | |
| REP 2003 | 10mer randomer | | |
| SEQUENCE | N N N N N N N N N N | | |
| PS | ? ? ? ? ? ? ? ? ? ? | | |
| | | | |
| REP 2009 | 12mer randomer | | |
| SEQUENCE | N N N N N N N N N N N N | | |
| PS | ? ? ? ? ? ? ? ? ? ? ? ? | | |
| | | | |
| REP 2010 | 14mer randomer | | |
| SEQUENCE | N N N N N N N N N N N N N N | | |
| PS | ? ? ? ? ? ? ? ? ? ? ? ? ? ? | | |
| | | | |
| REP 2011 | 16mer randomer | | |
| SEQUENCE | N N N N N N N N N N N N N N N N | | |
| PS | ? ? ? ? ? ? ? ? ? ? ? ? ? ? ? ? | | |
| | | | |
| REP 2012 | 18mer randomer | | |
| SEQUENCE | N N N N N N N N N N N N N N N N N N | | |
| PS | ? ? ? ? ? ? ? ? ? ? ? ? ? ? ? ? ? ? | | |
| | | | |
| REP 2004 | 20mer randomer | | |
| SEQUENCE | N N N N N N N N N N N N N N N N N N N N | | |
| PS | ? ? ? ? ? ? ? ? ? ? ? ? ? ? ? ? ? ? ? ? | | |
| | | | |
| REP 2005 | 30mer randomer | | |
| SEQUENCE | N N N N N N N N N N N N N N N N N N N N N N N N N N N N N N | | |

TABLE 1-continued

DESCRIPTION OF OLIGONUCLEOTIDES

| | | |
|---|---|---|
| QUENCE | | |
| PS | ? ? ? ? ? ? ? ? ? ? ? ? ? ? ? ? ? ? ? ? ? ? ? ? ? ? ? ? ? ? | |
| REP 2006 | 40mer randomer | |
| SE-QUENCE | N N N N N N N N N N N N N N N N N N N N N N N N N N N N N N N N N N N N N N N N | |
| PS | ? ? ? ? ? ? ? ? ? ? ? ? ? ? ? ? ? ? ? ? ? ? ? ? ? ? ? ? ? ? ? ? ? ? ? ? ? ? ? ? | |
| REP 2007 | 80mer randomer | |
| SE-QUENCE | N N N N N N N N N N N N N N N N N N N N N N N N N N N N N N N N N N N N N N N N N N N N N N N N N N N N N N N N N N N N N N N N N N N N N N N N N N N N N N N N 60 | |
| PS | ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? | |
| SE-QUENCE | N N N N N N N N N N N N N N N N N N N N 80 | |
| PS | ? ? ? ? ? ? ? ? ? ? ? ? ? ? ? ? ? ? ? ? | |
| REP 2008 | 120mer randomer | |
| SE-QUENCE | N N N N N N N N N N N N N N N N N N N N N N N N N N N N N N N N N N N N N N N N N N N N N N N N N N N N N N N N N N N N N N 60 | |
| PS | ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? | |
| SE-QUENCE | N N N N N N N N N N N N N N N N N N N N N N N N N N N N N N N N N N N N N N N N N N N N N N N N N N N N N N N N N N N N N 120 | |
| PS | ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? ? | |
| REP 2013 | 10mer randomer | |
| SE-QUENCE no modification | N N N N N N N N N N | |
| REP 2014 | 20mer randomer | |
| SE-QUENCE no modification | N N N N N N N N N N N N N N N N N N N N | |
| REP 2015 | 40mer randomer | |
| SE-QUENCE no modification | N N N N N N N N N N N N N N N N N N N N N N N N N N N N N N N N N N N N N N N N | |
| REP 2016 | 10mer random sequence | |
| SE-QUENCE | T C C G A A G A C G | (SEQ ID NO: 4) |
| PS | ? ? ? ? ? ? ? ? ? ? | |
| REP 2017 | 20mer random sequence | |
| SE-QUENCE | A C A C C T C C G A A G A C G A T A A C | (SEQ ID NO: 5) |
| PS | ? ? ? ? ? ? ? ? ? ? ? ? ? ? ? ? ? ? ? ? | |
| REP 2018 | 40mer random sequence | |
| SE-QUENCE | C T A C A G A C A T A C A C C T C C G A A G A C G A T A A C A C T A G A C A T A | (SEQ IQ NO: 6) |
| PS | ? ? ? ? ? ? ? ? ? ? ? ? ? ? ? ? ? ? ? ? ? ? ? ? ? ? ? ? ? ? ? ? ? ? ? ? ? ? ? ? | |
| REP 2019 | 10mer sequence centered around start codon of HSV-1 IE110 protein (NCBI accession # X04614) | |
| SE-QUENCE | C C C C C A T G G A | (SEQ ID NO: 7) |
| PS | ? ? ? ? ? ? ? ? ? ? | |
| REP 2020 | 20mer sequence centered around start codon of HSV-1 IE110 protein (NCBI accession # X04614) | |
| SE-QUENCE | T A C G A C C C C C A T G G A G C C C C | (SEQ ID NO: 8) |
| PS | ? ? ? ? ? ? ? ? ? ? ? ? ? ? ? ? ? ? ? ? | |
| REP 2021 | 40mer sequence centered around start codon of HSV-1 IE110 protein (NCBI accession # X04614) | |
| SE-QUENCE | T C C A G C C G C A T A C G A C C C C C A T G G A G C C C C G C C C C G G A G C | (SEQ ID NO: 9) |
| PS | ? ? ? ? ? ? ? ? ? ? ? ? ? ? ? ? ? ? ? ? ? ? ? ? ? ? ? ? ? ? ? ? ? ? ? ? ? ? ? ? | |

TABLE 1-continued

DESCRIPTION OF OLIGONUCLEOTIDES

REP 2024 40mer randomer
SEQUENCE  N N N N N N N N N N N N N N N N N N N N N N N N N N N N N N N N N N N N N N N N
PS         ? ? ? ? ? ? ? ? ? ? ? ? ? ? ? ? ? ? ? ? ? ? ? ? ? ? ? ? ? ? ? ? ? ? ? ? ? ? ? ?
2-O Me     ? ? ? ?                                                                  ? ? ? ?

REP 2026 40mer randomer
SEQUENCE  N N N N N N N N N N N N N N N N N N N N N N N N N N N N N N N N N N N N N N N N
PS         ? ? ? ?                                                                  ? ? ? ?

REP 2036 21mer commercially marketed antisense against CMV (vitravine(fomvirisen) SYNTHESIZED INTERNALLY
SEQUENCE  G C G T T T G C T C T T C T T C T T G C G                                            (SEQ ID NO: 10)
PS         ? ? ? ? ? ? ? ? ? ? ? ? ? ? ? ? ? ? ? ? ?

REP 2036 © 21mer commercially marketed antisense against CMV (vitravine/fomvirisen) COMMERCIAL PRODUCT (cGMP)
SEQUENCE  G C G T T T G C T C T T C T T C T T G C G                                            (SEQ ID NO: 11)
PS         ? ? ? ? ? ? ? ? ? ? ? ? ? ? ? ? ? ? ? ? ?

A20 20 mer
SEQUENCE  A A A A A A A A A A A A A A A A A A A A -FITC                                         (SEQ ID NO: 12)
PS         ? ? ? ? ? ? ? ? ? ? ? ? ? ? ? ? ? ? ? ?

G20 20 mer
SEQUENCE  G G G G G G G G G G G G G G G G G G G G -FITC                                         (SEQ ID NO: 13)
PS         ? ? ? ? ? ? ? ? ? ? ? ? ? ? ? ? ? ? ? ?

C20 20 mer
SEQUENCE  C C C C C C C C C C C C C C C C C C C C -FITC                                         (SEQ ID NO: 14)
PS         ? ? ? ? ? ? ? ? ? ? ? ? ? ? ? ? ? ? ? ?

T20 20 mer
SEQUENCE  T T T T T T T T T T T T T T T T T T T T -FITC                                         (SEQ ID NO: 15)
PS         ? ? ? ? ? ? ? ? ? ? ? ? ? ? ? ? ? ? ? ?

AC10 20 mer
SEQUENCE  A C A C A C A C A C A C A C A C A C A C -FITC                                         (SEQ ID NO: 16)
PS         ? ? ? ? ? ? ? ? ? ? ? ? ? ? ? ? ? ? ? ?

AG10 20 mer
SEQUENCE  A G A G A G A G A G A G A G A G A G A G -FITC                                         (SEQ ID NO: 17)
PS         ? ? ? ? ? ? ? ? ? ? ? ? ? ? ? ? ? ? ? ?

TC10 20 mer
SEQUENCE  T C T C T C T C T C T C T C T C T C T C -FITC                                         (SEQ ID NO: 18)
PS         ? ? ? ? ? ? ? ? ? ? ? ? ? ? ? ? ? ? ? ?

TG10 20 mer
SEQUENCE  T G T G T G T G T G T G T G T G T G T G -FITC                                         (SEQ ID NO: 19)
PS         ? ? ? ? ? ? ? ? ? ? ? ? ? ? ? ? ? ? ? ?

REP 2029 40 mer
SEQUENCE  A A A A A A A A A A A A A A A A A A A A A A A A A A A A A A A A A A A A A A A A        (SEQ ID NO: 20)
PS         ? ? ? ? ? ? ? ? ? ? ? ? ? ? ? ? ? ? ? ? ? ? ? ? ? ? ? ? ? ? ? ? ? ? ? ? ? ? ? ?

REP 2028 40 mer
SEQUENCE  G G G G G G G G G G G G G G G G G G G G G G G G G G G G G G G G G G G G G G G G        (SEQ ID NO: 21)
PS         ? ? ? ? ? ? ? ? ? ? ? ? ? ? ? ? ? ? ? ? ? ? ? ? ? ? ? ? ? ? ? ? ? ? ? ? ? ? ? ?

REP 2031 40 mer
SEQUENCE  C C C C C C C C C C C C C C C C C C C C C C C C C C C C C C C C C C C C C C C C        (SEQ ID NO: 22)
PS         ? ? ? ? ? ? ? ? ? ? ? ? ? ? ? ? ? ? ? ? ? ? ? ? ? ? ? ? ? ? ? ? ? ? ? ? ? ? ? ?

REP 2030 40 mer

TABLE 1-continued

DESCRIPTION OF OLIGONUCLEOTIDES

| | | | |
|---|---|---|---|
| SEQUENCE | TTTTTTTTTTTTTTTTTTTTTTTTTTTTTTTTTTTTTTTT | | (SEQ ID NO: 23) |
| PS | ? ? ? ? ? ? ? ? ? ? ? ? ? ? ? ? ? ? ? ? ? ? ? ? ? ? ? ? ? ? ? ? ? ? ? ? ? ? ? ? | | |
| REP 2055 | 40 mer | | |
| SEQUENCE | ACACACACACACACACACACACACACACACACACACACAC | | (SEQ ID NO: 24) |
| PS | ? ? ? ? ? ? ? ? ? ? ? ? ? ? ? ? ? ? ? ? ? ? ? ? ? ? ? ? ? ? ? ? ? ? ? ? ? ? ? ? | | |
| REP 2056 | 40 mar | | |
| SEQUENCE | TCTCTCTCTCTCTCTCTCTCTCTCTCTCTCTCTCTCTCTC | | (SEQ ID NQ: 25) |
| PS | ? ? ? ? ? ? ? ? ? ? ? ? ? ? ? ? ? ? ? ? ? ? ? ? ? ? ? ? ? ? ? ? ? ? ? ? ? ? ? ? | | |
| REP 2057 | 40 mer | | |
| SEQUENCE | AGAGAGAGAGAGAGAGAGAGAGAGAGAGAGAGAGAGAGAG | | (SEQ ID NO: 26) |
| PS | ? ? ? ? ? ? ? ? ? ? ? ? ? ? ? ? ? ? ? ? ? ? ? ? ? ? ? ? ? ? ? ? ? ? ? ? ? ? ? ? | | |
| REP 2059 | 20mer RNA randomer | | |
| SEQUENCE | NNNNNNNNNNNNNNNNNNNN | | |
| PS | ? ? ? ? ? ? ? ? ? ? ? ? ? ? ? ? ? ? ? ? | | |
| REP 2060 | 30mer RNA randomer | | |
| SEQUENCE | NNNNNNNNNNNNNNNNNNNNNNNNNNNNNN | | |
| PS | ? ? ? ? ? ? ? ? ? ? ? ? ? ? ? ? ? ? ? ? ? ? ? ? ? ? ? ? ? ? | | |

What is claimed is:

1. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the herpesviridae.

2. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets HSV-1.

3. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets HSV-2.

4. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets cytomegalovirus.

5. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the hepadnaviridae.

6. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets hepatitis B virus.

7. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the poxviridae.

8. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the paramyxoviridae.

9. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets respiratory syncytial virus.

10. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets parainfluenza virus.

11. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the bunyaviridae.

12. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets hantavirus.

13. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the filoviridae.

14. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets Ebola virus.

15. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets Marburg virus.

16. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the flaviviridae.

17. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets yellow fever virus, dengue virus or West Nile virus.

18. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets hepatitis C virus.

19. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the orthomyxoviridae.

20. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets influenza virus.

21. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets influenza A virus.

22. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets influenza B virus.

23. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the togaviridae.

24. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the coronaviridae.

25. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the rhabdoviridae.

26. A method for the prophylaxis or treatment of a viral infection in a subject, comprising administering to a subject in need of such treatment a therapeutically effective amount of at least one pharmacologically acceptable phosphorothioate oligonucleotide, wherein said oligonucleotide is fully phosphorothioated, wherein said oligonucleotide is between 20 and 120 nucleotides in length, wherein the antiviral activity of said oligonucleotide occurs by a non-sequence dependent mode of action, and wherein said oligonucleotide targets a member of the arenaviridae.

27. The method of any of claims 1 to 26, wherein said formulation contains an oligonucleotide which comprises at least one deoxyribonucleic acid and one ribonucleic acid.

28. The method of any of claims 1 to 26, wherein said formulation contains an oligonucleotide that is a heteropolymer comprised of dinucleotide repeats, wherein each dinucleotide contains two different nucleotides selected from the group consisting of adenosine, guanosine, cytidine, thymine or uridine.

29. The method of any of claims 1 to 26, wherein said formulation contains an oligonucleotide that is a heteropolymer comprised of alternating adenosine and cytidine residues.

30. The method of any of claims 1 to 26, wherein said formulation contains an oligonucleotide consisting of SEQ ID NO:24.

31. The method of any of claims 1 to 26, wherein said oligonucleotide further comprises at least one 5-methylcytosine base.

32. The method of any of claims 1 to 26, wherein said formulation contains an oligonucleotide that is a heteropolymer comprised of alternating adenosine and guanosine residues.

33. The method of any of claims 1 to 26, wherein said formulation contains an oligonucleotide consisting of SEQ ID NO:26.

34. The method of any of claims 1 to 26, wherein said oligonucleotide further comprises at least one 2'-O methyl modification to the ribose moiety.

35. The method of any of claims 1 to 26, wherein said oligonucleotide further comprises at least one 2'-O (2-methoxyethyl) modification to the ribose moiety.

36. The method of any of claims 1 to 26, wherein said oligonucleotide further comprises at least one 2'-modification to the ribose moiety.

37. The method of any of claims 1 to 26, wherein said oligonucleotide has all ribose moieties modified with a 2'-O methyl modification.

38. The method of any of claims 1 to 26, wherein said oligonucleotide has all ribose moieties modified with a 2'-O (2-methoxyethyl) modification.

39. The method of any of claims 1 to 26, wherein said oligonucleotide has all ribose moieties modified with a 2' ribose modification.

40. The method of any of claims 1 to 26, wherein said oligonucleotide is a concatemer consisting of two or more oligonucleotide sequences joined by a linker.

41. The method of any of claims 1 to 26, adapted for delivery by a mode selected from the group consisting of intraocular injection, oral ingestion, enterally, inhalation, cutaneous injection, subcutaneous injection, intramuscular injection, intraperitoneal injection, intrathecal injection, intratracheal injection and intravenous injection.

42. The method of any of claims 1 to 26, wherein said oligonucleotide is administered with at least one other antiviral drug in combination.

43. The method of any of claims 1 to 26, wherein said oligonucleotide is between 30 and 120 nucleotides in length.

* * * * *

SEQUENCE LISTING

```
<160> NUMBER OF SEQ ID NOS: 36

<210> SEQ ID NO 1
<211> LENGTH: 20
<212> TYPE: DNA
<213> ORGANISM: Homo sapiens

<400> SEQUENCE: 1
ttgataaata gtactaggac                                              20

<210> SEQ ID NO 2
<211> LENGTH: 22
<212> TYPE: DNA
<213> ORGANISM: Human herpesvirus 1

<400> SEQUENCE: 2
gaagcgttcg cacttcgtcc ca                                           22

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cttgcggtat tcggaa                                                  16

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 4
tccgaagacg                                                              10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acacctccga agacgataac                                                   20

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctacagacat acacctccga agacgataac actagacata                             40

<210> SEQ ID NO 7
<211> LENGTH: 10
<212> TYPE: DNA
<213> ORGANISM: Human herpesvirus 1

<400> SEQUENCE: 7
cccccatgga                                                              10

<210> SEQ ID NO 8
<211> LENGTH: 20
<212> TYPE: DNA
<213> ORGANISM: Human herpesvirus 1

<400> SEQUENCE: 8
tacgaccccc atggagcccc                                                   20

<210> SEQ ID NO 9
<211> LENGTH: 40
<212> TYPE: DNA
<213> ORGANISM: Human herpesvirus 1

<400> SEQUENCE: 9
tccagccgca tacgaccccc atggagcccc gccccggagc                             40

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcgtttgctc ttcttcttgc g                                                 21

<210> SEQ ID NO 11
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 11
gcgtttgctc ttcttcttgc g                                                  21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaaaaaaa aaaaaaaaaa                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggggggggg gggggggggg                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cccccccccc cccccccccc                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tttttttttt tttttttttt                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
acacacacac acacacacac                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 17
agagagagag agagagagag                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tctctctctc tctctctctc                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgtgtgtgtg tgtgtgtgtg                                              20

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aaaaaaaaaa aaaaaaaaaa aaaaaaaaaa aaaaaaaaaa                        40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gggggggggg gggggggggg gggggggggg gggggggggg                        40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cccccccccc cccccccccc cccccccccc cccccccccc                        40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 23
tttttttttt tttttttttt tttttttttt tttttttttt                         40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
acacacacac acacacacac acacacacac acacacacac                         40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tctctctctc tctctctctc tctctctctc tctctctctc                         40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agagagagag agagagagag agagagagag agagagagag                         40

<210> SEQ ID NO 27
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 nucleotides

<400> SEQUENCE: 27
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa  120

<210> SEQ ID NO 28
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 nucleotides

<400> SEQUENCE: 28
cccccccccc cccccccccc cccccccccc cccccccccc cccccccccc cccccccccc   60
cccccccccc cccccccccc cccccccccc cccccccccc cccccccccc cccccccccc  120

<210> SEQ ID NO 29
<211> LENGTH: 120
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 nucleotides

<400> SEQUENCE: 29
gggggggggg gggggggggg gggggggggg gggggggggg gggggggggg gggggggggg        60
gggggggggg gggggggggg gggggggggg gggggggggg gggggggggg gggggggggg       120

<210> SEQ ID NO 30
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 nucleotides

<400> SEQUENCE: 30
tttttttttt tttttttttt tttttttttt tttttttttt tttttttttt tttttttttt        60
tttttttttt tttttttttt tttttttttt tttttttttt tttttttttt tttttttttt       120

<210> SEQ ID NO 31
<211> LENGTH: 240
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 'ac' repeats

<400> SEQUENCE: 31
acacacacac acacacacac acacacacac acacacacac acacacacac acacacacac        60
acacacacac acacacacac acacacacac acacacacac acacacacac acacacacac       120
acacacacac acacacacac acacacacac acacacacac acacacacac acacacacac       180
acacacacac acacacacac acacacacac acacacacac acacacacac acacacacac       240

<210> SEQ ID NO 32
<211> LENGTH: 240
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 'ag' repeats

<400> SEQUENCE: 32
agagagagag agagagagag agagagagag agagagagag agagagagag agagagagag        60
agagagagag agagagagag agagagagag agagagagag agagagagag agagagagag       120
agagagagag agagagagag agagagagag agagagagag agagagagag agagagagag       180
agagagagag agagagagag agagagagag agagagagag agagagagag agagagagag       240

<210> SEQ ID NO 33
<211> LENGTH: 240
<212> TYPE: DNA
<213> ORGANISM: Artificial Sequence
<220> FEATURE:
<223> OTHER INFORMATION: Description of Artificial Sequence: Synthetic
```

```
                                oligonucleotide
<220> FEATURE:
<223> OTHER INFORMATION: this sequence may encompass 2-120 'at' repeats

<400> SEQUENCE: 33
atatatatat atatatatat atatatatat atatatatat atatatatat atatatatat      60
atatatatat atatatatat atatatatat atatatatat atatatatat atatatatat     120
atatatatat atatatatat atatatatat atatatatat atatatatat atatatatat     180
atatatatat atatatatat atatatatat atatatatat atatatatat atatatatat     240

<210> SEQ ID NO 34
<211> LENGTH: 240
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 'cg' repeats

<400> SEQUENCE: 34
cgcgcgcgcg cgcgcgcgcg cgcgcgcgcg cgcgcgcgcg cgcgcgcgcg cgcgcgcgcg      60
cgcgcgcgcg cgcgcgcgcg cgcgcgcgcg cgcgcgcgcg cgcgcgcgcg cgcgcgcgcg     120
cgcgcgcgcg cgcgcgcgcg cgcgcgcgcg cgcgcgcgcg cgcgcgcgcg cgcgcgcgcg     180
cgcgcgcgcg cgcgcgcgcg cgcgcgcgcg cgcgcgcgcg cgcgcgcgcg cgcgcgcgcg     240

<210> SEQ ID NO 35
<211> LENGTH: 240
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 'ct' repeats

<400> SEQUENCE: 35
ctctctctct ctctctctct ctctctctct ctctctctct ctctctctct ctctctctct      60
ctctctctct ctctctctct ctctctctct ctctctctct ctctctctct ctctctctct     120
ctctctctct ctctctctct ctctctctct ctctctctct ctctctctct ctctctctct     180
ctctctctct ctctctctct ctctctctct ctctctctct ctctctctct ctctctctct     240

<210> SEQ ID NO 36
<211> LENGTH: 240
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: this sequence may encompass 2-120 'gt' repeats

<400> SEQUENCE: 36
gtgtgtgtgt gtgtgtgtgt gtgtgtgtgt gtgtgtgtgt gtgtgtgtgt gtgtgtgtgt      60
gtgtgtgtgt gtgtgtgtgt gtgtgtgtgt gtgtgtgtgt gtgtgtgtgt gtgtgtgtgt     120
gtgtgtgtgt gtgtgtgtgt gtgtgtgtgt gtgtgtgtgt gtgtgtgtgt gtgtgtgtgt     180
gtgtgtgtgt gtgtgtgtgt gtgtgtgtgt gtgtgtgtgt gtgtgtgtgt gtgtgtgtgt     240
```